US010114012B2

(12) United States Patent
Gernez et al.

(10) Patent No.: US 10,114,012 B2
(45) Date of Patent: Oct. 30, 2018

(54) METHODS AND ASSAYS FOR DETECTING AND QUANTIFYING PURE SUBPOPULATIONS OF WHITE BLOOD CELLS IN IMMUNE SYSTEM DISORDERS

(75) Inventors: Yael Gernez, Palo Alto, CA (US); Leonore A. Herzenberg, Stanford, CA (US); Kari Nadeau, Los Altos Hills, CA (US); Rabindra Tirouvanziam, Redwood Court, CA (US)

(73) Assignee: THE BOARD OF TRUSTEES OF THE LELAND STANFORD JUNIOR UNIVERSITY, Palo Alto, CA (US)

( * ) Notice: Subject to any disclaimer, the term of this patent is extended or adjusted under 35 U.S.C. 154(b) by 1514 days.

(21) Appl. No.: 12/610,940

(22) Filed: Nov. 2, 2009

(65) Prior Publication Data

US 2010/0112628 A1    May 6, 2010

Related U.S. Application Data

(60) Provisional application No. 61/110,283, filed on Oct. 31, 2008.

(51) Int. Cl.
| | |
|---|---|
| G01N 1/30 | (2006.01) |
| G01N 33/48 | (2006.01) |
| G01N 33/53 | (2006.01) |
| G01N 33/50 | (2006.01) |

(52) U.S. Cl.
CPC ..... *G01N 33/5094* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 4,284,412 A | 8/1981 | Hansen | |
| 5,179,026 A | 1/1993 | Matsuda | |
| 5,296,378 A | 3/1994 | Sakata | |
| 5,968,755 A | 10/1999 | Roederer | |
| 2004/0265925 A1* | 12/2004 | Havranova | 435/7.21 |
| 2008/0050830 A1* | 2/2008 | Floriano et al. | 436/63 |

OTHER PUBLICATIONS

Ebo et al. (Flow cytometric analysis of in vitro activated basophils, specific IgE and skin tests in the diagnosis of pollen-associated food allergy, 2005, Cytometry Part B, vol. 64B, pp. 28-33).*
Vreman et al. (Carbon monoxide in blood: an improved microliter blood-sample collection system, with rapid analysis by gas chromatography, 1984, Clinical Chemistry, vol. 30, pp. 1382-1386).*
Ewan (Clinical study of peanut and nut allergy in 62 consecutive patients: new features and associations, British Medical Journal, 1996, vol. 312, pp. 1074-1078).*
Torres et al. (The diagnostic interpretation of basophil activation test in immediate allergic reactions to betalactams, 2004, Clinical and Experimental Allergy, vol. 34, pp. 1768-1775).*
Wood (9-color and 10-color flow cytometry in the clinical laboratory, Archives of Pathology and Laboratory Medicine, 2006, vol. 130, pp. 680-690).*
Bradford et al. (Dead cell stains in flow cytometry: A comprehensive analysis, 2008, XXIV International Congress, Program and Abstracts, vol. 417, 1 page).*
Vega (Eosinophil cationic protein is not only a distinctive eosinophil protein, 2008, Thorax, vol. 63, p. 185).*
Boumiza et al. (The basophil activation test by flow cytometry: recent developments in clinical studies, standardization and emerging perspectives, 2005, Clinical and Molecular Allergy, vol. 3:9, 8 pages).*
Kahlert et al. Clin. Exp. Allerg. 22:1266-1272, 2003.*
Valent et al. 'Assays for measuring in vitro basophil activation induced by recombinant allergens.' Methods 32:265-270, 2004.*
Kvedariene et al. 'The need for a biological diagnosis of penicillin allergy.' Clin. Exp. Allerg. 38:869-871, 2008.*
Ebo, D.G. et al., Cytometry Part B (Clinical Cytometry)64B:28-33 (2005).
Wood, B., Arch. Pathol. Lab. Med., vol. 130, May 2006, pp. 680-690.
Ewan, P.W., BMJ 1996; 312: 1074-8.
Torres, M.J., Clin. Exp. Allergy 2004; 34: 1768-1775.
Monteseirin, J. et al., Thorax 2008 63: 185.
Vreman, H.J. et al., Clin. Chem. 30/8, 1382-1386 (1984).
Boumiza, R. et al., Clinical and Molecular Allergy 2005, 3:9, pp. 1-8.
Chirumbolo, S. et al., Clinical and Molecular Allergy 2008, 6:12.
Monneret, G. et al., Anesthesiology 2000, 92: 275-277.
Likura, M. et al., Journal of Leukocyte Biology, vol. 70, Jul. 2001, pp. 113-120.
Nowak-Wegrzyn, A et al., J. Allergy Clin. Immunol. 2009; 123(6 Suppl): S365-S383).

* cited by examiner

*Primary Examiner* — Nora M Rooney
(74) *Attorney, Agent, or Firm* — McCarter & English, LLP; Beverly W. Lubit

(57) ABSTRACT

Methods for detecting nonactivated basophils in a whole blood sample obtained from a normal healthy subject, methods for determining a subject's susceptibility to an allergic reaction to an allergen, where the subject has no known allergy to the allergen, methods for measuring a response to challenge with a potential allergen in a whole blood sample obtained from a subject with known allergic reactivity to allergens other than the potential allergen; and an in vitro system for reliable detection or quantification of a specific white blood cell population in a whole blood sample are described.

12 Claims, 13 Drawing Sheets

METHODS AND ASSAYS FOR DETECTING AND QUANTIFYING PURE SUBPOPULATIONS OF WHITE BLOOD CELLS IN IMMUNE SYSTEM DISORDERS

CROSS REFERENCE

This application claims the benefit of priority of U.S. provisional application 61/110,283, filed Oct. 31, 2008, incorporated herein by reference n its entirety.

STATEMENT OF GOVERNMENT FUNDING

This invention was made with government support under Grant Dean Fellowship Morgridge and Gallo Fellowship, AAAAI fellowship awarded by the Stanford and AAAAI foundation. The government has certain rights in the invention.

FIELD OF THE INVENTION

The described invention relates to methods and assays for detecting and quantifying subpopulations of white blood cells in human blood samples for diagnosing and monitoring immune system disorders, conditions or diseases.

BACKGROUND

Allergy

Immune responses that are elicited in response to many otherwise innocuous environmental allergens, as well as in response to infections with many parasites, often are associated with high levels of immunoglobulin E ("IgE") production. The amount of immunoglobulins E/High affinity IgE receptor at the surface of basophils can be informative of the allergic status as well as the fact that patients can be on therapy. It generally is believed these immune responses are promoted by antigen-specific T helper 2 (Th2) cells and that unwanted IgE-associated immune responses (i.e., allergic diseases) are the unfortunate result of the immune system perceiving and responding to otherwise essentially harmless allergens as if they were derived from a parasite.

In the context of allergic diseases, allergen challenge of a sensitized host can result in a range of tissue responses, depending on such factors as the route and dose of allergen challenge, and on whether the allergen challenge represents a single transient exposure, results in the persistence of the allergen, or occurs seasonally (such as hay fever) or in some other repetitive fashion. Tissue responses also may be affected importantly by the genetic background of the host and by diverse nongenetic factors (such as certain concurrent infections), which can modify the host's response to allergen.

The effector phases of IgE-associated immune responses may be described as occurring in three temporal patterns: (i) acute reactions (acute response), which develop within seconds or minutes of allergen exposure; (ii) late-phase reactions (late phase response), which develop within hours of allergen exposure, often after at least some of the effects of the acute reaction have partially diminished; and (iii) chronic allergic inflammation (chronic allergic response), which can persist for days to years.

In the early stages of allergy, a hypersensitivity reaction against an allergen, encountered for the first time, causes a response in Th2 cells, a subset of T cells that produce the cytokine interleukin-4 ("IL-4"). The Th2 cells interact with B cells (lymphocytes that produce antibodies against antigens), and, coupled with the effects of IL-4, stimulate the B cells to begin production and secretion of IgE. The secreted IgE circulates in the blood and binds to the high affinity IgE receptor ("FcεRI") on the surface of mast cells and basophils, both of which are involved in the acute inflammatory response. At this state, the IgE-coated cells are sensitized to the allergen.

If later exposure to the same allergen occurs, the allergen can bind to the IgE molecules held on the surface of the mast cells or basophils. Cross-linking of the IgE and Fc receptors occurs when more than one IgE-receptor complex interacts with the same allergenic molecule, and activates the sensitized cell. Subsequently, these activated mast cells and basophils undergo the process of degranulation during which they release histamine and other inflammatory chemical mediators, such as cytokines, interleukins and prostaglandins, from their granules into the surrounding tissue causing several systemic effects, such as, for example, but not limited to, vasodilation, mucous secretion, nerve stimulation, and smooth muscle contraction. This may result in rhinorrhea (runny nose), itchiness, dyspnea (difficulty in breathing), or anaphylaxis. Depending on the individual patient, allergen, and mode of introduction, the symptoms may be system-wide (classical anaphylaxis) or localized to particular body systems, such as asthma (localized to the respiratory system) and eczema (localized to the dermis).

After the chemical mediators of the acute response subside, late phase responses may occur. Tissues may become red and swollen due to the migration, initiated by the release of cytokines from mast cells and basophils, of other leukocytes, such as neutrophils, lymphocytes, eosinophils and macrophages, to the initial site. Platelets also may participate. The reaction usually is seen from 2 hours to 24 hours after the original reaction.

Allergic Diseases

Allergic diseases are the group of hypersensitivity disorders that may be (a) associated with the production of specific IgE to environmental allergens and (b) thought to involve, as part of their pathogenesis, IgE-mediated reactions. These reactions are prevalent. Allergic reaction can be IgE independent as well.

Anaphylaxis

Anaphylaxis is an acute, systemic, hypersensitivity response to allergen, which typically involves multiple organ systems and which, if untreated, rapidly can lead to death. The vast majority of anaphylactic or anaphylactoid reactions encountered clinically are due to IgE-dependent reactions to penicillin or other antibiotics, foods, or the venom of stinging insects. Further, anaphylaxis also may be IgE independent. It generally is believed that most, if not all, of the signs and symptoms of IgE-associated anaphylaxis in humans reflect (a) the systemic, FcεRI-dependent activation of mast cells and/or basophils and (b) the end-organ consequences of the release of mediators by these cells. Mild cases of acute systemic allergic reactions may primarily involve the skin, which exhibits widespread areas of increased vascular permeability, erythema, and itching (hives). In more severe cases, greatly increased vascular permeability occurs in multiple organ systems, including the upper airways, leading to laryngeal edema and upper airway obstruction. Further, the rapid loss of intravascular fluid volume, together with other consequences of mediator release in anaphylaxis, such as loss of tone in capacitance vessels and decreased contractility of the heart, leads to hypotension and shock. Breathing also may be impaired by marked narrowing of the lower airways, resulting in a severe case of acute asthma, and there may be pronounced gastrointestinal signs and symptoms, such as nausea and vomiting.

Allergic Rhinitis

Allergic rhinitis (hay fever) is one of the most prevalent allergic diseases. It generally is believed that symptoms, which include sneezing, nasal congestion and itching, and rhinorrhea (runny nose), primarily reflect the IgE-dependent release of mediators by effector cells (mainly mast cells and basophils) in response to aeroallergens. Accordingly, symptoms may be seasonal, correlating with the presence of the offending grass, weed or tree pollens, or mold spores, or year-round (for example, the presence of dust mites or animal dander). Typically, symptoms develop rapidly upon exposure to allergen. Nasal tissues usually exhibit marked infiltration with eosinophils and basophils.

Asthma

Asthma is an airway disease that can be classified physiologically as a variable and partially reversible obstruction to air flow, and pathologically with overdeveloped mucus glands, airway thickening due to scarring and inflammation, and bronchoconstriction (the narrowing of the airways in the lungs due to the tightening of surrounding smooth muscle). Bronchial inflammation also causes narrowing due to edema and swelling caused by an immune response to allergens. In human allergic asthma, it generally is believed that IgE-dependent mast-cell activation importantly contributes to acute allergen-induced bronchoconstriction, and that mast cells can contribute to the airway inflammation associated with this disorder. In humans, the FcεRI can be expressed on several potential effector cells in addition to basophils and mast cells, including monocytes, macrophages, eosinophils, neutrophils and platelets. IgE can directly or indirectly upregulate FcεRI expression on basophils and mast cells, and, by binding to this receptor, prime the cells to release increased amounts of key mediators, such as histamine, IL-4, IL-13, MIP-1α and other cytokines.

Atopic Dermatitis

Atopic dermatitis is an inflammatory, chronically relapsing, non-contagious and pruritic skin disease. The skin of a patient with atopic dermatitis reacts abnormally and easily to irritants, food, and environmental allergens and becomes red, flaky and very itchy. It also becomes vulnerable to surface infections caused by bacteria. The skin on the flexural surfaces of the joints (for example, inner sides of elbows and knees) is the most commonly affected region in humans. Naturally occurring lesions of atopic dermatitis may include T cells, along with eosinophils and their products, although their roles are unclear.

Atopic dermatitis often occurs together with other atopic diseases like hay fever, asthma and conjunctivitis. It is a familial and chronic disease and its symptoms can increase or disappear over time. Atopic dermatitis in older children and adults often is confused with psoriasis. Atopic dermatitis afflicts humans, particularly young children; it is also a well-characterized disease in domestic dogs. There is no cure for atopic eczema, and its causes are not well understood.

Mastocytosis

Mastocytosis refers to a group of disorders characterized by excessive mast cell accumulation in one or multiple tissues. Mastocytosis is subdivided into two groups of disorders: systemic or cutaneous. A subset of of patients with recurrent anaphylaxis, but without mastocytosis, have been reported to carry clonal markers of mast cell disease such as, for example, D816V c-kit mutation. Anaphylaxis can be observed in both cutaneous and systemic mastocytosis.

Eosinophilic Esophagitis

Eosinophilic esophagitis (EoE) is part of a heterogeneous group of eosinophil-associated gastrointestinal disorders that is characterized by high numbers of eosinophils infiltrating into the esophagus. While the incidence of EoE is increasing, precise mechanisms of this disease remain largely unknown, though EoE is associated with allergy. Currently, eosphagogastroduodenoscopy (EGD) and histological examination of esophageal biopsies are required for the diagnosis of EoE, and repeated procedures often are employed for the assessment of response to therapy. Current treatments rely on avoidance of specific food and airborne allergens in atopic patients, anti-inflammatory drugs, such as glucocorticoids, or experimental drugs, such as mepolizumab. The need for less invasive procedures to diagnose and monitor EoE remains.

Angioedema

Angioedema is a self-limited, localized swelling of the skin, which results from extravasation of fluid into interstitial tissues. It affects the skin and mucosal tissues of the face, lips, mouth, and throat, larynx, extremities, and genitalia, often in an asymmetric pattern. Bowel wall involvement presents as a colicky abdominal pain. Angioedema may occur in isolation, accompanied by urticaria, or as a component of anaphylaxis. Mast cell-mediated angioedema is associated with urticaria and/or pruritus in 90 percent of cases. There are many agents, including drugs and allergens, that can result in mast cell-mediated angioedema.

Autoimmune Disorders

The term "autoimmune disorder" as used herein refers to disease, disorders or conditions in which the body's immune system, which normally fights infections and viruses, is misdirected and attacks the body's own normal, healthy tissue. Mast cells are implicated in the pathology associated with the autoimmune disorders rheumatoid arthritis, bullous pemphigoid, and multiple sclerosis. They have been shown to be involved in the recruitment of inflammatory cells to the joints (e.g. rheumatoid arthritis) and skin (e.g. bullous pemphigoid) this activity is dependent on antibodies and complement components.

In the condition autoimmune mast cell release, recurrent episodes of angioedema and urticaria may persist over months to years. Angioedema is present in up to 50 percent of patients with chronic urticaria. In this condition, symptoms occur independently of external triggers. One proposed mechanism is the formation of autoantibodies to either IgE or the IgE receptor on mast cells, which then activate the cells intermittently. Chronic urticaria can be associated with the presence of Anti-Fc(episilon)RI auto antibodies. Patients with autoantibodies have both markedly reduced basophil numbers and basophil histamine release Monoclonal Gammopathies (Paraproteinemias or Dysproteinemias)

The monoclonal gammopathies (paraproteinemias or dysproteinemias) are a group of disorders characterized by the proliferation of a single clone of plasma cells which produces an immunologically homogeneous protein commonly referred to as a paraprotein or monoclonal protein (M-protein, where the "M" stands for monoclonal). Each serum M-protein consists of two heavy polypeptide chains of the same class designated by a capital letter and a corresponding Greek letters: Gamma (γ) in IgG, Alpha (α) in IgA, Mu (μ) in IgM, Delta (δ) in IgD, Epsilon (ε) in IgE. Basophils in IgE myeloma are characterized by a higher expression of high affinity IgE receptor relative to normal controls.

White Blood Cells

White blood cells ("leukocytes", "WBCs") are cells of the immune system that defend the human body against infectious disease and foreign materials. The name "white blood cell" derives from the fact that after centrifugation of a blood sample, the white cells are found in a thin, typically white layer ("buffy coat") of nucleated cells between the pelleted red blood cells and the blood plasma.

The several different types of WBCs, including neutrophils, eosinophils, basophils, lymphocytes, monocytes, macrophages and dendritic cells, often divided into two subgroups, granulocytes or agranulocytes, based on their appearance by light microscopy.

1. Granulocytes

Granulocytes (polymorphonuclear leukocytes) are leukocytes characterized by the presence of differently staining granules in their cytoplasm when viewed under light microscopy. These granules are membrane-bound enzymes that act primarily in the digestion of endocytosed particles. Granulocytes include basophils, eosinophils and neutrophils.

Basophils

Basophilic granulocytes (basophils) are a small population of peripheral blood leukocytes containing cytoplasmic granules that stain with basophilic (staining readily with a basic dye) dyes. Based on their similar morphology to mast cells, basophils have often been considered (and neglected) as minor and possibly redundant "circulating mast cells." It has been very difficult for most laboratories to obtain basophils without major contaminating populations, because the percentage of basophils in peripheral blood is low (<1%) and they share physiochemical properties with other blood cells. This lack of satisfactory purification protocols has considerably hampered basophil research and negatively affected the interest in this cell type.

Basophils contain prominent cytoplasmic granules, are major sources of histamine (a vasodilator) and other potent chemical mediators of inflammation, and constitutively express Fc epsilon receptor (FceRI), the high affinity IgE receptor. They typically exhibit a segmented nucleus with marked condensation of nuclear chromatin. As with all granulocytes, basophils develop in the bone marrow, and are released as fully mature cells with a survival span estimated to be 2-3 days.

Basophils express a variety of seven membrane transverse receptors that bind chemotactic factors. Most are members of the CCR family of receptors that bind CC (or the β-family) chemokines. Among those with overlapping binding (predominantly to CCR3) are members of the monocyte chemotactic protein (MCP) family, including MCP-1 (CCL2), MCP-3 (CCL7), MCP-4 (CCL13), RANTES (CCL5), MIP-1α (CCL3), eotaxin-1 (CCL11), and eotaxin-2 (CLL24). Further, basophils have receptors for stromal cell-derived factor (SDF-1; CXCL12), a strongly chemotactic molecule for lymphocytes that is a member of the CXC family that binds to CXCR-4; a receptor with a wide cellular distribution, expressed on the surface of most immature and mature hematopoietic cells types such as, for example, neutrophils, monocytes, T and B cells, dendritic cells, Langerhans cells, and macrophages.

Human basophils also express several cytokine receptors. Among these are receptors that bind to specific interleukins including IL-2, IL-3, IL-4, IL-5, and IL-33. Only IL-3 and IL-33 are thought to mediate significant functional responses. Basophils are but one of two cell types in blood (the other being plasmacytoid dendritic cells (pDCs)) that express IL-3 receptors (CD123) at exceedingly high levels. Although the exact number of receptors remains unknown, studies indicate the expression levels of IL-3 are nearly 2-fold higher than any other cell type. This characteristic has led to use of CD123 expression as a marker to specifically gate on basophils (and pDCs) during flow cytometry analysis.

The high affinity IgE receptor (FcεRI) is thought to be the single most significant activation-linked molecule known on basophils. These receptors are comprised of four subunits: one α, one β, and 2γ chains that form a tetramer structure (αβγ2). Two extracellular domains on the α-subunit allow IgE binding, whereas signaling events are initiated through immunoreceptor tyrosine-based activation motifs (ITAMs) located within intracellular portions of the β-subunits and γ-subunits. In humans, a trimeric form of FcεRI, which lacks the β-subunit ($αγ_2$), also is found on antigen-presenting cells (APCs), including Langerhans cells, monocytes and blood dendritic cells. Mast cells, eosinophils, neutrophils, platelets and dendritic cells also may have these and/or functionally related receptors.

Basophils can infiltrate sites of many immunologic or inflammatory processes, including IgE-associated late-phase reactions and sites of chronic allergic inflammation, often in association with eosinophils. Further, basophils can be involved in IgE independent mechanisms.

Basophils release several inflammatory mediators that have a role in the pathophysiology of allergic disease. The most commonly recognized inflammatory mediators are histamine and leukotriene C4 (LTC4), which cause smooth muscle contraction. It long has been thought, but not proved, that basophils release these substances during and/or after selectively infiltrating sites of allergic inflammation and thus contribute towards the symptoms of the "late phase response" (LPR). Basophils circulate in the blood under homeostatic conditions but will migrate into tissue during the LPR, which often follows acute allergic reactions. The exact mechanism of how they achieve this is not fully understood, in part due to the limited number of basophil studies that have resulted due to a lack of protocols to separate basophils from other effector cell populations.

Human basophils also release several other substances that are believed to possess inflammatory properties, although their exact role in allergic inflammation remains unclear. For example, basogranulin (which is defined by the monoclonal antibody BB1), a granule-specific highly basic protein secreted as a large complex (approximately $5 \times 10^6$ Da) by basophils, is secreted in vitro under the same conditions important for histamine release, including those occurring with both IgE-dependent and IgE-independent stimulation. Further, basophils also are believed to synthesize and secrete granzyme B (a serine protease).

In humans, basophils appear to be the prime early producers of the Th2-type cytokines IL-4 and IL-13, which perform several crucial functions in initiating and maintaining allergic responses. This putative immunomodulatory role of basophils is supported further by their ability to express CD40 ligand, which, together with IL-4 and IL-13, serve as inducers of B cell proliferation and class switching to IgE and IgG4. Moreover, human basophils are the main cellular source for rapid IL-4 generation, a mandatory requirement for the development of Th2 responses. Staining techniques have localized basophils in various tissues affected by allergic diseases. Some studies suggest that the interaction of basophils, T cells and B cells at these sites propagate pro-allergic immune responses. Additionally, basophil activation is not restricted to antigen-specific IgE crosslinking but can be caused in non-sensitized individuals by parasitic antigens, plant lectins and viral superantigens binding to non-specific IgEs. The presence of novel IgE-independent receptor targets that cause trafficking and Th2 cytokine release from basophils further underlines their potential role in innate as well as adaptive immunity.

Eosinophils

Eosinophils are primarily tissue-dwelling granulocytes that are recruited to sites of acute inflammation, and are seen most prominently in response to respiratory, gastrointestinal, and dermatologic allergens, as well as to generalized infection with helminthic parasites. Traditionally, functions of eosinophils focused singularly on their roles as end-stage "effector" cells, for example, in releasing their four granule cationic proteins and generating paracrine mediators of inflammation (such as ei-cosanoids). Studies have focused on eosinophils based in part on the recognition that eosinophils have distinct innate capacities to secrete differentially multiple preformed cytokines. Eosinophil-associated allergic inflammatory diseases notably occur in the airways and include nasal polyposis, allergic rhinoconjunctivitis and asthma. Eosinophils recruited into the mucosal airway tissues and secretions are positioned to encounter aeroallergens where it is thought they may assume a role as an antigen-presenting cell (APC). For example, in humans, blood eosinophils, which normally do not display MHC II proteins, can be induced to do so by stimulation with cytokines, including GM-CSF, IL-3, IL-4, IL-5 and interfereon-γ (IFN-γ). Moreover, human eosinophils recruited into the airways, as evidenced in the sputum of asthmatics and in lung lavages after allergen challenges, typically express MHC class II proteins. Unlike the gastroinstestinal tract where eosinophils normally are found and might be exposed to gut-derived antigens, eosinophils are not abundant in the normal lungs or airways. In contrast, recruitment of eosinophils into the upper and lower airways is a frequent concomitant of allergic inflammation. It is in this setting of allergic airways diseases that recruited eosinophils might function not simply as effectors of local inflammation, but also as "inflammatory" full-function antigen-presenting cells in processing and presenting airway antigens. In the context of allergic upper and lower airways diseases in which eosinophils are characteristically elicited, the capacity of eosinophils to serve as additional recruited "inflammatory" full-function APCs could be pertinent to antigen-elicited immune responses in the airways of those with often chronic, eosinophilic allergic diseases.

Neutrophils

Neutrophil leukocytes are crucial to both immunity and inflammation, and prolonged neutropenia (a decrease in the presence of neutrophils) leads to inevitable demise as a result of overwhelming infection. Neutrophils normally represent between 40% and 50% of the circulating leukocyte population, and they are easily recognized on a Wright's stained blood smear (a histologic stain that facilitates the differentiation of blood cell types) by their size, their characteristic multilobed nuclei, and the presence of fine stippling (representing granules throughout the cytoplasmic compartment). Primary and secondary granules contain distinct sets of their own proinflammatory mediators.

Neutrophils in the circulation are quiescent cells with only the potential to mediate a wide range of inflammatory activities. This potential is realized when neutrophils are activated. Neutrophils can be activated by a large number of specific agents, including, but not limited to, the following:

| Activating Agent | Function |
| --- | --- |
| leukotriene B4 (LTB4) | a chemoattractant that enhances adherence to endothelial cells and activates degranulation and NADPH oxidase activity |
| complement fragment C5a | chemoattractant that induces degranulation and adherence |
| platelet activating factor (PAF) | induces aggregation, adherence and degranulation |
| histamine | induces concentration-dependent changes in chemotaxis priming and degranulation |
| interferon-γ (IFN-γ) | increases antibody-dependent cytotoxicity and priming |
| granulocyte colony-stimulating factor (G-CSF) | increases antibody-dependent cytotoxicity and priming, and enhances phagocytosis |
| granulocyte-macrophage colony-stimulating factor (GM-CSF) | induces priming and stimulates maturation within the bone marrow |
| IL-8 | chemoattractant that induces degranulation and NADPH oxidase activity |
| tumor necrosis factor-α (TFN-α) | chemoattractant that induces priming, enhances phagocytosis and antibody-dependent cytotoxicity |
| fMet-Leu-Phe | chemoattractant that induces aggregation, degranulation and NADPH oxidase activity |

As a group, these activating agents transmit signals to neutrophils via interaction with specific cell surface receptors, many of which interact with intracellular G proteins. G proteins catalyze the hydrolysis of guanosine triphosphate (GTP) to guanosine diphosphate (GDP) and inorganic phosphate, and initiate a series of events including activation of phospholipase C, initiation of calcium fluxes, and membrane depolarization. Once activated, neutrophils are able to adhere to endothelial cells, migrate through the endothelial barrier, and ingest and at least attempt to destroy pathogens, foreign bodies, and remnants of tissue damage. Neutrophils primed by brief exposure to activating agents (for example, but not limited to, endotoxin, IL-1, fMet-Leu-Phe, and GM-CSF) exhibit an enhanced response to subsequent stimuli. Both short-term (including changes in cell shape, oxidative and phagocytic capacity) and long-term (prolonged cell viability) responses to priming agents have been observed.

Neutrophils contain both primary and secondary granules each with distinct effector proteins. Major components of primary granules (azurophil) include myeloperoxidase (which converts hydrogen peroxide generated by NADPH oxidase and hydrochloric acid to hypochlorous acid), defensins (having antibacterial activity), bacterial permeability-increasing protein (BPI; having antibacterial activity), cathepsin G (antibacterial activity), lysozyme (which digests the peptidoglycan component of most bacterial cell walls), elastase, alkaline phosphatase, proteinase 3, β-glucuronidase, phospholipases A2, C and D, and α-mamosidase. The major secondary components include lactoferrin (an iron-binding protein with some antibacterial activity), gelatinase, collagenase, vitamin B12-binding protein, lysozyme, cytochrome b558, fMLP receptor, integrins (CD11b/CD18, CD11c/CD18), complement receptor 3 (CR3), histaminase, and plasminogen activator.

2. Agranulocytes

Agranulocytes (mononuclear leukocytes) are characterized by the apparent absence of granules in their cytoplasm. These cells contain azurophilic granules, which are lysosomes. Agranulocytes include lymphocytes, monocytes and macrophages.

Isolating Blood Granulocyte Responses

Subsets of granulocytes can be isolated from blood by a variety of physical techniques, such as, for example, density gradient centrifugation. Magnetic particles associated with monoclonal antibodies can be specifically bound to subsets of granulocytes and "stuck" temporarily to magnetic material to "positively isolate" the subsets. Alternatively, contaminating subsets can be removed by binding magnetic beads to them. However, in all cases, the manipulations and time constraints inherent in physical separation methods may initiate non-specific activation of the granulocytes. This has been demonstrated to occur even with very short and relatively gentle manipulations.

The activation of the granulocytes during these isolation procedures, which also can include flow cytometry cell sorting methods, is demonstrable by the appearance of CD11b, CD63, CD203, CD66b and other activation markers on the various granulocyte subpopulations. The presence of these markers is detectable by flow cytometry analysis of the isolated subpopulations.

Flow Cytometry

Flow cytometry, a technique that may be used for counting and examining cells, allows simultaneous multiparametric analysis of the physical and/or chemical characteristics of each individual cell. Briefly, a beam of light (usually laser light) of a single wavelength is directed onto a hydrodynamically-focused stream of fluid. A number of detectors are aimed at the point where the stream passes through the light beam: one in line with the light beam (Forward Scatter (FSC)), several perpendicular to it (Side Scatter (SSC)), and one or more fluorescence detectors. Each suspended cell (from 0.2 µm to 150 µm) passing through the light beam scatters the light in some way, and fluorescent molecules (naturally occurring or as part of an attached label or dye) may be excited into emitting light at a longer wavelength than the light source. This combination of scattered and fluorescent light is recorded by the detectors. The FSC correlates with the cell volume; SSC depends upon the inner complexity of the cell (i.e., shape of the nucleus, type of cytoplasmic granules, etc.). The data generated by flow cytometers may be plotted as a histogram. The regions on these plots can be separated sequentially based on fluorescence intensity by creating a series of subset extractions ("gates"). Specific gating protocols have been developed for diagnostic and clinical purposes.

Fluorescence activated cell sorting (FACS) provides a method of sorting a heterogeneous mixture of cells into two or more containers, a single cell at a time, based upon the specific light scattering and fluorescent characteristics of each cell. Briefly, the cell suspension is entrained in the center of a narrow, rapidly flowing stream of liquid and the flow is arranged such that there is a large separation between cells relative to their diameter. The stream of individual cells passes through a fluorescence detector, and an electrical charge is assigned to each cell (based on the cell's fluorescence) just as the stream is broken into individual drops (usually via vibration) such that there is a low probability of more than one cell per droplet. Each charged droplet (containing an individual cell) may be sorted, via electrostatic deflection, into separate containers.

The surfaces of all cells in the body are coated with specialized protein receptors that selectively can bind or adhere to other signaling molecules. These receptors and the molecules that bind to them are used for communicating with other cells and for carrying out proper cell functions in the body. Each cell type has a certain combination of receptors (or surface markers) on its surface that makes it distinguishable from other kinds of cells. Cells may be fluorescently labeled, i.e., a reactive derivative of a fluorophore may be covalently attached to a cell. The most commonly used labeled molecules are antibodies; their specificity towards certain surface markers on a cell surface allows for more precise detection and monitoring of particular cells. The fluorescence labels that can be used will depend upon the lamp or laser used to excite the fluorochromes and on the detectors available. For example, when a blue argon laser (448 nm) is used, fluorescent labels used may include, but are not limited to, fluorescein isothiocyanate (FITC), Alexa Fluor® 488, green fluorescent protein (GFP), carboxyfluorescein (CFSE), carboxyfluorescein diacetate succinimidyl ester (CFDA-SE), DyLight® 488 (Dyomics), phycoerythrin (PE), propidium iodide (PI), peridinin chlorophyll protein (PerCP), PerCP-Cy™ 5.5, PE-AlexaFluor 700, PE-Cy™ 5; PE-Cy™ 5.5, PE-AlexaFluor® 750 and PE-Cy™ 7; when a red diode laser (635 nm) is used, fluorescent labels used may include, but are not limited to, allophycocyanin (APC), APC-Cy™ 7, APC-eFluor® 780, AlexFluor® 700, Cy™ 5, and Draq-5; when a violet laser is used (405 nm), fluorescent labels may include, but are not limited to, Pacific Orange™, amine aqua, Pacific Blue™, 4'-6-diamidino-2-phenylindole (DAPI), AlexFluor® 405, and eFluor® 450.

The development of flow-cytometry based approaches to the identification of activation markers and intracellular markers, via measurement of enzymatic and surface marker profiles, has allowed for accelerated association of surface topologies with disease states. Studies that involve the triggering of cells to respond to environmental stimuli, such as an allergen or drug action, and the activation phenotypes associated with such agitation, allow for clearer resolution of the underlying activation states and provide for more distinct classification of allergic disease outcomes. Allergy is a dynamic event, and as such, static views of basal states would be considered insufficient for determination of an activated state, therefore rendering correlations to clinical outcomes less meaningful. Fractionation of cell populations with flow cytometry is well suited to address activation markers and intracellular markers in the context of allergic diseases, because it can simultaneously discern multiple surface markers within complex cellular populations.

Cluster of Differentiation

The cluster of differentiation (CD) system is a protocol used for the identification of cell surface molecules present on white blood cells. CD molecules can act in numerous ways, often acting as receptors or ligands; by which a signal cascade is initiated, altering the behavior of the cell. Some CD proteins do not play a role in cell signaling, but have other functions, such as cell adhesion. Generally, a proposed surface molecule is assigned a CD number once two specific monoclonal antibodies (mAb) are shown to bind to the molecule. If the molecule has not been well-characterized, or has only one mAb, the molecule usually is given the provisional indicator "w."

The CD system nomenclature commonly used to identify cell markers thus allows cells to be defined based on what molecules are present on their surface. These markers often are used to associate cells with certain immune functions. While using one CD molecule to define populations is uncommon, combining markers has allowed for cell types with very specific definitions within the immune system. There are more than 350 CD molecules identified for humans.

CD molecules are utilized in cell sorting using various methods, including flow cytometry. Cell populations usually are defined using a "+" or a "−" symbol to indicate whether a certain cell fraction expresses or lacks a CD molecule. For example, a "CD34+, CD31−" cell is one that expresses CD34, but not CD31. Table 1 shows commonly used markers employed by skilled artisans to identify and characterize differentiated white blood cell types:

| Type of Cell | CD Markers |
| --- | --- |
| Stem cells | CD34+, CD31− |
| All leukocyte groups | CD45+ |
| Granulocyte | CD45+, CD15+ |
| Monocyte | CD45+, CD14+ |
| T lymphocyte | CD45+, CD3+ |
| T helper cell | CD45+, CD3+, CD4+ |
| Cytotoxic T cell | CD45+, CD3+, CD8+ |
| B lymphocyte | CD45+, CD19+ or CD45+, CD20+ |
| Thrombocyte | CD45+, CD61+ |
| Natural killer cell | CD16+, CD56+, CD3− |

CD molecules used in defining leukocytes are not exclusively markers on the cell surface. Most CD molecules have an important function, although only a small portion of known CD molecules have been characterized. For example, there are over 350 CD for humans identified thus far.

CD3 (TCR complex) is a protein complex composed of four distinct chains. In mammals, the complex contains a CD3γ chain, a CD3δ chain, and two CD3ε chains, which associate with the T cell receptor (TCR) and the ζ-chain to generate an activation signal in T lymphocytes. Together, the TCR, the ζ-chain and CD3 molecules comprise the TCR complex. The intracellular tails of CD3 molecules contain a conserved motiff known as the immunoreceptor tyrosine-based activation motif (ITAM), which is essential for the signaling capacity of the TCR. Upon phosphorylation of the ITAM, the CD3 chain can bind ZAP70 (zeta associated protein), a kinase involved in the signaling cascade of the T cell.

CD14 is a cell surface protein expressed mainly by macrophages and, to a lesser extent, neutrophil granulocytes. CD14+ cells are monocytes that can differentiate into a host of different cells; for example, differentiation to dendritic cells is promoted by cytokines such as GM-CSF and IL-4. CD14 acts as a co-receptor (along with toll-like receptor (TLR) 4 and lymphocyte antigen 96 (MD-2)) for the detection of bacterial lipopolysaccharide (LPS). CD14 only can bind LPS in the presence of lipopolysaccharide binding protein (LBP).

CD15 (3-fucosyl-N-acetyl-lactosamine; stage specific embryonic antigen 1 (S SEA-1)) is a carbohydrate adhesion molecule that can be expressed on glycoproteins, glycolipids and proteoglycans. CD15 commonly is found on neutrophils and mediates phagocytosis and chemotaxis.

CD16 is an Fc receptor (FcγRIIIa and FcγRIIIb) found on the surface of natural killer cells, neutrophil polymorphonuclear leukocytes, monocytes and macrophages. Fc receptors bind to the Fc portion of IgG antibodies.

CD19 is a human protein expressed on follicular dendritic cells and B cells. This cell surface molecule assembles with the antigen receptor of B lymphocytes in order to decrease the threshold for antigen receptor-dependent stimulation. It generally is believed that, upon activation, the cytoplasmic tail of CD19 becomes phosphorylated, which allows binding by Src-family kinases and recruitment of phosphoinositide 3 (PI-3) kinases.

CD20 is a non-glycosylated phosphoprotein expressed on the surface of all mature B-cells. Studies suggest that CD20 plays a role in the development and differentiation of B-cells into plasma cells. CD20 is encoded by a member of the membrane-spanning 4A gene family (MS4A). Members of this protein family are characterized by common structural features and display unique expression patterns among hematopoietic cells and nonlymphoid tissues.

CD31 (platelet/endothelial cell adhesion molecule; PECAM1) normally is found on endothelial cells, platelets, macrophages and Kupffer cells, granulocytes, T cells, natural killer cells, lymphocytes, megakaryocytes, osteoclasts and neutrophils CD31 has a key role in tissue regeneration and in safely removing neutrophils from the body. Upon contact, the CD31 molecules of macrophages and neutrophils are used to communicate the health status of the neutrophil to the macrophage.

CD34 is a monomeric cell surface glycoprotein normally found on hematopoietic cells, endothelial progenitor cells, endothelial cells of blood vessels, and mast cells. The CD34 protein is a member of a family of single-pass transmembrane sialomucin proteins and functions as a cell-cell adhesion factor. Studies suggest that CD34 also may mediate the attachment of stem cells to bone marrow extracellular matrix or directly to stromal cells.

CD45 (protein tyrosine phosphatase, receptor type, C; PTPRC) cell surface molecule is expressed specifically in hematopoietic cells. CD45 is a protein tyrosine phosphatase (PTP) with an extracellular domain, a single transmembrane segment, and two tandem intracytoplasmic catalytic domains, and thus belongs to receptor type PTP. Studies suggest it is an essential regulator of T-cell and B-cell antigen receptor signaling that functions by direct interaction with components of the antigen receptor complexes, or by activating various Src family kinases required for antigen receptor signaling. CD45 also suppresses JAK kinases, and thus functions as a regulator of cytokine receptor signaling. The CD45 family consists of multiple members that are all products of a single complex gene. Various known isoforms of CD45 include: CD45RA, CD45RB, CD45RC, CD45RAB, CD45RAC, CD45RBC, CD45RO, and CD45R (ABC). Different isoforms may be found on different cells. For example, CD45RA is found on naïve T cells and CD45RO is found on memory T cells.

CD56 (neural cell adhesion molecule, NCAM) is a homophilic binding glycoprotein expressed on the surface of neurons, glia, skeletal muscle and natural killer cells. It generally is believed that NCAM has a role in cell-cell adhesion, neurite outgrowth, and synaptic plasticity. There are three known main isoforms of NCAM, each varying only in their cytoplasmic domains: NCAM-120 kDA (glycosyl-phopharidylinositol (GPI) anchored); NCAM-140 kDa (short cytoplasmic domain); and NCAM (long cytoplasmic domain). The different domains of NCAM have different roles, with the Ig domains being involved in homophilic binding to NCAM, and the fibronection type III (FNIII) domains being involved in signaling leading to neurite outgrowth.

CD66b ((CGM1); CD67, CGM6, NCA-95) is a glycosyl-phosphatidylinositol (GPI)-linked protein that is a member of the immunoglobulin superfamily and carcinoembryonic antigen (CEA)-like subfamily. CD66b, expressed on granulocytes, generally is believed to be involved in regulating adhesion and activation of human eosinophils.

Human leukocyte antigen (HLA)-DR is a major histocompatibility complex (MHC) class II cell surface receptor. HLA-DR commonly is found on antigen-presenting cells such as macrophages, B-cells, and dendritic cells. This cell surface molecule is a αβ heterodimer with each subunit containing 2 extracellular domains: a membrane spanning domain and a cytoplasmic tail. Both the α a and β chains are anchored in the membrane. The complex of HLA-DR and its ligand (a peptide of at least 9 amino acids) constitutes a ligand for the TCR.

Integrins are receptors that mediate attachment between a cell and the tissues surrounding it and are involved in cell-cell and cell-matrix interactions. In mammals, 18α and 8β subunits have been characterized. Both α and β subunits contain two separate tails, both of which penetrate the plasma membrane and possess small cytoplasmic domains.

Integrin αM (ITGAM; CD11b; macrophage-1 antigen (Mac-1); complement receptor 3 (CR3)) is a protein subunit of the heterodimeric integrin $\alpha_M\beta_2$ molecule. The second chain of $\alpha_M\beta_2$ is the common integrin $\beta_2$ subunit (CD18). $\alpha_M\beta_2$ is expressed on the surface of many leukocytes including monocytes, granulocytes, macrophages and natural killer cells. It generally is believed that $\alpha_M\beta_2$ mediates inflammation by regulating leukocyte adhesion and migration. Further, $\alpha_M\beta_2$ is thought to have a role in phagocytosis, cell-mediated cytotoxicity, chemotaxis and cellular activation, as well as being involved in the complement system due to its capacity to bind inactivated complement component 3b (iC3b). The ITGAM subunit of integrin $\alpha_M\beta_2$ is involved directly in causing the adhesion and spreading of cells, but cannot mediate cellular migration without the presence of the $\beta_2$ (CD18) subunit.

CD61 (integrin β3; platelet glycoprotein IIIa; ITGB3) is a cell surface protein composed of an α-chain and a β-chain. A given chain may combine with multiple partners resulting in different integrins. CD61 is found along with the α IIb chain in platelets and is known to participate in cell adhesion and cell-surface mediated signaling.

CD63 (LAMP-3; ME491; MLA1; OMA81H) is a cell surface glycoprotein of the transmembrane 4 superfamily (tetraspanin family). Many of these cell surface receptors have four hydrophobic domains and mediate signal transduction events that play a role in the regulation of cell development, activation, growth and motility. CD63 forms complexes with integrins and may function as a blood platelet activation marker. It generally is believed that the sensitivity and specificity of measuring the upregulation of CD63 alone, or as part of a combination, is not specific enough to serve as a diagnostic marker for the diagnosis of IgE mediated allergy.

CD123 is the 70 kD transmembrane a chain of the cytokine interleukin-3 (IL-3) receptor. Alone, CD123 binds IL-3 with low affinity; when CD123 associates with CDw131 (common β chain), it binds IL-3 with high affinity. CD123 does not transduce intracellular signals upon binding IL-3 and requires the β chain for this function. CD123 is expressed by myeloid precursors, macrophages, dendritic cells, mast cells, basophils, megakaryocytes, and some B cells CD123 induces tyrosine phosphorylation within the cell and promotes proliferation and differentiation within the hematopoietic cell lines.

CD203c (ectonucleotide pyrophosphatase/phosphodiesterase 3; ENPP3) is an ectoenzyme constitutively and specifically expressed on the cell surface and within intracellular compartments of basophils, mast cells, and precursors of these cells. CD203c detection by flow cytometry has been used to specifically identify basophils within a mixed leukocyte suspension, since its expression is unique to basophils among the cells circulating in blood. The expression of CD203c is both rapidly and markedly upregulated following IgE-dependent activation. However, as with CD63, it is generally believed that the sensitivity and specificity of measuring the upregulation of CD203c alone, or as part of a combination, is not specific enough to serve as a diagnostic marker for the diagnosis of IgE mediated allergy. Further, the exact role of CD203c in basophil biology is unknown.

CD294 (G protein-coupled receptor 44; GPR44; CRTh2; DP2) is an integral membrane protein. This chemoattractant receptor homologous molecule is expressed on T helper type-2 cells. The transmembrane domains of these proteins mediate signals to the interior of the cell by activation of heterotrimeric G proteins that in turn activate various effector proteins that ultimately result a physiologic response.

Need for Methodologies and Assays

The analysis of subpopulations of white blood cells remains of particular interest for the evaluation of immune system disorders, especially allergic diseases. Basophils and eosinophils, both important components of the allergic response, and the activation phenotypes they display during a response to an environmental stimuli, provide an important focus of study of allergy treatment, detection and classification.

Many conventional approaches of monitoring cell activation make use of potentially biased extended in vitro-cultured cells. Further, many conventional methods of counting white blood cells, such as basophils and eosinophils, are based on granule-staining with subsequent manual or automated counting. These methods are time consuming and lack specificity towards cell activation and distinguishing between live cells and dead cells. Conventional purification kits remain based on density gradient separation followed by cell sorting; these methods typically fail to provide pure cell samples and eliminate contamination.

Further, many assays for allergy to foods have disadvantages. Blood tests for specific immunoglobulin levels lack high specificity while the "gold standard" for identifying a food allergen to which a patient is allergic is a costly, double-blind, placebo-controlled in vivo food challenge (DBPCFC). The DBPFC requires an often lengthy hospitalization and places the patient at risk for induction of anaphylaxis, as these skin tests may be associated with anaphylaxis. These safety concerns impair the ability to identify offending allergens. Furthermore, clinical studies on food allergy are difficult to conduct given the need for skin tests and DBPCFC. Many assays designed to aid in the diagnosis of food allergy are technically complex, lack adequate sensitivity, are non-specific and require prolonged time periods.

The described invention addresses the inadequacies of these methods. It provides the ability to monitor cell activation in patient samples such as whole blood, more specifically white blood cells such as basophils and eosinophils, therein, and allows for measuring activation ex vivo. Further, it allows for physiologic interpretations in situations, for instance, where immune action depends on natural context, for close monitoring of activation states within patients who have an allergic disease, and for correlation of disease state and treatment. Additionally, the described invention provides a method of isolating basophils from stimulated or unstimulated blood based that is independent of the IgE/High affinity IgE receptor on the basophil cell surface.

SUMMARY OF THE INVENTION

The described invention relates to methods for detecting nonactivated basophils in a whole blood sample obtained from a normal healthy subject, methods for determining susceptibility to an allergic reaction to an allergen of a subject with no known allergy to the antigen, methods for measuring a response to challenge with a potential allergen in a whole blood sample obtained from a subject with known allergic reactivity to allergens other than the potential allergen; and to an in vitro system for reliable detection or quantification of a specific white blood cell population in a whole blood sample.

In one aspect, the described invention provides a method for detecting nonactivated basophils in a whole blood sample obtained from a normal healthy subject, the method comprising the steps: (a) collecting a whole blood sample from the subject; wherein the whole blood sample comprises white blood cells, wherein the white blood cells comprise at least one cell population selected from the group of (i) a basophil population comprising at least one nonactivated basophil and (ii) an eosinophil population comprising at least one nonactivated eosinophil; wherein the nonactivated basophil in the basophil cell population expresses at least one cell surface marker characteristic of the at least one nonactivated basophil; and wherein the eosinophil population expresses at least one cell surface marker characteristic of the at least one nonactivated eosinophil; (b) fractionating the whole blood sample by flow cytometry to separate the basophil population from the eosinophil population; (c) specifically detecting a nonactivated basophil in the basophil cell population; and (d) optionally specifically detecting a nonactivated eosinophil in the eosinophil cell population. According to one embodiment of the method, the at least one nonactivated basophil in the basophil population further expresses at least one intracellular marker characteristic of the at least one nonactivated basophil. According to another embodiment, a level of expression of the intracellular marker specifically correlates to a level of expression of the at least one cell surface marker characteristic of the at least one nonactivated basophil. According to another embodiment, collecting step (a) is by ventipuncture. According to another embodiment, the whole blood sample of step (a) is of a volume of about 5 µl to about 500 µl. According to another embodiment, the method further comprises the step of labeling the whole blood sample of step (a) with at least one differential label to identify a specific population of cells. According to another embodiment, the specific population of cells is a specific population of basophils. According to another embodiment, the specific population of cells is a specific population of eosinophils. According to another embodiment, the at least one differential label is at least one differential stain. According to another embodiment, the at least one differential label is at least one antibody. According to another embodiment, the at least one antibody is at least one fluorescently-labeled antibody. According to another embodiment, the at least one fluorescently-labeled antibody is at least one fluorescently-labeled antibody selected from the group consisting of an antibody against cell surface marker CD3 (TCR) complex, an antibody against cell surface marker CD16, an antibody against cell surface marker CD19, an antibody against cell surface marker CD56, an antibody against cell surface marker CD66b, an antibody against cell surface marker HIA-DR, an antibody against cell surface marker CD20, an antibody against cell surface marker CD123, an antibody against cell surface marker CD11b, an antibody against cell surface marker CD63, an antibody against cell surface marker CD203c, an antibody against cell surface marker CD294, an antibody against cell surface marker CD4, and an antibody against cell surface marker CD14. According to another embodiment, fractionating step (b) further comprises the step utilizing a gating strategy to identify basophils, the gating strategy comprising the steps: 1) excluding doublets based on forward scatter area versus height; 2) selecting leukocytes based on forward and side scatter; 3) excluding dead cells using a fixable dead cell stain (LIVE/DEAD® InfraRed).; and 4) selecting the basophil population as a CD3−/CD16−/CD20−/CD56−/CD66b−IHLA-DR− and CD294+ population. According to another embodiment, fractionating step (b) further comprises the step utilizing a gating strategy to identify basophils, the gating strategy comprising the steps: 1) gating basophils based on scatter properties; 2) gating natural killer cells based on a level of expression of cell surface marker CD56; 3) gating B and T cells based on a level of expression of cell surface marker CD19 and a level of expression of cell surface marker CD4; 4) gating monocytes based on a level of expression of cell surface marker CD11b; and 5) gating basophils based on a level of expression of cell surface marker CD203c and a level of expression of cell surface marker CD294. According to another embodiment, fractionating step (b) further comprises the step utilizing a gating strategy to identify basophils, the gating strategy further comprising the step of gating basophils based on a level of expression of cell surface marker CD203c and a level of expression of cell surface marker CD63. According to another embodiment, the level of expression of cell surface marker CD63 is correlated to the level of expression of cell surface marker CD203c. According to another embodiment, wherein the level of expression of CD203c measured is at least about 8-fold higher than the level of expression of CD63. According to another embodiment, the intracellular marker is at least one intracellular marker selected from the group consisting of a cytokine, a transcription factor, a phosphoprotein, a histamine, and a leukotriene. According to another embodiment, a level of expression of the at least one intracellular marker correlates to a level of expression of the at least one cell surface marker.

According to another aspect, the described invention provides an ex vivo method for determining a subject's susceptibility to an allergic reaction, wherein the subject has no known allergy to the allergen, the method comprising the steps: (a) collecting a whole blood sample from the subject, wherein the whole blood sample comprises white blood cells, wherein the white blood cells comprise at least one cell population selected from the group of (i) a basophil population comprising at least one activatable basophil and (ii) an eosinophil population comprising at least one activatable eosinophil; wherein the basophil cell population expresses at least one cell surface marker characteristic of the at least one activatable basophil; and wherein the eosinophil cell population expresses at least one cell surface marker characteristic of the at least one activatable eosinophil; (b) fractionating the whole blood sample by flow cytometry to separate the basophil population from the eosinophil population; and (c) correlating a level of expression of the at least one surface marker characteristic of the at least one activatable basophil, relative to a background level of expression of the at least one surface marker that is characteristic of a nonactivated basophil, to susceptibility of the subject to an allergic reaction to the allergen. According to one embodiment of the method, the at least one activatable basophil in the basophil population further expresses at least one intracellular marker characteristic of the at least one activatable basophil. According to another embodiment, the level of expression of the at least one intracellular marker characteristic of the at least one activatable basophil specifically correlates to the level of expression of the at least one cell surface marker characteristic of the at least one activatable basophil. According to another embodiment, collecting step (a) is by venipuncture. According to another embodiment, the whole blood sample of step (a) is of a volume of about 5 μl to about 500 μl. According to another embodiment, the allergen is selected from the group consisting of a food allergen, a peanut allergen, a cashew allergen, an apple allergen, a milk allergen, an environmental allergen, a cockroach allergen, a tree pollen allergen, a grass allergen, a mold allergen, a hay allergen, and a drug allergen. According to another embodiment, step (a) further comprises the step of labeling white blood cells in the whole blood sample with at least one differential label. According to another embodiment, the at least one differential label is at least one differential stain. According to another embodiment, the at least one differential label is at least one antibody. According to another embodiment, the at least one antibody is at least one fluorescently-labeled antibody. According to another embodiment, the at least one antibody is at least one antibody selected from the group consisting of an antibody against cell surface marker CD3 (TCR) complex, an antibody against cell surface marker CD16, an antibody against cell surface marker CD19, an antibody against cell surface marker CD56, an antibody against cell surface marker CD66b, an antibody against cell surface marker HIA-DR, an antibody against cell surface marker CD20, an antibody against cell surface marker CD123, an antibody against cell surface marker CD11b, an antibody against cell surface marker CD63, an antibody against cell surface marker CD203c, an antibody against cell surface marker CD294, an antibody against cell surface marker CD4, and an antibody against cell surface marker CD14. According to another embodiment, fractionating step (b) further comprises the step utilizing a gating strategy to identify basophils, the gating strategy comprising the steps: 1) excluding doublets based on forward scatter area versus height; 2) selecting leukocytes based on forward and side scatter; 3) excluding dead cells using a fixable dead cell stain (LIVE/DEAD® Near InfraRed); and 4) selecting the basophil population as a CD3−/CD16−/CD20−/CD56−/CD66b−IHLA-DR− and CD294+ population. According to another embodiment, fractionating step (b) further comprises the step: utilizing a gating strategy to identify basophils, the gating strategy comprising the steps: 1) gating basophils based on scatter properties; 2) gating natural killer cells based on expression of cell surface marker CD56; 3) gating BandT cells based on a level of expression of cell surface marker CD19 and a level of expression of cell surface marker CD4; 4) gating monocytes based on a level of expression of cell surface marker CD11b; and 5) gating basophils based on a level of expression of cell surface marker CD203c and a level of expression of cell surface marker CD294. According to another embodiment, fractionating step (b) further comprises the step utilizing a gating strategy to identify basophils, the gating strategy further comprising the step of gating basophils based on a level of expression of cell surface marker CD203c and a level of expression of cell surface marker CD63. According to another embodiment, the level of expression of cell surface marker CD63 correlates to the level of expression of cell surface marker CD203c relative to a background level of expression of cell surface marker CD63 and of cell surface marker CD203. According to another embodiment, the level of expression of cell surface marker CD203c measured is at least about 8-fold higher than the level of expression of cell surface marker CD63. According to another embodiment, the surface marker characteristic of the at least one basophil of step (c) is at least one activation marker selected from the group consisting of cell surface marker CD3, cell surface marker CD16, cell surface marker CD19, cell surface marker CD56, cell surface marker CD66b, cell surface marker HLA-DR, cell surface marker CD11b, cell surface marker CD63, cell surface marker CD123, cell surface marker CD203c and cell surface marker CD294. According to another embodiment, the intracellular marker characteristic of the at least one activatable basophil is at least one intracellular marker selected from the group consisting of a cytokine, a transcription factor, a phosphoprotein, a histamine, and a leukotriene. According to another embodiment, the level of expression of the at least one intracellular marker correlates to the level of expression of the at least one cell surface marker relative to a background level of expression of the at least one intracellular marker and the at least one cell surface marker.

According to another aspect, the described invention provides an ex vivo method for measuring a response to challenge with a potential allergen in a whole blood sample obtained from a subject with known allergic reactivity to allergens other than the potential allergen, the method comprising the steps: (a) collecting a whole blood sample from the subject, wherein the whole blood sample comprises white blood cells, wherein the white blood cells comprise at least one activatable cell population selected from the group of (i) a basophil population comprising at least one activatable basophil and (ii) an eosinophil population comprising at least one eosinophil, wherein the basophil cell population expresses at least one cell surface marker characteristic of the at least one activatable basophil, and wherein the eosinophil cell population expresses at least one cell surface marker characteristic of the at least one activatable eosinophil; (b) contacting the white blood cells in the whole blood sample of step (a) with at least one allergen, thereby activating the at least one activatable cell population to form an activated cell population; (c) fractionating the whole blood sample by flow cytometry to separate the activated basophil population from the activated eosinophil population; (c) correlating a level of expression of the at least one surface marker characteristic of an at least one activated basophil, relative to a background level of expression of the at least one surface marker that is characteristic of a nonactivated basophil, to activation of the basophil population by the allergen; and (d) identifying the allergen as one to which the subject is allergic. According to one embodiment, the at least one activated basophil in the basophil population further expresses at least one intracellular marker characteristic of the at least one activated basophil. According to another embodiment, the intracellular marker characteristic of the at least one activated basophil is at least one intracellular marker selected from the group consisting of a cytokine, a transcription factor, a phosphoprotein, a histamine, and a leukotriene. According to another embodiment, a level of expression of the at least one intracellular marker characteristic of the at least one activated basophil correlates to the level of expression of the at least one cell surface marker characteristic of the at least one activated basophil. According to another embodiment, the level of expression of the at least one intracellular marker characteristic of the at least one activated basophil specifically correlates to the level of expression of the at least one cell surface marker characteristic of the at least one basophil. According to another embodiment, the whole blood sample of step (a) is of a volume of about 5 μl to about 500 μl. According to another embodiment, the method further comprises the step of optionally contacting the white blood cells in the whole blood sample of step (a) with at least one second agent ex vivo. According to another embodiment, the at least one allergen is selected from the group consisting of a nut allergen, a food allergen, an apple allergen, a milk allergen, an environmental allergen, a tree pollen allergen, a hay allergen, a grass allergen, a mold allergen, and a cockroach allergen. According to another embodiment, the at least one optional second agent is selected from the group consisting of a histamine IgE antagonist, a peptide antagonist, a peptidomimetic, an antibody, a cytokine inhibitor, and a leukotriene inhibitor. According to another embodiment, the method further comprises the step of labeling the white blood cells in the whole blood sample of step (a) with at least one differential label to identify a specific population of cells. According to another embodiment, the at least one differential label is at least one differential stain. According to another embodiment, the at least one differential label is at least one antibody. According to another embodiment, the at least one antibody is at least one fluorescently-labeled antibody. According to another embodiment, the fluorescently-labeled antibody is an antibody selected from the group consisting of an antibody against cell surface marker CD3 (TCR) complex, an antibody against cell surface marker CD16, an antibody against cell surface marker CD19, an antibody against cell surface marker CD56, an antibody against cell surface marker CD66b, an antibody against cell surface marker HIA-DR, an antibody against cell surface marker CD20, an antibody against cell surface marker CD123, an antibody against cell surface marker CD11b, an antibody against cell surface marker CD63, an antibody against cell surface marker CD203c, an antibody against cell surface marker CD294, an antibody against cell surface marker CD4, and an antibody against cell surface marker CD14. According to another embodiment, fractionating step (b) further comprises the step: utilizing a gating strategy to identify basophils, the gating strategy comprising the steps: 1) excluding doublets based on forward scatter area versus height; 2) selecting leukocytes based on forward and side scatter; 3) excluding dead cells using a fixable dead cell stain (LIVE/DEAD® Near InfraRed); and 4) selecting the basophil population as a CD3−, CD16−/CD20−/CD56−/CD66b−/HLA-DR− and CD294+ population. According to another embodiment, fractionating step (b) further comprises the step: utilizing a gating strategy to identify basophils, the gating strategy comprising the steps: 1) gating basophils based on scatter properties; 2) gating natural killer cells based on a level of expression of cell surface marker CD56; 3) gating BandT cells based on a level of expression of cell surface marker CD19 and a level of expression of cell surface marker CD4; 4) gating monocytes based on a level of expression of cell surface marker CD11b; and 5) gating basophils based on a level of expression of cell surface marker CD203c and a level of expression of cell surface marker CD294. According to another embodiment, fractionating step (b) further comprises the step: utilizing a gating strategy to identify basophils, the gating strategy further comprising the step of gating basophils based on a level of expression of cell surface marker CD203c and a level of expression of cell surface marker CD63. According to another embodiment, the level of expression of cell surface marker CD63 is correlated to the level of expression of cell surface marker CD203c relative to a background level of expression of cell surface marker CD63 and cell surface marker CD203. According to another embodiment, the level of expression of cell surface marker CD203c is at least about 8-fold higher than the level of expression of cell surface marker CD63.

According to another aspect, the described invention provides an in vitro system for reliable detection or quantification of a specific white blood cell population in a whole blood sample, the system comprising the following components: (a) a whole blood sample provided by a subject; wherein the whole blood sample comprises white blood cells, wherein the white blood cells comprise at least one cell population selected from the group of (i) a basophil population comprising at least one activatable basophil and (ii) an eosinophil population comprising at least one activatable eosinophil, wherein the basophil cell population expresses at least one cell surface marker characteristic of the at least one activatable basophil, and wherein the eosinophil cell population expresses at least one cell surface marker characteristic of the at least one activatable eosinophil; (b) at least one differential label to identify the at least one specific population of cells, (c) a means for fractionating the whole blood sample of (a) to detect and quantify the basophil population and the at least one eosinophil population; and (d) a means for correlating information obtained from component (c) with a disease state. According to one embodiment of the system, component (d) is a computer. According to another embodiment, the disease state is an allergic disease. According to another embodiment, the disease state is an allergic rhinitis, asthma, atopic dermatitis, eosinophilic espohagitis, mastocytosis, anaphylaxis, an angioedema, an autoimmune disorder or a monoclonal gammopathy. According to another embodiment, the whole blood sample in (a) is of a volume of about 5 µl to about 500 µl According to another embodiment, the at least one differential label of (b) is at least one differential stain. According to another embodiment, the at least one differential stain is at least one chemical stain. According to another embodiment, the at least one differential label is at least one antibody. According to another embodiment, the at least one antibody is at least one antibody selected from the group consisting of an antibody against the cell surface marker CD3 (TCR) complex, an antibody against cell surface marker CD16, an antibody against cell surface marker CD19, an antibody against cell surface marker CD56, an antibody against cell surface marker CD66b, an antibody against cell surface marker HIA-DR, an antibody against cell surface marker CD20, an antibody against cell surface marker CD123, an antibody against cell surface marker CD11b, an antibody against cell surface marker CD63, an antibody against cell surface marker CD203c, an antibody against cell surface marker CD294, an antibody against cell surface marker CD4, and an antibody against cell surface marker CD14. According to another embodiment, the means for fractionating in (c) is a flow cytometer. According to another embodiment, the flow cytometer utilizes a gating strategy to identify basophils such that 1) doublets based on forward scatter area versus height are excluded; 2) leukocytes are selected based on forward and side scatter; 3) dead cells are excluded using a fixable dead cell stain (LIVE/DEAD® Near InfraRed); and 4) the basophil population is selected as a CD3−/CD16−/CD20−/CD56−/CD66b−IHLA-DR− and CD294+ population. According to another embodiment, the flow cytometer utilizes a gating strategy to identify basophils such that 1) basophils are gated based on scatter properties; 2) natural killer cells are gated based on a level of expression of cell surface marker CD56; 3) B and T cells are gated based on a level of expression of cell surface marker CD19 and a level of expression of cell surface marker CD4; 4) monocytes are gated based on a level of expression of cell surface marker CD11b; and 5) basophils are gated based on a level of expression of cell surface marker CD203c and a level of expression of cell surface marker CD294. According to another embodiment, the flow cytometer utilizes a gating strategy to identify basophils such that basophils are gated based on a level of expression of cell surface marker CD203c and a level of expression of cell surface marker CD63. According to another embodiment, the level of expression of cell surface marker CD63 is correlated to a level of expression of cell surface marker CD203c relative to a background level of expression of cell surface marker CD63 and cell surface marker CD203. According to another embodiment, the level of expression of cell surface marker CD203c is at least about 8-fold higher than the level of expression of cell surface marker CD63. According to another embodiment, the at least one activatable basophil further expresses at least one intracellular marker characteristic of the at least one activatable basophil. According to another embodiment, in (d) a level of expression of at least one intracellular marker characteristic of the at least one activatable basophil is correlated to the level of expression of the at least one cell surface marker characteristic of the at least one activatable basophil relative to a background level of expression of the at least one surface marker and of the at least one intracellular marker that is characteristic of a nonactivated basophil. According to another embodiment, the intracellular marker is an intracellular marker selected from the group consisting of a cytokine, a transcription factor, a phosphoprotein, a histamine and a leukotriene.

BRIEF DESCRIPTION OF THE DRAWINGS

FIG. 1 shows FACS enables granulocyte phenotyping from one drop of blood.

FIG. 2 shows basophil surface expression of CD203c was specifically increased after stimulation with the offending allergen (n=4).

FIG. 3 shows stimulation with peanut allergen rapidly increases CD203c expression on basophils in blood samples from patients allergic to nuts.

FIG. 10 shows graphs of the CD63 (MFI) versus time.

DETAILED DESCRIPTION

Figure 1A:
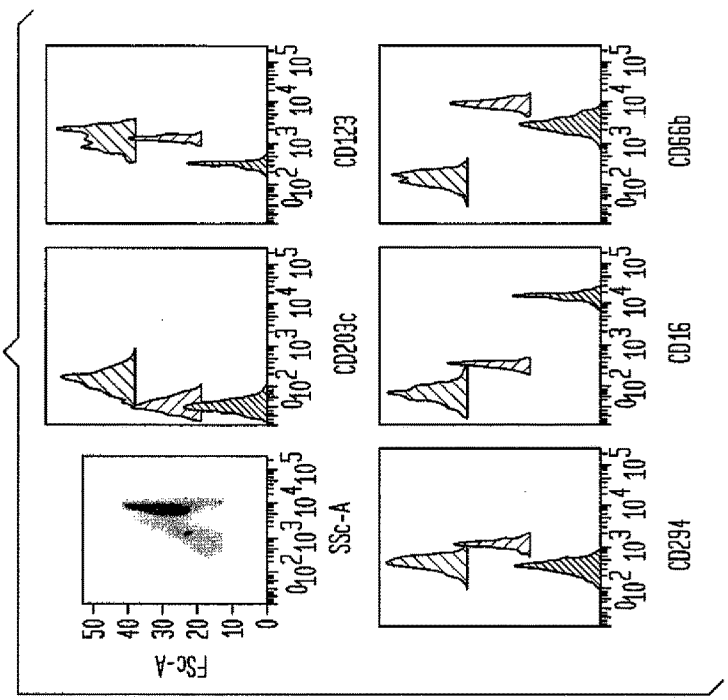
FIG. 1A shows doublets were excluded based on forward scatter area vs. height (upper left panel); leukocytes were selected based on forward and side scatter (upper right panel); dead cells were excluded using a fixable dead cell stain (LIVE/DEAD® Near InfraRed) (lower left panel); and basophils were selected as the CD3−, CD16−/CD20−/CD56−/CD66B−IHLA-DR− and CD294+ population; using the same markers, neutrophils and eosinophils also may be selected (lower right panel).

The invention described below relates to methods for detecting nonactivated basophils in a whole blood sample obtained from a normal healthy subject, methods for determining susceptibility to an allergic reaction to an allergen of a subject with no known allergy to the antigen, methods for measuring a response to challenge with a potential allergen in a whole blood sample obtained from a subject with known allergic reactivity to allergens other than the potential allergen; and to an in vitro system for reliable detection or quantification of a specific white blood cell population in a whole blood sample.

Glossary

The term "activatable" as used herein refers to having potential to become biologically or physiologically active.

The term "activation marker" as used herein refers to a cell surface marker, which is highly associated with a particular cell and which is selectively upregulated during a physiological condition. The physiological condition may be exposure to a substance, an allergen, a drug, a protein or a chemical, or other stimuli, or removal of a stimuli, a substance, a protein, an allergen, a drug or a chemical.

The term "active" or "activated" and its various grammatical forms as used herein refers to have biological or physiological effect.

The term "allergen" as used herein refers to any substance that induces an allergy in a susceptible subject. The use of the term "allergen" is inclusive of antigens that typically elicit a specific IgE response. Allergens ordinarily have little or no intrinsic toxicity, but induce pathology due to their ability to elicit an IgE-associated immune response, and, upon subsequent exposure, to elicit IgE- and/or T cell-dependent hypersensitivity reactions. Antigens that can elicit contact hypersensitivity responses are often called contact allergens, even though they may not also elicit an IgE response. Common allergens include, but are not limited to, pollen, grasses, dust, as well as some foods, such as, but not limited to, peanuts, cashews, walnuts, almonds, and brazil nuts, venoms, and medications.

The term "allergy" as used herein refers to an abnormal reaction of the body to a previously encountered allergen introduced by inhalation, ingestion or skin contact. The use of the term "allergy" also is inclusive of clinically adverse reactions to environmental antigens (allergens) which reflect the expression of acquired immunologic responsiveness involving allergen-specific antibodies and/or T cells. The term "allergy" includes adverse immunologic responses that are associated with the production of allergen-specific IgE.

The term "allergic diseases" as used herein refers to the group of clinical disorders in which immune responses, typically directed against otherwise innocuous environmental allergens, are thought to have a pathogenetic role. Allergic diseases include, but are not limited to, hay fever, allergic asthma, atopic dermatitis, and clinical disorders in which IgE associated immune responses are thought to have a role.

The term "anaphylactic shock" as used herein refers to a sudden, severe allergic reaction typically characterized by a sharp drop in blood pressure, urticaria, and breathing difficulties that is caused by exposure to a foreign substance after a preliminary or sensitizing exposure.

The term "anaphylaxis" as used herein refers to hypersensitivity to a substance that is caused by exposure to a foreign substance after a preliminary exposure.

The term "antigen" and its various grammatical forms refers to any substance that can stimulate the production of antibodies and can combine specifically with them. The term "antigenic determinant" or "epitope" as used herein refers to an antigenic site on a molecule.

The term "atopy" as used herein refers to a propensity to develop immediate hypersensitivity reactions to common allergens.

The term "cell surface marker" as used herein refers to an antigenic determinant or epitope found on the surface of a specific type of cell. Cell surface markers can facilitate the characterization of a cell type, its identification, and eventually its isolation. Cell sorting techniques are based on cellular biomarkers where a cell surface marker(s) may be used for either positive selection or negative selection, i.e., for inclusion or exclusion, from a cell population.

The term "chemokine" as used herein refers to a class of chemotactic cytokines that signal leukocytes to move in a specific direction. The terms "chemotaxis" or "chemotactic" refer to the directed motion of a motile cell or part along a chemical concentration gradient towards environmental conditions it deems attractive and/or away from surroundings it finds repellent.

The term "chromophore" as used herein refers to a part (or moiety) of a molecule responsible for its color. When a molecule absorbs certain wavelengths of visible light and transmits or reflects others, the molecule has a color. A chromophore is a region in a molecule where the energy difference between two different molecular orbitals falls within the range of the visible spectrum. Visible light that hits the chromophore thus can be absorbed by exciting an electron from its ground state into an excited state. In biological molecules that serve to capture or detect light energy, the chromophore is the moiety that causes a conformational change of the molecule when hit by light.

The term "colony stimulating factor" as used herein refers to a cytokine responsible for controlling the production of white blood cells. Types of colony stimulating factors include granulocyte colony stimulating factor (G-CSF), macrophage colony stimulating factor (M-CSF), and granulocyte macrophage colony stimulating factor (GM-CSF).

The term "complete blood count" (CBC) refers to a laboratory test that provides detailed information about the amount and the quality of each of the blood cell types. It usually includes a measurement of each of the three major blood cells (red blood cells, white blood cells, and platelets) and a measure of the hemoglobin and hematocrit. "Hemoglobin" (HGB) refers to the number of grams of hemoglobin in a deciliter of blood (g/dL). Normal hemoglobin levels in healthy adult human subjects are about 14 g/dL to about 18 g/dL for men and about 12 g/dL to about 16 g/dL for women. As a rough guideline, hemoglobin generally should be about one-third the hematocrit. "Red Blood Cell Count" (RBC) refers to the total number of red blood cells in a quantity of blood. Normal ranges in human subjects are about 4.5 million cells/mm$^3$ to about 6.0 million cells/mm$^3$ for men and about 4.0 million cells/mm$^3$ to about 5.5 million cells/mm$^3$ for women. "White Blood Cell Count" (WBC) refers to the total number of while blood cells or leukocytes in a quantity of blood. Normal ranges in human subjects are about $4.3 \times 10^3$ cells/mm$^3$ to about $10.8 \times 10^3$ cells/mm$^3$. "Hematocrit" (HCT) refers to the proportion of red blood cells as a percentage of total blood volume. A normal hematocrit for human subjects is about 40% to about 55% for men and about 35% to about 45% for women The term "condition" as used herein refers to a variety of health states and is meant to include disorders or diseases caused by any underlying mechanism or disorder, injury, and the promotion of healthy tissues and organs.

The term "contact" and all its grammatical forms as used herein refers to a state or condition of touching or of immediate or local proximity.

The term "cytokine" as used herein refers to small soluble protein substances secreted by cells, which have a variety of effects on other cells. Cytokines mediate many important physiological functions, including growth, development, wound healing, and the immune response. They act by binding to their cell-specific receptors located in the cell membrane, which allows a distinct signal transduction cascade to start in the cell, which eventually will lead to biochemical and phenotypic changes in target cells. Generally, cytokines act locally. They include type I cytokines, which encompass many of the interleukins, as well as several hematopoietic growth factors; type II cytokines, including the interferons and interleukin-10; tumor necrosis factor ("TNF")-related molecules, including TNFα and lymphotoxin; immunoglobulin super-family members, including interleukin 1 ("IL-1"); and the chemokines, a family of molecules that play a critical role in a wide variety of immune and inflammatory functions. The same cytokine can have different effects on a cell depending on the state of the cell. Cytokines often regulate the expression of, and trigger cascades of, other cytokines.

The term "cytometry" as used herein refers to a process in which physical and/or chemical characteristics of single cells, or by extension, of other biological or nonbiological particles in roughly the same size or stage, are measured. In flow cytometry, the measurements are made as the cells or particles pass through the measuring apparatus (a flow cytometer) in a fluid stream. A cell sorter, or flow sorter, is a flow cytometer that uses electrical and/or mechanical means to divert and collect cells (or other small particles) with measured characteristics that fall within a user-selected range of values.

The term "CXCR-4" as used herein refers to a G-protein-linked chemokine receptor.

The term "differential label" as used herein generally refers to a stain, dye, marker, or antibody used to characterize or contrast structures, components or proteins of a single cell or organism.

The term "disease" or "disorder" as used herein refers to an impairment of health or a condition of abnormal functioning.

The term "drop" as used herein refers to a small quantity of liquid or liquid globule that is produced, or falls, in a more or less spherical mass.

The term "drug" as used herein refers to a therapeutic agent or any substance, other than food, used in prevention, diagnosis, alleviation, treatment or cure of disease.

The term "dye" (also referred to as "fluorochrome" or "fluorophore") as used herein refers to a component of a molecule which causes the molecule to be fluorescent. The component is a functional group in the molecule that absorbs energy of a specific wavelength and re-emits energy at a different (but equally specific) wavelength. The amount and wavelength of the emitted energy depend on both the dye and the chemical environment of the dye. Many dyes are known, including, but not limited to, FITC, R-phycoerythrin (PE), PE-Texas Red Tandem, PE-Cy5 Tandem, propidium iodem, EGFP, EYGP, ECF, DsRed, allophycocyanin (APC), PerCp, SYTOX Green, courmarin, Alexa Fluors (350, 430, 488, 532, 546, 555, 568, 594, 633, 647, 660, 680, 700, 750), Cy2, Cy3, Cy3.5, Cy5, Cy5.5, Cy7, Hoechst 33342, DAPI, Hoechst 33258, SYTOX Blue, chromomycin A3, mithramycin, YOYO-1, SYTOX Orange, ethidium bromide, 7-AAD, acridine orange, TOTO-1, TO-PRO-1, thiazole orange, TOTO-3, TO-PRO-3, thiazole orange, propidium iodide (PI), LDS 751, Indo-1, Fluo-3, DCFH, DHR, SNARF, Y66F, Y66H, EBFP, GFPuv, ECFP, GFP, AmCyan1, Y77W, S65A, S65C, S65L, S65T, ZsGreen1, ZsYellow1, DsRed2, DsRed monomer, AsRed2, mRFP1, HcRed1, monochlorobimane, calcein, the DyLight Fluors, cyanine, hydroxycoumarin, aminocoumarin, methoxycoumarin, Cascade Blue, Lucifer Yellow, NBD, PE-Cy5 conjugates, PE-Cy7 conjugates, APC-Cy7 conjugates, Red 613, fluorescein, FluorX, BODIDY-FL, TRITC, Xrhodamine, Lissamine Rhodamine B, Texas Red, TruRed, and derivatives thereof.

The term "expression" as used herein refers to the action of a gene in the production of a protein or phenotype. "Level of expression" refers to the degree to which a particular gene produces its effect(s) in an organism.

The term "fluorescence" as used herein refers to the result of a three-state process that occurs in certain molecules, generally referred to as "fluorophores" or "fluorescent dyes," when a molecule or nanostructure relaxes to its ground state after being electrically excited. Stage 1 involves the excitation of a fluorophore through the absorption of light energy; Stage 2 involves a transient excited lifetime with some loss of energy; and Stage 3 involves the return of the fluorophore to its ground state accompanied by the emission of light.

The term "fluorescent-activated cell sorting" (also referred to as "FACS") as used herein refers to a method for sorting a heterogeneous mixture of biological cells into one or more containers, one cell at a time, based upon the specific light scattering and fluorescent characteristics of each cell.

The term "fractionate" and its various grammatical forms as used herein refers to separating or dividing into component parts, fragments, or divisions.

The term "IgE-associated immune response" as used herein refers to a group of immune responses, whether protective or clinically adverse, which are associated with the production of specific IgE to certain antigens (allergens).

The term "healthy" as used herein refers to a state of physical, mental, emotional and social well-being.

The term "hematopoietic stem cell" refers to a cell isolated from the blood or from the bone marrow that can renew itself, differentiate to a variety of specialized cells, mobilize out of the bone marrow into the circulating blood, and undergo programmed cell death (apoptosis). In some embodiments of the described invention, hematopoietic stem cells derived from human subjects express at least one type of cell surface marker, including, but not limited to, CD34, CD38, HLA-DR, c-kit, CD59, Sca-1, Thy-1, and/or CXCR-4, or a combination thereof.

The term "human subject" as used herein refers to a living individual about whom an investigator offers (i) data through intervention or interaction with the individual; or (ii) identifiable private information.

The term "humanized monoclonal antibodies" refers to antibodies in which the complementarity determining regions, ("CDRs"), which fashion the antibody binding site of a mouse monoclonal antibody, are replaced with a CDR of a human protein, while maintaining the framework and constant regions of the mouse antibody.

The term "hypersensitivity reaction" as used herein refers to allergic reactions that may be deleterious to the tissues and harmful to the host.

The term "immediate hypersensitivity reactions" ("acute IgE-associated allergic reaction") as used herein refers to a group of immunologically specific reactions, whether local or systemic, which typically occur within minutes of allergen exposure in sensitized individuals and which reflect on the surface of effector cells, such as mast cells or basophils. This results in the aggregation of the receptors, leading to the activation of the effector cells to release mediators that produce the acute signs and symptoms of the reaction.

The term "inflammation" as used herein refers to a physiologic response to infection and injury in which cells involved in detoxification and repair are mobilized to the compromised state by inflammatory mediators. The classic signs of inflammation are pain (dolor), heat (calor), redness (rubor), swelling (tumor), and loss of function (functio laesa). Histologically, inflammation involves a complex series of events, including dilation of arterioles, capillaries, and venules, with increased permeability and blood flow; exudation of fluids, including plasma proteins; and leukocytic migration into the inflammatory focus.

The term "acute inflammation" as used herein refers to inflammation, usually of sudden onset, characterized by the classical signs, with predominance of the vascular and exudative processes. The term "chronic inflammation" as used herein refers to inflammation of slow progress and marked chiefly by the formation of new connective tissue; it may be a continuation of an acute form or a prolonged low-grade form, and usually causes permanent tissue damage.

Regardless of the initiating agent, the physiologic changes accompanying acute inflammation encompass four main features: (1) vasodilation, which results in a net increase in blood flow, is one of the earliest physical responses to acute tissue injury; (2) in response to inflammatory stimuli, endothelial cells lining the venules contract, widening the intracellular junctions to produce gaps, leading to increased vascular permeability which permits leakage of plasma proteins and blood cells out of blood vessels; (3) inflammation often is characterized by a strong infiltration of leukocytes at the site of inflammation, particularly neutrophils (polymorphonuclear cells). These cells promote tissue damage by releasing toxic substances at the vascular wall or in uninjured tissue; and (4) fever, produced by pyrogens released from leukocytes in response to specific stimuli.

During the inflammatory process, soluble inflammatory mediators of the inflammatory response work together with cellular components in a systemic fashion in the attempt to contain and eliminate the agents causing physical distress. The term "inflammatory mediators" as used herein refers to the molecular mediators of the inflammatory process. These soluble, diffusible molecules act both locally at the site of tissue damage and infection and at more distant sites. Some inflammatory mediators are activated by the inflammatory process, while others are synthesized and/or released from cellular sources in response to acute inflammation or by other soluble inflammatory mediators. Examples of inflammatory mediators of the inflammatory response include, but are not limited to, plasma proteases, complement, kinins, clotting and fibrinolytic proteins, lipid mediators, prostaglandins, leukotrienes, platelet-activating factor (PAF), peptides and amines, including, but not limited to, histamine, serotonin, and neuropeptides, proinflammatory cytokines, including, but not limited to, interleukin-1, interleukin-4, interleukin-6, interleukin-8, tumor necrosis factor (TNF), interferon-gamma, and interleukin 12.

The term "interaction" means communication or interpersonal contact between investigator and subject.

The term "interleukin" as used herein refers to a cytokine secreted by white blood cells as a means of communication with other white blood cells.

The term "intervention" includes physical procedures by which data are gathered (e.g., ventipuncture) and manipulations of the subject or the subject's environment that are performed for research purposes.

The term "isolate" and its various grammatical forms as used herein refers to placing, setting apart, or obtaining a protein, molecule, substance, nucleic acid, peptide, cell or particle, in a form essentially free from contaminants or other materials with which it is commonly associated.

The term "labeling" as used herein refers to a process of distinguishing a compound, structure, protein, peptide, antibody, cell or cell component by introducing a traceable constituent. Common traceable constituents include, but are not limited to, a fluorescent antibody, a fluorophore, a dye or a fluorescent dye, a stain or a fluorescent stain, a marker, a fluorescent marker, a chemical stain, a differential stain, a differential label, and a radioisotope.

The term "manifestation" as used herein refers to an outward or perceptible indication.

The term "nonactivated" and its various grammatical forms as used herein refers to a native physiological state, or wild-type state.

The term "normal" refers to a standard, model, median or average of a large group.

The term "normal healthy subject" refers to a subject having no symptoms or other evidence of allergy.

The term "peptide" as used herein refers to a polypeptide, protein or peptidomimetic. The terms "polypeptide", "peptide" and "protein" are used herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein that protein is specifically reactive to antibodies elicited to the same protein but consisting entirely of naturally occurring amino acids. The terms "polypeptide", "peptide" and "protein" also are inclusive of modifications including, but not limited to, glycosylation, lipid attachment, sulfation, gamma-carboxylation of glutamic acid residues, hydroxylation and ADP-ribosylation. It will be appreciated, as is well known and as noted above, that polypeptides may not be entirely linear. For instance, polypeptides may be branched as a result of ubiquitination, and they may be circular, with or without branching, generally as a result of posttranslational events, including natural processing event and events brought about by human manipulation which do not occur naturally. Circular, branched and branched circular polypeptides may be synthesized by non-translation natural process and by entirely synthetic methods, as well.

The term "peptidomimetic" as used herein refers to a small protein-like chain designed to mimic a peptide. A peptidomimetic typically arises from modification of an existing peptide in order to alter the molecule's properties.

The term "phosphoepitope" as used herein refers to a phosphorylated protein on a cell surface. A comparison of phosphoepitopes frequently is used to determine the activation status of a cell or cell population as the measurement of phosphorylation of signaling intermediates may allow for association of network topologies with disease states. For example, transduction signaling cascades involve transmembrane receptors that bind to a specific extracellular ligand, such as a hormone or a cytokine. This binding initiates the transduction of a signal by a cascade of intracellular enzymal events that ultimately results in degranulation, apoptosis, proliferation, migration, organization of the assembling of ribosomes, and/or gene transcription. These transduction cascades often proceed by sequentially adding or removing phoshate residues via phosphorylation or dephosphorylation to a series of enzymes in the cascade. Within the transduction signaling cascades, four major components include: (1) the transmembrane receptor and its specific ligand (e.g., insulin receptor and insulin); (2) the kinases (phosphorylation enzymes that up-regulate or down-regulate the activity of a cascade enzyme); (3) phosphatases (dephosphorylating enzymes); and (4) the final acceptor of the cascade which performs the function(s) that initiating the cascade triggers.

The term "presentation" and its various grammatical forms means a showing, demonstration or manifestation of a disease, disease state, disorder, or symptom of disease, disease state, or disorder, inclusive of allergy and allergic reaction.

The term "private information" as used herein refers to information that occurs in a context in which an individual reasonably can expect that no observation or recording is taking place and information which has been provided for specific purposes by an individual and which the individual can reasonably expect will not be made public (e.g., a medical record).

The term "stain" as used herein refers to a composition of a dye(s) or pigment(s) used to make a structure, a material, a cell, a cell component, a membrane, a granule, a nucleus, a cell surface receptor, a peptide, a microorganism, a nucleic acid, a protein or a tissue differentiable.

The term "subject" or "individual" or "patient" are used interchangeably to refer to a member of an animal species of mammalian origin, including but not limited to, a mouse, a rat, a cat, a goat, sheep, horse, hamster, ferret, pig, a dog, a guinea pig, a platypus, a rabbit and a primate, such as, for example, a monkey, ape, or human.

The term "subject prone to allergy" as used herein means a subject having a medical history or previous allergic reaction to at least one allergen other than the allergen responsible for said allergy.

The term "susceptible" as used herein refers to a member of a population at risk. The term is inclusive of a subject having a medical history of a previous allergic reaction to at least one allergen and at risk of mounting an allergic reaction to a different antigen.

The term "therapeutic effect" as used herein refers to a consequence of treatment, the results of which are judged to be desirable and beneficial. A therapeutic effect may include, directly or indirectly, the arrest, reduction, or elimination of a disease manifestation. A therapeutic effect may also include, directly or indirectly, the arrest reduction or elimination of the progression of a disease manifestation. The term "therapeutically effective amount" or an "amount effective" of one or more of an active agent is an amount that is sufficient to provide a therapeutic effect. Generally, an effective amount of the active agents that can be employed ranges from about 0.000001 mg/kg body weight to about 100 mg/kg body weight. However, dosage levels are based on a variety of factors, including the type of injury, the age, weight, sex, medical condition of the patient, the severity of the condition, the route of administration, and the particular active agent employed. Thus the dosage regimen may vary widely, but can be determined routinely by a physician using standard methods.

The term "therapeutic agent" as used herein refers to a drug, molecule, nucleic acid, protein, composition or other substance that provides a therapeutic effect. The term "active" as used herein refers to the ingredient, component or constituent of the compositions of the present invention responsible for the intended therapeutic effect. The terms "therapeutic agent" and "active agent" are used interchangeably herein.

The term "treat" or "treating" as used herein refers to accomplishing one or more of the following: (a) reducing the severity of a disorder; (b) limiting the development of symptoms characteristic of a disorder being treated; (c) limiting the worsening of symptoms characteristic of a disorder being treated; (d) limiting the recurrence of a disorder in patients that previously had the disorder; and (e) limiting recurrence of symptoms in patients that were previously symptomatic for the disorder.

The term "venipuncture" as used herein refers to the process of obtaining intravenous access for the purpose of intravenous therapy or obtaining a sample of venous blood.

The term "whole blood" as used herein refers to generally unprocessed or unmodified collected blood containing all of its components, such as red blood cells, white blood cells, platelets and plasma. The term "whole blood" is inclusive of any anticoagulant that may be combined with the blood upon collection.

I. Method for Detecting Nonactivated Basophils in a Whole Blood Sample

According to one aspect, the described invention provides a method for detecting nonactivated basophils in a whole blood sample obtained from a normal healthy subject, the method comprising the steps:

(a) collecting a whole blood sample from the subject;
wherein the whole blood sample comprises white blood cells,
wherein the white blood cells comprise at least one cell population selected from the group of (i) a basophil population comprising at least one nonactivated basophil and (ii) an eosinophil population comprising at least one nonactivated eosinophil,
wherein the nonactivated basophil in the basophil cell population expresses at least one cell surface marker characteristic of the at least one nonactivated basophil; and
wherein the eosinophil population expresses at least one cell surface marker characteristic of the at least one nonactivated eosinophil;
(b) fractionating the whole blood sample by flow cytometry to separate the basophil population from the eosinophil population, (c) specifically detecting a nonactivated basophil in the basophil cell population; and (d) optionally specifically detecting a nonactivated eosinophil in the eosinophil cell population.

According to one embodiment, collecting step (a) of a whole blood sample from a human patient is by venipuncture. According to another embodiment, the venipuncture is by an evacuated tube system. According to another embodiment, the venipuncture is by needle and syringe. According to another embodiment, the venipuncture is by a pin-prick puncture. According to some embodiments, the venipuncture is by a neonatal heel prick.

According to another embodiment, the whole blood sample of step (a) is of a volume of about 1 drop to about 20 drops. According to another embodiment, the whole blood sample volume is of about 5 µl. According to another embodiment, the whole blood sample volume is of a volume of about 25 µl. According to another embodiment, the whole blood sample is of a volume of about 50 µl. According to another embodiment, the whole blood sample is of a volume of about 100 µl. According to another embodiment, the whole blood sample is of a volume of about 200 µl. According to another embodiment, the whole blood sample is of a volume of about 300 µl. According to another embodiment, the whole blood sample is of a volume of about 400 µl. According to another embodiment, the whole blood sample is of about 500 µl. According to another embodiment, the whole blood sample is of a volume of about 1 ml. According to another embodiment, the whole blood sample is of a volume of about 5 ml.

According to another embodiment, the whole blood sample of step (a) is labeled with at least one differential label to identify a specific population of cells. According to some embodiments, the specific population of cells is a population of basophils According to some embodiments, the specific population of cells is a population of eosinophils According to some embodiments, the specific population of cells is a population of neutrophils According to some such embodiments, the specific population of cells is a population of monocytes. According to some embodiments, the specific population of cells is a population of natural killer (NK) cells. According to some embodiments, the specific population of cells is a population of T cells. According to some embodiments, the specific population of cells is a population of B cells. According to some embodiments, the specific population of cells is a population of macrophages. According to some embodiments, the specific population of cells is a population of Langerhans cells.

According to some embodiments, the at least one differential label is a differential stain. According to some such embodiments, the differential stain is a chemical stain. Such chemical stains include, but are not limited to, eosin, methylene blue, Wright's stain (eosin Y, azure B and methylene blue), Jenner's stain (methylene blue eosinate), Leishman stain (methylene blue and eosin), and Giemsa stain (methylene blue and eosin).

It generally is believed that use of multicolor assays, where additional reagents are added, allows for better precision and better specificity.

According to another embodiment, the at least one differential label comprises a fluorophore. According to another embodiment, the at least one differential label comprises a fluorochrome dye. According to some such embodiments, the at least one differential label is a fluorescent label. According to some such embodiments, the fluorescent label is a fluorescent dye or a fluorescent stain.

According to another embodiment, the at least one differential label is a Live-Dead® (Invitrogen, Carlsbad, Calif.) cell viability stain. These fluorescence-based stains can be used to label animal cells, bacteria, yeast and fungi. Briefly, a cell population is stained with $C_{12}$-resazurin and SYTOX Green®, then analyzed by flow cytometry, exciting at 488 nm and measuring fluorescence emission at 530 nm and 575 nm. The cell population thus is resolved into two groups: 1) live cells with a low level of green and a high level of orange fluorescence; and 2) necrotic cells with a high level of green fluorescence and a low level of orange fluorescence.

According to some such embodiments, the fluorescent label is a Fixable Dead Cell stain (LIVE/DEAD®). These fluorescent dyes cannot penetrate the cell membrane of viable cells, thus only cell surface proteins are available to react with the dye (resulting in a less intense stain); however, the dyes can penetrate the membranes of dead or injured cells, allowing for staining of both extracellular and intracellular amines (resulting in a more intense stain).

According to some such embodiments, the at least one differential label is an antibody. Antibodies are serum proteins the molecules of which possess small areas of their surface that are complementary to small chemical groupings on their targets. These complementary regions (referred to as the antibody combining sites or antigen binding sites) of which there are at least two per antibody molecule, and in some types of antibody molecules ten, eight, or in some species as many as 12, may react with their corresponding complementary region on the antigen (the antigenic determinant or epitope) to link several molecules of multivalent antigen together to form a lattice.

The basic structural unit of a whole antibody molecule consists of four polypeptide chains, two identical light (L) chains (each containing about 220 amino acids) and two identical heavy (H) chains (each usually containing about 440 amino acids). The two heavy chains and two light chains are held together by a combination of noncovalent and covalent (disulfide) bonds. The molecule is composed of two identical halves, each with an identical antigen-binding site composed of the N-terminal region of a light chain and the N-terminal region of a heavy chain. Both light and heavy chains usually cooperate to form the antigen binding surface.

Human antibodies show two kinds of light chains, κ and λ; individual molecules of immunoglobulin generally are only one or the other. In normal serum, 60% of the molecules have been found to have κ determinants and 30 percent λ. Many other species have been found to show two kinds of light chains, but their proportions vary. For example, in the mouse and rat, λ chains comprise but a few percent of the total; in the dog and cat, κ chains are very low; the horse does not appear to have any κ chain; rabbits may have 5 to 40% λ, depending on strain and b-locus allotype; and chicken light chains are more homologous to λ than κ.

In mammals, there are five classes of antibodies, IgA, IgD, IgE, IgG, and IgM, each with its own class of heavy chain—α (for IgA), δ (for IgD), ε (for IgE), γ (for IgG) and μ (for IgM). In addition, there are four subclasses of IgG immunoglobulins (IgG$_1$, IgG$_2$, IgG$_3$, IgG$_4$) having γ1, γ2, γ3, and γ4 heavy chains respectively. In its secreted form, IgM is a pentamer composed of five four-chain units, giving it a total of 10 antigen binding sites. Each pentamer contains one copy of a J chain, which is covalently inserted between two adjacent tail regions.

All five immunoglobulin classes differ from other serum proteins in that they show a broad range of electrophoretic mobility and are not homogeneous. This heterogeneity—that individual IgG molecules, for example, differ from one another in net charge—is an intrinsic property of the immunoglobulins.

An antigenic determinant or epitope is an antigenic site on a molecule. Sequential antigenic determinants/epitopes essentially are linear chains. In ordered structures, such as helical polymers or proteins, the antigenic determinants/epitopes essentially would be limited regions or patches in or on the surface of the structure involving amino acid side chains from different portions of the molecule which could come close to one another. These are conformational determinants.

The principle of complementarity, which often is compared to the fitting of a key in a lock, involves relatively weak binding forces (hydrophobic and hydrogen bonds, van der Waals forces, and ionic interactions), which are able to act effectively only when the two reacting molecules can approach very closely to each other and indeed so closely that the projecting constituent atoms or groups of atoms of one molecule can fit into complementary depressions or recesses in the other. Antigen-antibody interactions show a high degree of specificity, which is manifest at many levels. Brought down to the molecular level, specificity means that the combining sites of antibodies to an antigen have a complementarity not at all similar to the antigenic determinants of an unrelated antigen. Whenever antigenic determinants of two different antigens have some structural similarity, some degree of fitting of one determinant into the combining site of some antibodies to the other may occur, and that this phenomenon gives rise to cross-reactions. Cross reactions are of major importance in understanding the complementarity or specificity of antigen-antibody reactions. Immunological specificity or complementarity makes possible the detection of small amounts of impurities/contaminations among antigens Monoclonal antibodies (mAbs) can be generated by fusing mouse spleen cells from an immunized donor with a mouse myeloma cell line to yield established mouse hybridoma clones that grow in selective media. A hybridoma cell is an immortalized hybrid cell resulting from the in vitro fusion of an antibody-secreting B cell with a myeloma cell. In vitro immunization, which refers to primary activation of antigen-specific B cells in culture, is another well-established means of producing mouse monoclonal antibodies.

Diverse libraries of immunoglobulin heavy ($V_H$) and light ($V_κ$ and $V_λ$) chain variable genes from peripheral blood lymphocytes also can be amplified by polymerase chain reaction (PCR) amplification. Genes encoding single polypeptide chains in which the heavy and light chain variable domains are linked by a polypeptide spacer (single chain Fv or scFv) can be made by randomly combining heavy and light chain V-genes using PCR. A combinatorial library then can be cloned for display on the surface of filamentous bacteriophage by fusion to a minor coat protein at the tip of the phage.

The technique of guided selection is based on human immunoglobulin V gene shuffling with rodent immunoglobulin V genes. The method entails (i) shuffling a repertoire of human λ light chains with the heavy chain variable region (VH) domain of a mouse monoclonal antibody reactive with an antigen of interest; (ii) selecting half-human Fabs on that antigen (iii) using the selected λ light chain genes as "docking domains" for a library of human heavy chains in a second shuffle to isolate clone Fab fragments having human light chain genes; (v) transfecting mouse myeloma cells by electroporation with mammalian cell expression vectors containing the genes; and (vi) expressing the V genes of the Fab reactive with the antigen as a complete IgG1, λ antibody molecule in the mouse myeloma.

According to some such embodiments, the antibody is a fluorescently-labeled antibody. According to some such embodiments, the antibody is a monoclonal antibody. According to some such embodiments, the antibody is at least one antibody of a polyclonal antibody mixture. A fluorescently-labeled antibody is an antibody with a covalently attached fluorphore and commonly is used as a specific probe for detection of a particular target. Monoclonal and polyclonal antibody labeling kits and fluorescent antibodies that generally utilize an amine-reactive fluorophore to covalently attach the label to an IgG antibody of interest are available from commercial vendors (such as, for example, Invitrogen (Carlsbad, Calif.); Abcam (Cambridge, Mass.); Molecular Probes, Inc. (Eugene, Oreg.); Biolegend (San Diego, Calif.); eBioscience (San Diego, Calif.); and Immunotech (Praha, CZ)).

According to some such embodiments, the fluorophore is a xanthene derivative. Xanthene derivatives include, but are not limited to, fluorescein (FITC), rhodamine, Oregon Green®, eosin, and Texas Red® (TR). According to some such embodiments, the fluorophore is a cyanine derivative. Cyanine derivatives include, but are not limited to, cyanine, indocarbocyanine, oxacarbocyanine, thiacarbocyanine and merocyanine. According to some such embodiments, the fluorophore is a coumarin derivative. According to some such embodiments, the fluorophore is a oxadiazole derivative. Oxadiazole derivatives include, but are not limited to, pyridyloxazole, nitrobenzoxadiazole, and benzoxadiazole. According to some such embodiments, the fluorophore is a pyrene derivative. Pyrene derivatives include, but are not limited to, Cascade Blue®. According to some such embodiments, the fluorophore is a boron-dipyrromethenene (BODIPY) or derivative thereof. According to some such embodiments, the fluorophore is an oxazine derivative. Oxazine derivatives include, but are not limited to, Nile red, Nile blue, cresyl violet, and oxazine 170. According to some such embodiments, the fluorophore is a acridine derivative. Acridine derivatives include, but are not limited to, proflavin, acridine orange and acridine yellow. According to some such embodiments, the fluorophore is a arylmethine derivative. Arylmethine derivatives include, but are not limited to, auramine, crystal violet, and Malachite Green®. According to some such embodiments, the fluorophore is an Alexa Fluor®. According to some such embodiments, the fluorophore is a tetrapyrrole derivative. Tetrapyrrole derivatives include, but are not limited to, porphin, phtalocyanine and bilirubin.

According to some such embodiments, the fluorescently-labeled antibody is an antibody against a cell surface marker CD3 (TCR) complex. Some such antibodies include, but are not limited to, mouse anti-human CD3 mAb S4.1 conjugated with a fluorophore such as, but not limited to, FITC, R-PE, TRI-COLOR®, Pacific Blue®, Alexa Fluor® 488, PE-TR, PE-Alexa Fluor® 610, PerCP, PE-Cy5.5, PE-Alexa Fluor® 700, PE-Cy7, APC, APC-Cy5.5 and APC-Alexa Fluor® 750 (Invitrogen, Carlsbad, Calif.); and mouse anti-human mAb UCHT1 conjugated with a fluorophore such as, but not limited to, Alexa Fluor® 405, Pacific Orange™, FITC, R-PE, PE-Alexa Fluor® 700, APC and Alexa Fluor® 700 (Invitrogen, Carlsbad, Calif.).

According to some such embodiments, the fluorescently labeled antibody is an antibody against cell surface marker CD16. Some such antibodies include, but are not limited to, mouse anti-human CD16 mAb 3G8 conjugated to a fluorophore such as, but not limited to, Pacific Blue™, Pacific Orange™, FITC, R-PE, PE-TR, TC, PerCP, PE-Alexa Fluor® 700, APC and Alexa Fluor® 700 (Invitrogen, Carlsbad, Calif.).

According to some such embodiments, the fluorescently labeled antibody is an antibody against cell surface marker CD19. Some such antibodies include, but are not limited to, mouse anti-human CD19 mAb SJ25-C1 conjugated to a fluorophore such as, but not limited to, Alexa Fluor® 488, FITC, PE-TR, PE-Alexa Fluor® 610, PerCP, PE-Cy™ 5.5, PE-Alexa Fluor® 700, PE-Cy™ 7, APC, APC-Alexa Fluor™ 750, Pacific Blue™, Alexa Fluor® 647 and Alexa Fluor® 700 (Invitrogen, Carlsbad, Calif.).

According to some such embodiments, the fluorescently labeled antibody is an antibody against cell surface marker CD56 (NCAM). Some such antibodies include, but are not limited to, mouse anti-human CD56 mAb B157; mouse anti-human CD56 mAb MEM-188 conjugated to a fluorophore such as, but not limited to, FITC, Alexa Fluor® 488, R-PE, PE-TR, TC, PE-Cy™ 5.5 (Invitrogen, Carlsbad, Calif.).

According to some such embodiments, the fluorescently labeled antibody is an antibody against cell surface marker CD66b (CGM1). Some such antibodies include, but are not limited to, CD66b, mouse anti-human (FITC) antibody; and CD66b antibody conjugated with fluorophores detectable with laser wavelengths of 407 nm.

According to some such embodiments, the fluorescently labeled antibody is an antibody against cell surface marker HLA-DR. Some such antibodies include, but are not limited to, HLA-DR (Class II), mouse anti-human mAb TU36 conjugated to a fluorophore such as, but not limited to, Pacific Blue™, Pacific Orange™, FITC, R-PE, PE-TR, TC, PerCP, PE-Cy™ 5.5, and APC.

According to some such embodiments, the fluorescently labeled antibody is an antibody against cell surface marker CD20. Some such antibodies include, but are not limited to, mouse anti-human mAb CD20 2H7 conjugated to a fluorophore such as, but not limited to, FITC (GenWay Biotech, San Diego, Calif.).

According to some such embodiments, the fluorescently labeled antibody is an antibody against cell surface marker CD123. Some such antibodies include, but are not limited to, PE-Cy™ 5 labeled mouse anti-human CD123 mAb 9F5; PE-labeled mouse anti-human CD123 mAb 7G3; mouse anti-human CD123 mAb 6H6 labeled with a fluorophore such as, but not limited to, FITC, PE/Cy™ 5, PE/Cy™ 7, PerCP/Cy™ 5.5, and PE (Biolegend, San Diego, Calif.; eBioscience, San Diego, Calif.).

According to some such embodiments, the fluorescently labeled antibody is an antibody against cell surface marker CD11b. Some such antibodies include, but are not limited to, Alexa Fluor® 488 labeled mouse anti-human CD11b mAb P1H4; FITC labeled mouse anti-human CD11b mAb 44; FITC labeled mouse anti-human CD11b mAb ICRF44; FITC labeled mouse anti-human CD11b mAb MEM-174;

FITC labeled mouse anti-human CD11b mAb 44; and PE labeled mouse anti-human CD11b mAb VIM12 (Abcam Inc., Cambridge, Mass.).

According to some such embodiments, the fluorescently labeled antibody is an antibody against cell surface marker CD63. Some such antibodies include, but are not limited to, mouse anti-human CD63 mAb CLB-gran/12 conjugated with a fluorophore such as, but not limited to, FITC and R-PE.

According to some such embodiments, the fluorescently labeled antibody is an antibody against cell surface marker CD203c. Some such antibodies include, but are not limited to, PE-anti-human CD203c; PE-labeled mAb 97A6 (Immunotech, Marsielle, France); R-PE-labeled mouse anti-human ENPP3 mAb 97A6; and PE-labeled mouse anti-human CD203c mAb NP4D6.

According to some embodiments, the fluorescently labeled antibody is an antibody against cell surface marker CD294. Some such antibodies include, but are not limited to, Alexa Fluor® 647-labeled rat anti-CD294 mAb BM16; and PE-labeled rat anti-human CRTH2 mAb BM16.23.

According to some embodiments, the fluorescently labeled antibody is an antibody against cell surface marker CD4. Some such antibodies include, but are not limited to, mouse anti-human CD4 mAb S3.5 conjugated to a fluorophore such as, but not limited to, Pacific Orange™, Alexa Fluor® 488, FITC, PE-TR, PE-Alexa Fluor® 610, TC, PerCP, PE-Cy™ 5.5, PE-Alexa Fluor® 700, PE-Cy™ 7, APC, APC-Cy™ 5.5, Alexa Fluor® 700, R-PE, and APC-Alexa Fluor® 750.

According to some embodiments, the fluorescently labeled antibody is an antibody against cell surface marker CD14. Some such antibodies include, but are not limited to, mouse anti-human CD14 mAb TuK4 conjugated to a fluorophore such as, but not limited to, Pacific Blue™, Pacific Orange™, FITC, R-PE, PE-TR, TC, PerCP, PE-Cy™ 5.5, PE-Alexa Fluor® 700, APC, APC-Alexa Fluor® 750, and Alexa Fluor® 700.

According to another embodiment, the at least one differential label is an antibody against a phosphoepitope.

According to another embodiment, fractionating step (b) is by flow cytometry. According to some such embodiments, the fractionating step (b) by flow cytometry further comprises the step of utilizing a gating strategy to identify a basophil population. The gating strategy comprises the steps: 1) excluding doublets and/or clumped cells (meaning two or more cells that are firmly bound to each other and cannot be characterized individually) based on forward scatter area versus height; 2) selecting leukocytes based on forward and side scatter; 3) excluding dead cells using a fixable dead cell stain (LIVE/DEAD® Near InfraRed); and 4) selecting the basophil population as a CD3−/CD16−/CD20−/CD56−/CD66b−IHLA-DR− and CD294+ population. There are alternative gating strategies for basophils such as, for example, but not limited to, CD203+/CD123+/CD63/HLA-DR and CD203+/CD294+/CD 123+/CD 11 b+/CD63+, CD 123+.

According to another embodiment, fractionating step (b) by flow cytometry further comprises the step of utilizing a gating strategy to identify a basophil population. The gating strategy comprises the steps: 1) gating basophils based on (light) scatter properties; 2) gating natural killer (NK) cells based on a level of expression of CD56 cell surface marker; 3) gating B and T cells based on a level of expression of CD19 cell surface marker and a level of expression of CD4 cell surface marker; 4) gating monocytes based on a level of expression of CD11b cell surface marker; and 5) gating basophils based on a level of expression of CD203c cell surface marker and a level of expression of CD294 cell surface marker. According to some embodiments, the gating basophils is based on a level of expression of the cell surface marker CD203c and on a level of expression of the cell surface marker CD123+. According to some such embodiments, the basophil population is sorted and stained with Giemsa solution (a mixture of methylene blue and eosin commonly used to stain peripheral blood samples where erythrocytes stain pink, platelets show a light pale pink, lymphocyte cytoplasm stains sky blue, monocyte cytoplasm stains pale blue, and leukocyte nuclear chromatin stains magenta). According to some such embodiments, an increase in the level of expression of cell surface marker CD203c from the basal level of expression of cell surface marker CD203c correlates to an allergy, wherein the increase in expression of cell surface marker CD203c is in response to an allergen challenge. According to some such embodiments, an increase in the level of expression of cell surface marker CD294 from the basal level of expression of cell surface marker CD294 correlates to an allergy, wherein the increase in expression of cell surface marker CD294 is in response to an allergen challenge. According to some such embodiments, an increase in the level of expression of cell surface markers CD203c and CD294 from the basal level of expression of cell surface markers CD203c and CD294 correlates to an allergy, wherein the increase in expression of cell surface marker CD203c and CD293 is in response to an allergen challenge.

According to another embodiment, fractionating step (b) further comprises the step of utilizing a gating strategy to identify basophils. The gating strategy further comprises the step of gating basophils based on expression of cell surface marker CD203c and of cell surface marker CD63. According to some such embodiments, the level of expression of cell surface marker CD63 is correlated to the level of expression of cell surface marker CD203c. According to some such embodiments, the level of expression of cell surface marker CD203c measured is at least about 5-fold higher than the level of expression of cell surface marker CD63. According to some such embodiments, the level of expression of cell surface marker CD203c measured is at least about 8-fold higher than the level of expression of cell surface marker CD63. According to some such embodiments, an increase in the level of expression of cell surface marker CD203c from the basal level of expression of cell surface marker CD203c correlates to an allergy, wherein the increase in expression of cell surface marker CD203c is in response to an allergen challenge. According to some such embodiments, an increase in the level of expression of cell surface marker CD63 from the basal level of expression of cell surface marker CD63 correlates to an allergy, wherein the increase in expression of cell surface marker CD63 is in response to an allergen challenge. According to some such embodiments, an increase in the level of expression of cell surface marker CD203c and cell surface marker CD63 from the basal level of expression of cell surface marker CD203c and cell surface marker CD63 correlates to an allergy, wherein an increase in expression of cell surface markers CD203c and CD63 is in response to an allergen challenge. According to another embodiment, the cell surface marker is an activation marker (meaning marker of cell activation). According to another embodiment, the activation marker is cell surface marker CD3. According to another embodiment, the activation marker is cell surface marker CD16. According to another embodiment, the activation marker is cell surface marker CD19. According to another embodiment, the activation marker is cell surface marker CD56. According to another embodiment, the activation marker is cell surface marker CD66b. According to another embodiment, the activation marker is cell surface marker HLA-DR. According to another embodiment, the activation marker is cell surface marker CD11b. According to another embodiment, the activation marker is cell surface marker CD63. According to another embodiment, the activation marker is cell surface marker CD123. According to another embodiment, the activation marker is CD203c. According to another embodiment, the activation marker is cell surface marker CD294.

According to another embodiment, the at least one non-activated basophil in the basophil population further expresses at least one intracellular marker characteristic of the at least one nonactivated basophil. According to some such embodiments, the level of expression of the intracellular marker specifically correlates to a level of expression of the at least one cell surface marker characteristic of the at least one nonactivated basophil. According to some such embodiments, the intracellular marker is a cytokine, wherein the level of expression of the cytokine is correlated to the level of expression of cell surface marker CD203c. According to another embodiment, the intracellular marker is a cytokine, wherein the level of expression of the cytokine is correlated to the level of expression of cell surface marker CD63. According to another embodiment, the intracellular marker is a cytokine, wherein the level of expression of the cytokine is correlated to the level of expression of cell surface marker CD203c and cell surface marker CD63.

According to another embodiment, the intracellular marker is a transcription factor, wherein the level of expression of the transcription factor is correlated to the level of expression of cell surface marker CD203c. According to another embodiment, the intracellular marker is a transcription factor, wherein the level of expression of the transcription factor is correlated to the level of expression of cell surface marker CD63. According to another embodiment, the intracellular marker is a transcription factor, wherein the level of expression of the transcription factor is correlated to the level of expression of cell surface marker CD203c and cell surface marker CD63.

According to another embodiment, the intracellular marker is a phosphoprotein, wherein the level of expression of the phosphoprotein is correlated to the level of expression of cell surface marker CD203c. According to another embodiment, the intracellular marker is a phosphoprotein, wherein the level of expression of the phosphoprotein is correlated to the level of expression of cell surface marker CD63. According to another embodiment, the intracellular marker is a phosphoprotein, wherein the level of expression of the phosphoprotein is correlated to the level of expression of cell surface marker CD203c and cell surface marker CD63. According to another embodiment, the intracellular marker is histamine, wherein the level of expression of histamine is correlated to the level of expression of cell surface marker CD203c and/or cell surface marker CD63.

In some such embodiments, monitoring of histamine is useful for evaluating patients for diseases of immediate hypersensitivity or mast cell proliferation (mastyocytosis). Histamine is produced and stored in cytoplasmic granules in mast cells and basophils. It also is found in other cells, including parietal cells, enterochromaffin cells, endothelial cells and platelets. Histamine mediates various biologic responses, including immediate hypersensitivity (bronchospasm, vasodilation, and increased vascular permeability), gastric acid secretion, and tissue growth and repair. Above-normal levels of histamine (reference value is <1.0 ng/ml) in plasma and urine occur after allergen challenge in patients with immediate hypersensitivity and in patients with systemic mastocytosis; above-normal levels of histamine in plasma and urine are consistent with the diagnosis of mast cell activation occurring in patients with immediate hypersensitivity or mastocytosis. Histamine appears in blood shortly after mast cell activation, however the levels may become undetectable within 60 minutes. Consequently, it may be necessary, depending on the time elapsed since allergen exposure, to measure histamine in urine either in an aliquot from an acidified 24-hour urine collection or in a random urine specimens. Owing to rapid disappearance of histamine from the blood, histamine may be undetectable if specimens are obtained hours after an allergic (anaphylactic) reaction. Further, measurements of histamine in urine are subject to interference from histamine-rich foods, including cheese, wine, red meats, spinach, and tomatoes, and are not reliable in patients with urinary tract infections. Histamine levels in blood and urine are suppressed in patients treated with antihistamine drugs. Patients should not have taken antihistamine drugs for 48 hours before testing.

According to another embodiment, the intracellular marker is a leukotriene, wherein the level of expression of leukotriene is correlated to the level of expression of cell surface marker CD203c. According to another embodiment, the intracellular marker is a leukotriene, wherein the level of expression of the leukotriene is correlated to the level of expression of cell surface marker CD63. According to another embodiment, the intracellular marker is a leukotriene, wherein the level of expression of the leukotriene is correlated to the level of expression of cell surface marker CD203c and cell surface marker CD63.

According to another embodiment, the intracellular marker is an intracellular phosphatase, wherein the level of expression of the intracellular phosphatase is correlated to the level of expression of cell surface marker CD203c. According to another embodiment, the intracellular marker is a intracellular phosphatase, wherein the level of expression of the intracellular phosphatase is correlated to the level of expression of cell surface marker CD63. According to another embodiment, the intracellular marker is a intracellular phosphatase, wherein the level of expression of the intracellular phosphatase is correlated to the level of expression of cell surface marker CD203c and cell surface marker CD63. Intracellular phosphatases include, but are not limited to, for example, phosphatase and tensin homolog (PTEN), which is believed to participate in IgE-mediated signaling for histamine release.

According to another embodiment, the allergy is a food allergy, wherein the presentation of the food allergy is correlated to the level of expression of cell surface marker CD203c and/or cell surface marker CD63. According to some such embodiments, the food allergy is a nut allergy. According to some such embodiments, the nut allergy is a peanut allergy. According to some such embodiments, the nut allergy is a tree nut allergy. According to some such embodiments, the nut allergy is a cashew allergy. According to some such embodiments, the food allergy is an apple allergy. According to some such embodiments, the food allergy is a milk allergy. According to some such embodiments, the allergy is an environmental allergy, wherein the presentation of the environmental allergy is correlated to the level of expression of cell surface marker CD203c and/or cell surface marker CD63. According to some such embodiments, the environmental allergy is a cockroach allergen allergy. According to some such embodiments, the allergy is a drug allergy, wherein the presentation of the drug allergy is correlated to the level of expression of cell surface marker CD203c and/or cell surface marker CD63. According to another embodiment, the allergy is a tree pollen allergy, wherein the presentation of the tree pollen allergy is correlated to the level of expression of cell surface marker CD203c and/or cell surface marker CD63. According to another embodiment, the allergy is a mold allergy, wherein the presentation of the mold allergy is correlated to the level of expression of cell surface marker CD203c and/or cell surface marker CD63. According to another embodiment, the allergy is a hay allergy, wherein the presentation of the hay allergy is correlated to the level of expression of cell surface marker CD203c and/or cell surface marker CD63. According to another embodiment, the allergy is a grass allergy, wherein the presentation of the grass allergy is correlated to the level of expression of cell surface marker CD203c and/or cell surface marker CD63.

According to another embodiment, the correlating of the at least one activation marker and/or the at least one intracellular marker to an allergy is performed with a computer.

II. Ex Vivo Method for Determining a Subject's Susceptibility to an Allergic Reaction According to another aspect, the described invention provides a ex vivo method for determining a subject's susceptibility to an allergic reaction to an allergen, wherein the subject has no known allergy to the allergen, the method comprising steps:

(a) collecting a whole blood sample from the subject,
wherein the whole blood sample comprises white blood cells,
wherein the white blood cells comprise at least one cell population selected from the group (i) a basophil population comprising at least one activatable basophil and (ii) an eosinophil population comprising at least one activatable eosinophil; and
wherein the basophil cell population expresses at least one cell surface marker characteristic of the at least one activatable basophil, and wherein the eosinophil cell population expresses at least one cell surface marker characteristic of the at least one activatable eosinophil;

(b) fractionating the whole blood sample by flow cytometry to separate the basophil population from the eosinophil population; and (c) correlating a level of expression of the at least one surface marker characteristic of the at least one activatable basophil, relative to a background level of expression of the at least one surface marker that is characteristic of a non-activated basophil, to susceptibility of the subject to an allergic reaction to the allergen.

According to some embodiments, correlating step (c) is performed by a computer.

According to some embodiments, the at least one surface marker is an activation marker.

According to such some embodiments, the level of expression of the at least one activation marker specifically correlates to the therapeutic effectiveness of a therapeutic agent.

According to another embodiment, the at least one activatable basophil in the basophil population further expresses at least one intracellular marker characteristic of the at least one activatable basophil. According to some such embodiments, the level of expression of the intracellular marker specifically correlates to a level of expression of the at least one cell surface marker characteristic of the at least one activatable basophil. According to such some embodiments, the level of expression of the at least one intracellular marker specifically correlates to the level of expression of an activation marker.

According to some such embodiments, level of expression of the at least one intracellular marker specifically correlates to the level of expression of the at least one activation marker and the therapeutic effectiveness of a therapeutic agent.

According to another embodiment, the intracellular marker is a cytokine, wherein the level of expression of the cytokine is correlated to the level of expression of cell surface marker CD203c. According to another embodiment, the intracellular marker is a transcription factor, wherein the level of expression of the transcription factor is correlated to the level of expression of cell surface marker CD203c. According to another embodiment, the intracellular marker is a phosphoprotein, wherein the level of expression of the phosphoprotein is correlated to the level of expression of cell surface marker CD203c. According to another embodiment, the intracellular marker is histamine, wherein the level of expression of histamine is correlated to the level of expression of cell surface marker CD203c. According to another embodiment, the intracellular marker is a leukotriene, wherein the level of expression of leukotriene is correlated to the level of expression of cell surface marker CD203c. According to another embodiment, the intracellular marker is an intracellular phosphatase, wherein the level of expression of the intracellular phosphatase is correlated to the level of expression of cell surface marker CD203c. Intracellular phosphatases include, but are not limited to, for example, phosphatase and tensin homolog (PTEN) which is believed to participate in IgE-mediated signaling for histamine release.

According to another embodiment, collecting step (a) is by venipuncture. According to another embodiment, the venipuncture is with an evacuated tube system. According to another embodiment, the venipuncture is with needle and syringe. According to another embodiment, the venipuncture is with a pin-prick puncture. According to some embodiments, the venipuncture is with a neonatal heel prick.

According to another embodiment, the whole blood sample is of a volume of about 1 drop to about 20 drops. According to another embodiment, the whole blood sample volume is of about 5 μl. According to another embodiment, the whole blood sample volume is of a volume of about 25 μl. According to another embodiment, the whole blood sample is of a volume of about 50 μl. According to another embodiment, the whole blood sample is of a volume of about 100 μl. According to another embodiment, the whole blood sample is of a volume of about 200 μl. According to another embodiment, the whole blood sample is of a volume of about 300 μl. According to another embodiment, the whole blood sample is of a volume of about 400 μl. According to another embodiment, the whole blood sample is of about 500 μl. According to another embodiment, the whole blood sample is of a volume of about 1 ml. According to another embodiment, the whole blood sample is of a volume of about 5 ml.

According to some embodiments, the allergen is a food allergen, wherein presentation of the food allergen correlates to the level of expression of the at least one activation marker and/or the at least one intracellular marker. According to some such embodiments, the activation marker is cell surface marker CD203c. According to some such embodiments, the activation marker is cell surface marker CD63. According to some such embodiments, the food allergen is a nut allergen. According to some such embodiments, the nut allergen is a peanut allergen. According to some such embodiments, the nut allergen is a cashew allergen. According to some such embodiments, the food allergen is an apple allergen. According to some such embodiments, the food allergen is a milk allergen.

According to some such embodiments, the allergen is an environmental allergen, wherein presentation of the environmental allergen correlates to the level of expression of the at least one activation marker and/or the at least one intracellular marker. According to some such embodiments, the activation marker is cell surface marker CD203c. According to some such embodiments, the activation marker is cell surface marker CD63. According to some such embodiments, the environmental allergen is a cockroach allergen allergen.

According to some such embodiments, the allergen is a drug allergen, wherein presentation of the drug allergen correlates to the level of expression of the at least one activation marker and/or the at least one intracellular marker. According to some such embodiments, the activation marker is cell surface marker CD203c. According to some such embodiments, the activation marker is cell surface marker CD63.

According to some such embodiments, the allergen is a tree allergen, wherein presentation of the tree allergen correlates to the level of expression of the at least one activation marker and/or the at least one intracellular marker. According to some such embodiments, the activation marker is cell surface marker CD203c. According to some such embodiments, the activation marker is cell surface marker CD63.

According to another embodiment, the allergen is a mold allergen, wherein presentation of the mold allergen is correlated to the level of expression of the at least one activation marker and/or the at least one intracellular marker. According to some such embodiments, the activation marker is cell surface marker CD203c. According to some such embodiments, the activation marker is cell surface marker CD63.

According to another embodiment, the allergen is a hay allergen, wherein presentation of the hay allergen is correlated to the level of expression of the at least one activation marker and/or the at least one intracellular marker. According to some such embodiments, the activation marker is cell surface marker CD203c. According to some such embodiments, the activation marker is cell surface marker CD63.

According to another embodiment, the allergen is a grass allergen, wherein presentation of the grass allergen is correlated to the level of expression of the at least one activation marker and/or the at least one intracellular marker. According to some such embodiments, the activation marker is cell surface marker CD203c. According to some such embodiments, the activation marker is cell surface marker CD63.

According to another embodiment, the whole blood sample is labeled with at least one differential label to identify a specific population of cells. According to some embodiments, the specific population of cells is a population of basophils According to some embodiments, the specific population of cells is a population of eosinophils According to some embodiments, the specific population of cells is a population of natural killer cells. According to some embodiments, the specific population of cells is a population of T cells. According to some embodiments, the specific population of cells is a population of B cells. According to some embodiments, the specific population of cells is a population of macrophages. According to some embodiments, the specific population of cells is a population of Langerhans cells.

According to some embodiments, the at least one differential label is a differential stain. According to some such embodiments, the differential stain is a chemical stain. According to some such embodiments, the chemical stains include, but are not limited to, eosin, methylene blue, Wright's stain (eosin Y, azure B and methylene blue), Jenner's stain (methylene blue eosinate), Leishman stain (methylene blue and eosin), and Giemsa stain (methylene blue and eosin).

It generally is believed that use of multicolor assays, where additional reagents are added, allows for better precision and better specificity.

According to another embodiment, the at least one differential label comprises a fluorophore.

According to some such embodiments, the at least one differential label is a fluorescent label. According to some such embodiments, the fluorescent label is a fluorescent dye or a fluorescent stain. According to some such embodiments, the fluorescent label is a Fixable Dead Cell stain (LIVE/DEAD®).

According to another embodiment, the at least one differential label is a Live-Dead® (Invitrogen, Carlsbad, Calif.) cell viability stain.

According to some such embodiments, the at least one differential label is an antibody. According to some such embodiments, the antibody is a fluorescently-labeled antibody. According to some such embodiments, the antibody is a monoclonal antibody. According to some such embodiments, the antibody is at least one antibody of a polyclonal antibody mixture.

According to some such embodiments, the fluorophore is a xanthene derivative. Xanthene derivatives include, but are not limited to, fluorescein (FITC), rhodamine, Oregon Green®, eosin, and Texas Red® (TR). According to some such embodiments, the fluorophore is a cyanine derivative. According to some such embodiments, the cyanine derivative is cyanine, indocarbocyanine, oxacarbocyanine, thiacarbocyanine or merocyanine. According to some such embodiments, the fluorophore is a coumarin derivative. According to some such embodiments, the fluorophore is a oxadiazole derivative. According to some such embodiments, the oxadiazole derivatives is pyridyloxazole, nitrobenzoxadiazole, or benzoxadiazole. According to some such embodiments, the fluorophore is a pyrene derivative. According to some such embodiments, the pyrene derivative is Cascade Blue®. According to some such embodiments, the fluorophore is a boron-dipyrromethenene (BODIPY) or derivative thereof. According to some such embodiments, the fluorophore is an oxazine derivative. According to some such embodiments, the oxazine derivative is Nile red, Nile blue, cresyl violet, or oxazine 170. According to some such embodiments, the fluorophore is a acridine derivative. Acridine derivatives include, but are not limited to, proflavin, acridine orange and acridine yellow. According to some such embodiments, the fluorophore is a arylmethine derivative. According to some such embodiments, the arylmethine derivative is auramine, crystal violet, or Malachite Greene. According to some such embodiments, the fluorophore is an Alexa Fluor®. According to some such embodiments, the fluorophore is a tetrapyrrole derivative. According to some such embodiments, the tetrapyrrole derivative is porphin, phtalocyanine or bilirubin.

According to some such embodiments, the fluorescently-labeled antibody is an antibody against cell surface marker CD3 (TCR) complex. According to some such embodiments, the antibody is mouse anti-human CD3 mAb S4.1 conjugated with a fluorophore. According to some such embodiments, the fluorophore is FITC, R-PE, TRI-COLOR®, Pacific Blue®, Alexa Fluor® 488, PE-TR, PE-Alexa Fluor® 610, PerCP, PE-Cy5.5, PE-Alexa Fluor® 700, PE-Cy7, APC, APC-Cy5.5 or APC-Alexa Fluor® 750 (Invitrogen, Carlsbad, Calif.). According to some such embodiments, the antibody is mouse anti-human mAb UCHT1 conjugated with a fluorophore. According to some such embodiments, the fluorophore is Alexa Fluor® 405, Pacific Orange™, FITC, R-PE, PE-Alexa Fluor® 700, APC or Alexa Fluor® 700 (Invitrogen, Carlsbad, Calif.).

According to some such embodiments, the fluorescently labeled antibody is an antibody against the cell surface marker CD16. According to some such embodiments, the antibody is mouse anti-human CD16 mAb 3G8 conjugated to a fluorophore. According to some such embodiments, the fluorophore is Pacific Blue™, Pacific Orange™, FITC, R-PE, PE-TR, TC, PerCP, PE-Alexa Fluor® 700, APC or Alexa Fluor® 700 (Invitrogen, Carlsbad, Calif.).

According to some such embodiments, the fluorescently labeled antibody is an antibody against the cell surface marker CD19. According to some such embodiments, the antibody is mouse anti-human CD19 mAb SJ25-C1 conjugated to a fluorophore. According to some such embodiments, the fluorophore is Alexa Fluor® 488, FITC, PE-TR, PE-Alexa Fluor® 610, PerCP, PE-Cy™ 5.5, PE-Alexa Fluor® 700, PE-Cy™ 7, APC, APC-Alexa Fluor™ 750, Pacific Blue™, Alexa Fluor® 647 or Alexa Fluor® 700 (Invitrogen, Carlsbad, Calif.).

According to some such embodiments, the fluorescently labeled antibody is an antibody against the cell surface marker CD56 (NCAM). According to some such embodiments, the antibody is mouse anti-human CD56 mAb B157; mouse anti-human CD56 mAb MEM-188 conjugated to a fluorophore. According to some such embodiments, the fluorophore is FITC, Alexa Fluor® 488, R-PE, PE-TR, TC, PE-Cy™ 5.5 (Invitrogen, Carlsbad, Calif.).

According to some such embodiments, the fluorescently labeled antibody is an antibody against cell surface marker CD66b (CGM1). According to some such embodiments, the antibody is CD66b, mouse anti-human (FITC) antibody; or CD66b antibody conjugated with a fluorophore. According to some such embodiments, the fluorophore is detectable with a laser wavelength of 407 nm.

According to some such embodiments, the fluorescently labeled antibody is an antibody against cell surface marker HLA-DR. According to some such embodiments, the antibody is HLA-DR (Class II), mouse anti-human mAb TU36 conjugated to a fluorophore. According to some such embodiments, the fluorophore is Pacific Blue™, Pacific Orange™, FITC, R-PE, PE-TR, TC, PerCP, PE-Cy™ 5.5, or APC.

According to some such embodiments, the fluorescently labeled antibody is an antibody against cell surface marker CD20. According to some such embodiments, the antibody is mouse anti-human mAb CD20 2H7 conjugated to a fluorophore such as, but not limited to, FITC (GenWay Biotech, San Diego, Calif.).

According to some such embodiments, the fluorescently labeled antibody is an antibody against cell surface marker CD123. According to some such embodiments, the antibody is PE-Cy™ 5 labeled mouse anti-human CD123 mAb 9F5; PE-labeled mouse anti-human CD123 mAb 7G3; mouse anti-human CD123 mAb 6H6 labeled with a fluorophore such as, but not limited to, FITC, PE/Cy™ 5, PE/Cy™ 7, PerCP/Cy™ 5.5, or PE (Biolegend, San Diego, Calif.; eBioscience, San Diego, Calif.).

According to some such embodiments, the fluorescently labeled antibody is an antibody against cell surface marker CD11b. According to some such embodiments, the antibody is Alexa Fluor® 488 labeled mouse anti-human CD11b mAb P1H4; FITC labeled mouse anti-human CD11b mAb 44; FITC labeled mouse anti-human CD11b mAb ICRF44; FITC labeled mouse anti-human CD11b mAb MEM-174; FITC labeled mouse anti-human CD11b mAb 44; or PE labeled mouse anti-human CD11b mAb VIM12 (Abcam Inc., Cambridge, Mass.).

According to some such embodiments, the fluorescently labeled antibody is an antibody against cell surface marker CD63. According to some such embodiments, the antibody is mouse anti-human CD63 mAb CLB-gran/12 conjugated with a fluorophore. According to some such embodiments, the fluorophore is FITC or R-PE.

According to some such embodiments, the fluorescently labeled antibody is an antibody against cell surface marker CD203c. According to some such embodiments, the antibody is PE-anti-human CD203c; PE-labeled mAb 97A6 (Immunotech, Marsielle, France); R-PE-labeled mouse anti-human ENPP3 mAb 97A6; or PE-labeled mouse anti-human CD203c mAb NP4D6.

According to some embodiments, the fluorescently labeled antibody is an antibody against cell surface marker CD294. According to some such embodiments, the antibody is Alexa Fluor® 647-labeled rat anti-CD294 mAb BM16; or PE-labeled rat anti-human CRTH2 mAb BM16.23.

According to some embodiments, the fluorescently labeled antibody is an antibody against cell surface marker CD4. According to some such embodiments the antibody is mouse anti-human CD4 mAb S3.5 conjugated to a fluorophore. According to some such embodiments, the fluorophore is Pacific Orange™, Alexa Fluor® 488, FITC, PE-TR, PE-Alexa Fluor® 610, TC, PerCP, PE-Cy™ 5.5, PE-Alexa Fluor® 700, PE-Cy™ 7, APC, APC-Cy™ 5.5, Alexa Fluor® 700, R-PE, or APC-Alexa Fluor® 750.

According to some embodiments, the fluorescently labeled antibody is an antibody against cell surface marker CD14. According to some such embodiments, the antibody is mouse anti-human CD14 mAb TuK4 conjugated to a fluorophore. According to some such embodiments, the fluorophore is Pacific Blue™, Pacific Orange™, FITC, R-PE, PE-TR, TC, PerCP, PE-Cy™ 5.5, PE-Alexa Fluor® 700, APC, APC-Alexa Fluor® 750, or Alexa Fluor® 700.

According to another embodiment, fractionating step (b) is by flow cytometry. According to some such embodiments, fractionating by flow cytometry step (b) further comprises the step utilizing a gating strategy to identify basophils. The gating strategy comprises the steps: 1) excluding doublets based on forward scatter area versus height; 2) selecting leukocytes based on forward and side scatter; 3) excluding dead cells using a fixable dead cell stain (LIVE/DEAD® Near InfraRed); and 4) selecting the basophil population as a CD3−/CD16−/CD20−/CD56−/CD66b−IHLA-DR− and CD294+ population and/or CD123+/CD203c+.

According to another embodiment, fractionating by flow cytometry step (b) further comprises the step utilizing a gating strategy to identify basophils. The gating strategy comprises the steps: 1) gating basophils based on scatter properties; 2) gating NK cells based on a level of expression of cell surface marker CD56; 3) gating B and T cells based on a level of expression of cell surface markers CD19 and CD4; 4) gating monocytes based on a level of expression of cell surface marker CD11b; and 5) gating basophils based on a level of expression of cell surface marker CD203c and cell surface marker CD294 and/or CD123+. According to some such embodiments, the basophils are sorted and stained with Giemsa solution. According to some such embodiments, an increase in the level of expression of cell surface marker CD203c from the basal level of expression of cell surface marker CD203c correlates with a decreased therapeutic effectiveness or to a suboptimal dose (meaning a dose that is below or less than the therapeutically desirable or satisfactory dose) of the therapeutic agent.

According to another embodiment, fractionating by flow cytometry step (b) further comprises the step utilizing a gating strategy to identify basophils further comprises the step of gating basophils based on a level of expression of cell surface marker CD203c and of cell surface marker CD63. According to some such embodiments, the level of expression of cell surface marker CD63 is correlated to the level of expression of cell surface marker CD203c. According to some such embodiments, the level of expression of cell surface marker CD203c measured is at least about 5-fold higher than the level of expression of cell surface marker CD63. According to some such embodiments, the level of expression of cell surface marker CD203c measured is at least about 8-fold higher than the level of expression of cell surface marker CD63.

According to another embodiment, the surface marker characteristic of the at least one basophil of step (c) is at least one activation marker. According to another embodiment, the activation marker is cell surface marker CD3. According to another embodiment, the activation marker is cell surface marker CD16. According to another embodiment, the activation marker is cell surface marker CD19. According to another embodiment, the activation marker is cell surface marker CD56. According to another embodiment, the activation marker is cell surface marker CD66b. According to another embodiment, the activation marker is cell surface marker HLA-DR. According to another embodiment, the activation marker is cell surface marker CD11b. According to another embodiment, the activation marker is cell surface marker CD63. According to another embodiment, the activation marker is cell surface marker CD123. According to another embodiment, the activation marker is cell surface marker CD203c. According to another embodiment, the activation marker is cell surface marker CD294.

III. Method for Measuring a Response to an Allergen Challenge

According to another aspect, the described invention provides a method for measuring a response to an allergen challenge in a whole blood sample obtained from an allergic subject, the method comprising steps:

(a) collecting a whole blood sample from the subject, wherein the whole blood sample comprises white blood cells,
wherein the white blood cells comprise at least one cell population selected from the group (i) a basophil population comprising at least one activatable basophil and (ii) an eosinophil population comprising at least one activatable eosinophil; and
wherein the basophil cell population expresses at least one cell surface marker characteristic of the at least one activatable basophil, and wherein the eosinophil cell population expresses at least one cell surface marker characteristic of the at least one activatable eosinophil;

(b) fractionating the whole blood sample by flow cytometry to separate the basophil population from the eosinophil population; and (c) correlating a level of expression of the at least one cell surface marker characteristic of the at least one activatable basophil to activation of the basophil population by the allergen.

According to some embodiments, correlating step (c) is performed by a computer.

According to some embodiments, the at least one cell surface marker is an activation marker.

According to another embodiment, the at least one activatable basophil in the basophil population further expresses at least one intracellular marker characteristic of the at least one activatable basophil.

According to such some embodiments, the level of expression of the at least one intracellular marker specifically correlates to the level of expression of the at least one cell surface marker.

According to some such embodiments, the level of expression of the intracellular marker specifically correlates to a level of expression of the at least one cell surface marker characteristic of the at least one activatable basophil.

According to another embodiment, the intracellular marker is a cytokine, wherein the level of expression of the cytokine is correlated to the level of expression of cell surface marker CD203c. According to another embodiment, the intracellular marker is a transcription factor, wherein the level of expression of the transcription factor is correlated to the level of expression of cell surface marker CD203c. According to another embodiment, the intracellular marker is a phosphoprotein, wherein the level of expression of the phosphoprotein is correlated to the level of expression of cell surface marker CD203c. According to another embodiment, the intracellular marker is histamine, wherein the level of expression of histamine is correlated to the level of expression of cell surface marker CD203c. According to another embodiment, the intracellular marker is a leukotriene, wherein the level of expression of leukotriene is correlated to the level of expression of cell surface marker CD203c. According to another embodiment, the intracellular marker is an intracellular phosphatase, wherein the level of expression of the intracellular phosphatase is correlated to the level of expression of cell surface marker CD203c. Intracellular phosphatases include, but are not limited to, for example, phosphatase and tensin homolog (PTEN) which is believed to participate in IgE-mediated signaling for histamine release.

According to another embodiment, collecting step (a) is by venipuncture. According to another embodiment, the venipuncture is with an evacuated tube system. According to another embodiment, the venipuncture is with needle and syringe. According to another embodiment, the venipuncture is with a pin-prick puncture. According to some embodiments, the venipuncture is with a neonatal heel prick.

According to another embodiment, the whole blood sample is of a volume of about 1 drop to about 20 drops. According to another embodiment, the whole blood sample volume is of about 5 µl. According to another embodiment, the whole blood sample volume is of a volume of about 25 µl. According to another embodiment, the whole blood sample is of a volume of about 50 µl. According to another embodiment, the whole blood sample is of a volume of about 100 µl. According to another embodiment, the whole blood sample is of a volume of about 200 µl. According to another embodiment, the whole blood sample is of a volume of about 300 µl. According to another embodiment, the whole blood sample is of a volume of about 400 µl. According to another embodiment, the whole blood sample is of about 500 µl. According to another embodiment, the whole blood sample is of a volume of about 1 ml. According to another embodiment, the whole blood sample is of a volume of about 5 ml.

According to another embodiment, the whole blood sample of step (a) is contacted with at least one allergen and optionally, with at least one second agent ex vivo.

According to another embodiment, the at least one allergen is a nut allergen. According to another embodiment, the at least one allergen is a peanut allergen. According to another embodiment, the at least one allergen is a tree nut allergen. According to another embodiment, the at least one allergen is a cashew allergen. According to another embodiment, the allergen is a food allergen. According to some such embodiments, the food allergen is an apple allergen. According to some such embodiments, the food allergen is a milk allergen. According to another embodiment, the allergen is an environmental allergen. According to some such embodiments, the environmental allergen is a cockroach allergen. According to another embodiment, the at least one allergen is a tree pollen allergen. According to another embodiment, the at least one allergen is a mold allergen. According to another embodiment, the at least one allergen is a hay allergen. According to another embodiment, the at least one allergen is a grass allergen.

According to another embodiment, the at least one optional second agent is a histamine IgE antagonist. According to another embodiment, the at least one optional second agent is a peptide antagonist. According to another embodiment, the at least one optional second agent is a peptiomimetic. According to another embodiment, the at least one optional second agent is an antibody. According to another embodiment, the at least one optional second agent is a cytokine inhibitor. According to another embodiment, the at least one optional second agent is a leukotriene inhibitor.

According to some embodiments, the allergen is a food allergen wherein presentation of the allergic reaction correlates to the level of expression of the at least one activation marker and/or the at least one intracellular marker. According to some such embodiments, the activation marker is cell surface marker CD203c. According to some such embodiments, the activation marker is cell surface marker CD63. According to some such embodiments, the food allergen is a nut allergen. According to some such embodiments, the nut allergen is a peanut allergen. According to some such embodiments, the nut allergen is a cashew allergen. According to some such embodiments, the food allergen is an apple allergen. According to some such embodiments, the food allergen is a milk allergen.

According to some such embodiments, the allergen is an environmental allergen, wherein presentation of the environmental allergen correlates to the level of expression of the at least one activation marker and/or the at least one intracellular marker. According to some such embodiments, the activation marker is cell surface marker CD203c. According to some such embodiments, the activation marker is cell surface marker CD63. According to some such embodiments, the environmental allergen is a cockroach allergen.

According to some such embodiments, the allergen is a drug allergen, wherein presentation of the drug allergen correlates to the level of expression of the at least one activation marker and/or the at least one intracellular marker. According to some such embodiments, the activation marker is cell surface marker CD203c. According to some such embodiments, the activation marker is cell surface marker CD63.

According to some such embodiments, the allergen is a tree allergen, wherein presentation of the tree allergen correlates to the level of expression of the at least one activation marker and/or the at least one intracellular marker. According to some such embodiments, the activation marker is cell surface marker CD203c. According to some such embodiments, the activation marker is cell surface marker CD63.

According to another embodiment, the allergen is a mold allergen, wherein presentation of the mold allergen is correlated to the level of expression of the at least one activation marker and/or the at least one intracellular marker. According to some such embodiments, the activation marker is cell surface marker CD203c. According to some such embodiments, the activation marker is cell surface marker CD63.

According to another embodiment, the allergen is a hay allergen, wherein presentation of the hay allergen is correlated to the level of expression of the at least one activation marker and/or the at least one intracellular marker. According to some such embodiments, the activation marker is cell surface marker CD203c. According to some such embodiments, the activation marker is cell surface marker CD63.

According to another embodiment, the allergen is a grass allergen, wherein presentation of the grass allergen is correlated to the level of expression of the at least one activation marker and/or the at least one intracellular marker. According to some such embodiments, the activation marker is cell surface marker CD203c. According to some such embodiments, the activation marker is cell surface marker CD63.

According to another embodiment, the whole blood sample is labeled with at least one differential label to identify a specific population of cells. According to some embodiments, the specific population of cells is a population of basophils According to some embodiments, the specific population of cells is a population of eosinophils According to some embodiments, the specific population of cells is a population of natural killer cells. According to some embodiments, the specific population of cells is a population of T cells. According to some embodiments, the specific population of cells is a population of B cells. According to some embodiments, the specific population of cells is a population of macrophages. According to some embodiments, the specific population of cells is a population of Langerhans cells.

According to some embodiments, the at least one differential label is a differential stain. According to some such embodiments, the differential stain is a chemical stain. According to some such embodiments, the chemical stains include, but are not limited to, eosin, methylene blue, Wright's stain (eosin Y, azure B and methylene blue), Jenner's stain (methylene blue eosinate), Leishman stain (methylene blue and eosin), and Giemsa stain (methylene blue and eosin).

It generally is believed that use of multicolor assays, where additional reagents are added, allows for better precision and better specificity.

According to another embodiment, the at least one differential label comprises a fluorophore.

According to some such embodiments, the at least one differential label is a fluorescent label. According to some such embodiments, the fluorescent label is a fluorescent dye or a fluorescent stain. According to some such embodiments, the fluorescent label is a Fixable Dead Cell stain (LIVE/DEAD®).

According to another embodiment, the at least one differential label is a Live-Dead® (Invitrogen, Carlsbad, Calif.) cell viability stain.

According to some such embodiments, the at least one differential label is an antibody. According to some such embodiments, the antibody is a fluorescently-labeled antibody. According to some such embodiments, the antibody is a monoclonal antibody. According to some such embodiments, the antibody is at least one antibody of a polyclonal antibody mixture.

According to some such embodiments, the fluorophore is a xanthene derivative. Xanthene derivatives include, but are not limited to, fluorescein (FITC), rhodamine, Oregon Green®, eosin, and Texas Red® (TR). According to some such embodiments, the fluorophore is a cyanine derivative. According to some such embodiments, the cyanine derivative is cyanine, indocarbocyanine, oxacarbocyanine, thiacarbocyanine or merocyanine. According to some such embodiments, the fluorophore is a coumarin derivative. According to some such embodiments, the fluorophore is a oxadiazole derivative. According to some such embodiments, the oxadiazole derivatives is pyridyloxazole, nitrobenzoxadiazole, or benzoxadiazole. According to some such embodiments, the fluorophore is a pyrene derivative. According to some such embodiments, the pyrene derivative is Cascade Blue®. According to some such embodiments, the fluorophore is a boron-dipyrromethenene (BODIPY) or derivative thereof. According to some such embodiments, the fluorophore is an oxazine derivative. According to some such embodiments, the oxazine derivative is Nile red, Nile blue, cresyl violet, or oxazine 170. According to some such embodiments, the fluorophore is a acridine derivative. Acridine derivatives include, but are not limited to, proflavin, acridine orange and acridine yellow. According to some such embodiments, the fluorophore is a arylmethine derivative. According to some such embodiments, the arylmethine derivative is auramine, crystal violet, or Malachite Greene. According to some such embodiments, the fluorophore is an Alexa Fluor®. According to some such embodiments, the fluorophore is a tetrapyrrole derivative. According to some such embodiments, the tetrapyrrole derivative is porphin, phtalocyanine or bilirubin.

According to some such embodiments, the fluorescently-labeled antibody is an antibody against cell surface marker CD3 (TCR) complex. According to some such embodiments, the antibody is mouse anti-human CD3 mAb S4.1 conjugated with a fluorophore. According to some such embodiments, the fluorophore is FITC, R-PE, TRI-COLOR®, Pacific Blue®, Alexa Fluor® 488, PE-TR, PE-Alexa Fluor® 610, PerCP, PE-Cy5.5, PE-Alexa Fluor® 700, PE-Cy7, APC, APC-Cy5.5 or APC-Alexa Fluor® 750 (Invitrogen, Carlsbad, Calif.). According to some such embodiments, the antibody is mouse anti-human mAb UCHT1 conjugated with a fluorophore. According to some such embodiments, the fluorophore is Alexa Fluor® 405, Pacific Orange™, FITC, R-PE, PE-Alexa Fluor® 700, APC or Alexa Fluor® 700 (Invitrogen, Carlsbad, Calif.).

According to some such embodiments, the fluorescently labeled antibody is an antibody against the cell surface marker CD16. According to some such embodiments, the antibody is mouse anti-human CD16 mAb 3G8 conjugated to a fluorophore. According to some such embodiments, the fluorophore is Pacific Blue™, Pacific Orange™, FITC, R-PE, PE-TR, TC, PerCP, PE-Alexa Fluor® 700, APC or Alexa Fluor® 700 (Invitrogen, Carlsbad, Calif.).

According to some such embodiments, the fluorescently labeled antibody is an antibody against the cell surface marker CD19. According to some such embodiments, the antibody is mouse anti-human CD19 mAb SJ25-C1 conjugated to a fluorophore. According to some such embodiments, the fluorophore is Alexa Fluor® 488, FITC, PE-TR, PE-Alexa Fluor® 610, PerCP, PE-Cy™ 5.5, PE-Alexa Fluor® 700, PE-Cy™ 7, APC, APC-Alexa Fluor™ 750, Pacific Blue™, Alexa Fluor® 647 or Alexa Fluor® 700 (Invitrogen, Carlsbad, Calif.).

According to some such embodiments, the fluorescently labeled antibody is an antibody against the cell surface marker CD56 (NCAM). According to some such embodiments, the antibody is mouse anti-human CD56 mAb B157; mouse anti-human CD56 mAb MEM-188 conjugated to a fluorophore. According to some such embodiments, the fluorophore is FITC, Alexa Fluor® 488, R-PE, PE-TR, TC, PE-Cy™ 5.5 (Invitrogen, Carlsbad, Calif.).

According to some such embodiments, the fluorescently labeled antibody is an antibody against cell surface marker CD66b (CGM1). According to some such embodiments, the antibody is CD66b, mouse anti-human (FITC) antibody; or CD66b antibody conjugated with a fluorophore. According to some such embodiments, the fluorophore is detectable with a laser wavelength of 407 nm.

According to some such embodiments, the fluorescently labeled antibody is an antibody against cell surface marker HLA-DR. According to some such embodiments, the antibody is HLA-DR (Class II), mouse anti-human mAb TU36 conjugated to a fluorophore. According to some such embodiments, the fluorophore is Pacific Blue™, Pacific Orange™, FITC, R-PE, PE-TR, TC, PerCP, PE-Cy™ 5.5, or APC.

According to some such embodiments, the fluorescently labeled antibody is an antibody against cell surface marker CD20. According to some such embodiments, the antibody is mouse anti-human mAb CD20 2H7 conjugated to a fluorophore such as, but not limited to, FITC (GenWay Biotech, San Diego, Calif.).

According to some such embodiments, the fluorescently labeled antibody is an antibody against cell surface marker CD123. According to some such embodiments, the antibody is PE-Cy™ 5 labeled mouse anti-human CD123 mAb 9F5; PE-labeled mouse anti-human CD123 mAb 7G3; mouse anti-human CD123 mAb 6H6 labeled with a fluorophore such as, but not limited to, FITC, PE/Cy™ 5, PE/Cy™ 7, PerCP/Cy™ 5.5, or PE (Biolegend, San Diego, Calif.; eBioscience, San Diego, Calif.).

According to some such embodiments, the fluorescently labeled antibody is an antibody against cell surface marker CD11b. According to some such embodiments, the antibody is Alexa Fluor® 488 labeled mouse anti-human CD11b mAb P1H4; FITC labeled mouse anti-human CD11b mAb 44; FITC labeled mouse anti-human CD11b mAb ICRF44; FITC labeled mouse anti-human CD11b mAb MEM-174; FITC labeled mouse anti-human CD11b mAb 44; or PE labeled mouse anti-human CD11b mAb VIM12 (Abcam Inc., Cambridge, Mass.).

According to some such embodiments, the fluorescently labeled antibody is an antibody against cell surface marker CD63. According to some such embodiments, the antibody is mouse anti-human CD63 mAb CLB-gran/12 conjugated with a fluorophore. According to some such embodiments, the fluorophore is FITC or R-PE.

According to some such embodiments, the fluorescently labeled antibody is an antibody against cell surface marker CD203c. According to some such embodiments, the antibody is PE-anti-human CD203c; PE-labeled mAb 97A6 (Immunotech, Marsielle, France); R-PE-labeled mouse anti-human ENPP3 mAb 97A6; or PE-labeled mouse anti-human CD203c mAb NP4D6.

According to some embodiments, the fluorescently labeled antibody is an antibody against cell surface marker CD294. According to some such embodiments, the antibody is Alexa Fluor® 647-labeled rat anti-CD294 mAb BM16; or PE-labeled rat anti-human CRTH2 mAb BM16.23.

According to some embodiments, the fluorescently labeled antibody is an antibody against cell surface marker CD4. According to some such embodiments the antibody is mouse anti-human CD4 mAb S3.5 conjugated to a fluorophore. According to some such embodiments, the fluorophore is Pacific Orange™, Alexa Fluor® 488, FITC, PE-TR, PE-Alexa Fluor® 610, TC, PerCP, PE-Cy™ 5.5, PE-Alexa Fluor® 700, PE-Cy™ 7, APC, APC-Cy™ 5.5, Alexa Fluor® 700, R-PE, or APC-Alexa Fluor® 750.

According to some embodiments, the fluorescently labeled antibody is an antibody against cell surface marker CD14. According to some such embodiments, the antibody is mouse anti-human CD14 mAb TuK4 conjugated to a fluorophore. According to some such embodiments, the fluorophore is Pacific Blue™, Pacific Orange™, FITC, R-PE, PE-TR, TC, PerCP, PE-Cy™ 5.5, PE-Alexa Fluor® 700, APC, APC-Alexa Fluor® 750, or Alexa Fluor® 700.

According to another embodiment, fractionating step (b) is by flow cytometry. According to some such embodiments, fractionating step by flow cytometry (b) by flow cytometry further comprises the step utilizing a gating strategy to identify basophils. The gating strategy comprises the steps: 1) excluding doublets based on forward scatter area versus height; 2) selecting leukocytes based on forward and side scatter; 3) excluding dead cells using a fixable dead cell stain (LIVE/DEAD® Near InfraRed); and 4) selecting the basophil population as a CD3−/CD16−/CD20−/CD56−/CD66b− IHLA-DR− and CD294+ population and/or CD123+/CD203c+.

According to another embodiment, fractionating step by flow cytometry (b) further comprises the step of utilizing a gating strategy to identify basophils. The gating strategy comprises the steps: 1) gating basophils based on scatter properties; 2) gating NK cells based on a level of expression of cell surface marker CD56; 3) gating B and T cells based on a level of expression of cell surface markers CD19 and CD4; 4) gating monocytes based on a level of expression of cell surface marker CD11b; and 5) gating basophils based on a level of expression of cell surface marker CD203c and cell surface marker CD294 and/or CD123+. According to some such embodiments, the basophils are sorted and stained with Giemsa solution. According to some such embodiments, an increase in the level of expression of cell surface marker CD203c from the basal level of expression of cell surface marker CD203c correlates with a decreased therapeutic effectiveness or to a suboptimal dose (meaning a dose that is below or less than the therapeutically desirable or satisfactory dose) of the therapeutic agent.

According to another embodiment, fractionating step by flow cytometry (b) further comprises the step of utilizing a gating strategy to identify basophils. The gating strategy comprises the step of gating basophils based on a level of expression of cell surface marker CD203c and of cell surface marker CD63. According to some such embodiments, the level of expression of cell surface marker CD63 is correlated to the level of expression of cell surface marker CD203c. According to some such embodiments, the level of expression of cell surface marker CD203c measured is at least about 5-fold higher than the level of expression of cell surface marker CD63. According to some such embodiments, the level of expression of cell surface marker CD203c measured is at least about 8-fold higher than the level of expression of cell surface marker CD63.

According to another embodiment, the surface marker characteristic of the at least one basophil of step (c) is at least one activation marker. According to another embodiment, the activation marker is cell surface marker CD3. According to another embodiment, the activation marker is cell surface marker CD16. According to another embodiment, the activation marker is cell surface marker CD19. According to another embodiment, the activation marker is cell surface marker CD56. According to another embodiment, the activation marker is cell surface marker CD66b. According to another embodiment, the activation marker is cell surface marker HLA-DR. According to another embodiment, the activation marker is cell surface marker CD11b. According to another embodiment, the activation marker is cell surface marker CD63. According to another embodiment, the activation marker is cell surface marker CD123. According to another embodiment, the activation marker is cell surface marker CD203c. According to another embodiment, the activation marker is cell surface marker CD294.

IV. System for Detection or Quantification of White Blood Cells in a Whole Blood Sample According to another aspect, the described invention provides an in vitro system for reliable detection or quantification of a specific cell population in a whole blood sample, the system comprising the following components:

(a) a whole blood sample provided by a subject;
wherein the whole blood sample comprises white blood cells,
wherein the white blood cells comprise at least one cell population selected from the group (i) a basophil population comprising at least one activatable basophil and (ii) an eosinophil population comprising at least one eosinophil
wherein the basophil cell population expresses at least one cell surface marker characteristic of the at least one activatable basophil, and wherein the eosinophil cell population expresses at least on cell surface marker characteristic of the at least one eosinophil;

(b) at least one differential label to identify a specific population of cells, (c) a means for fractionating the whole blood sample of component (a) to detect and quantify the at least one basophil population and the at least one eosinophil population; and (d) a means for correlating information from component (c) with a disease state.

According to one embodiment, component (d) is a computer.

According to another embodiment, the disease state is an allergic disease. According to some such embodiments, the allergic disease is allergic rhinitis. According to some such embodiments, the allergic disease is asthma. According to some such embodiments, the allergic disease is atopic dermatitis. According to some such embodiments, the allergic disease manifests as anaphylactic shock. According to some embodiments, the disease state is eosinophilic espohagitis, mastocytosis, anaphylaxis, an angioedema, an autoimmune disorder or a monoclonal gammopathy.

According to another embodiment, the subject has an allergy, wherein the allergy correlates to the level of expression of the least one activation marker. According to another embodiment, the subject has an allergy, wherein the allergy correlates to the level of expression of cell surface marker CD203c. According to some embodiments, the subject has an allergy, wherein the allergy correlates to the level of expression of cell surface marker CD63. According to some such embodiments, the allergy is a food allergy, wherein the food allergy correlates to the level of expression of cell surface marker CD203c. According to some embodiments, the human patient has an allergy, wherein the allergy correlates to the level of expression of cell surface marker CD63. According to some such embodiments, the food allergy is a nut allergy. According to some such embodiments, the nut allergy is a peanut allergy. According to some such embodiments, the nut allergy is a cashew allergy. According to some such embodiments, the food allergy is an apple allergy. According to some such embodiments, the food allergy is a milk allergy.

According to some such embodiments, the allergy is an environmental allergy, wherein the environmental allergy correlates to the level of expression of cell surface marker CD203c. According to some such embodiments, the allergy is an environmental allergy, wherein the environmental allergy correlates to the level of expression of cell surface marker CD63. According to some such embodiments, the environmental allergy is a cockroach allergen allergy.

According to some such embodiments, the allergy is a drug allergy, wherein the drug allergy correlates to the level of expression of cell surface marker CD203c. According to some embodiments, the allergy correlates to the level of expression of cell surface marker CD63.

According to some embodiments, the subject is at risk of having an allergy, wherein the allergy correlates to the level of expression of cell surface marker CD203c. According to some embodiments, the allergy correlates to the level of expression of cell surface marker CD63. According to some such embodiments, the allergy is a food allergy, wherein the food allergy correlates to the level of expression of cell surface marker CD203c. According to some such embodiments, the allergy is a food allergy, wherein the food allergy correlates to the level of expression of cell surface marker CD63. According to some such embodiments, the food allergy is a nut allergy. According to some such embodiments, the nut allergy is a peanut allergy. According to some such embodiments, the nut allergy is a cashew allergy. According to some such embodiments, the food allergy is an apple allergy. According to some such embodiments, the food allergy is a milk allergy.

According to some such embodiments, the allergy is an environmental allergy, wherein the environmental allergy correlates to the level of expression of cell surface marker CD203c. According to some such embodiments, the allergy is an environmental allergy, wherein the environmental allergy correlates to the level of expression of cell surface marker CD63. According to some such embodiments, the environmental allergy is a cockroach allergen allergy.

According to some such embodiments, the allergy is a drug allergy, wherein the allergy correlates to the level of expression of cell surface marker CD203c. According to some such embodiments, the allergy is a drug allergy, wherein the allergy correlates to the level of expression of cell surface marker CD63.

According to some embodiments, the subject is at risk of having an allergic disease. According to some such embodiments, the allergic disease is allergic rhinitis According to some such embodiments, the allergic disease is asthma. According to some such embodiments, the allergic disease is atopic dermatitis. According to some such embodiments, the allergic disease manifests as anaphylactic shock. According to some embodiments, the subject is at risk for eosinophilic espohagitis, mastocytosis, anaphylaxis, an angioedema, an autoimmune disorder or a monoclonal gammopathy.

According to some embodiments, the subject is under treatment with a therapeutic agent for an allergy or allergic disease, wherein the allergy or allergic disease correlates to the level of expression of cell surface marker CD203c. According to some embodiments, human patient is under treatment with a therapeutic agent for an allergy or allergic disease, wherein the allergy or allergic disease correlates to the level of expression of cell surface marker CD63.

According to another embodiment, the therapeutic agent is an antibody. According to some such embodiments, the antibody is a monoclonal antibody. According to some such embodiments, the monoclonal antibody is a humanized antibody. According to some embodiments, the monoclonal antibody is a fully human antibody. According to some embodiments, the monoclonal antibody is IgG1 monoclonal anti-IgE Fc. According to some such embodiments, the therapeutic agent is omalizumab.

According to another embodiment, component (a) further comprises at least one allergen. According to some embodiments, the at least one allergen is a nut allergen. According to some embodiments, the at least one allergen is a peanut allergen. According to some embodiments, the at least one allergen is a tree nut allergen. According to some embodiments, the at least one allergen is a cashew allergen. According to some embodiments, the allergen is a food allergen. According to some such embodiments, the food allergen is an apple allergen. According to some such embodiments, the food allergen is a milk allergen. According to another embodiment, the allergen is an environmental allergen. According to some such embodiments, the environmental allergen is a cockroach allergen. According to some such embodiments, the allergen is a tree pollen allergen. According to some such embodiments, the allergen is a grass allergen. According to some such embodiments, the allergen is a mold allergen. According to some such embodiments, the allergen is a hay allergen. According to some such embodiments, component (a) comprises an allergen array.

According to another embodiment, component (a) further comprises at least one optional second agent. According to some such embodiments, the at least one optional second agent is a histamine IgE antagonist. According to some such embodiments, the at least one optional second agent is a peptide antagonist. According to some such embodiments, the at least one optional second agent is a peptiomimetic. According to some such embodiments, the at least one optional second agent is an antibody. According to some such embodiments, the at least one optional second agent is a cytokine inhibitor. According to some such embodiments, at least one optional second agent is a leukotriene inhibitor.

According to one embodiment, the whole blood sample is collected by venipuncture. According to another embodiment, the venipuncture is by an evacuated tube system. According to another embodiment, the venipuncture is by needle and syringe. According to another embodiment, the venipuncture is by a pin-prick puncture. According to some embodiments, the venipuncture is by a neonatal heel prick.

According to another embodiment, the whole blood sample is of a volume of about 1 drop to about 20 drops. According to another embodiment, the whole blood sample volume is of about 5 µl. According to another embodiment, the whole blood sample volume is of a volume of about 25 µl. According to another embodiment, the whole blood sample is of a volume of about 50 µl. According to another embodiment, the whole blood sample is of a volume of about 100 µl. According to another embodiment, the whole blood sample is of a volume of about 200 µl. According to another embodiment, the whole blood sample is of a volume of about 300 µl. According to another embodiment, the whole blood sample is of a volume of about 400 µl. According to another embodiment, the whole blood sample is of about 500 µl. According to another embodiment, the whole blood sample is of a volume of about 1 ml. According to another embodiment, the whole blood sample is of a volume of about 5 ml.

According to some embodiments, the at least one differential label is a differential stain. According to some such embodiments, the differential stain is a chemical stain. According to some such embodiments, the chemical stain is eosin, methylene blue, Wright's stain, Jenner's stain, Leishman stain, or Giemsa stain.

It generally is believed that use of multicolor assays, where additional reagents are added, allows for better precision and better specificity.

According to another embodiment, the at least one differential label comprises a fluorophore.

According to some such embodiments, the at least one differential label is a fluorescent label. According to some such embodiments, the fluorescent label is a fluorescent dye or a fluorescent stain. According to some such embodiments, the fluorescent label is a Fixable Dead Cell stain (LIVE/DEAD®).

According to another embodiment, the at least one differential label is a Live-Dead® (Invitrogen, Carlsbad, Calif.) cell viability stain.

According to some such embodiments, the at least one differential label is an antibody. According to some such embodiments, the antibody is a fluorescently-labeled antibody. According to some such embodiments, the antibody is a monoclonal antibody. According to some such embodiments, the antibody is at least one antibody of a polyclonal antibody mixture.

According to some such embodiments, the fluorophore is a xanthene derivative. According to some such embodiments, the xanthene derivatives is fluorescein (FITC), rhodamine, Oregon Green®, eosin, or Texas Red® (TR). According to some such embodiments, the fluorophore is a cyanine derivative. According to some such embodiments, the cyanine derivative is cyanine, indocarbocyanine, oxacarbocyanine, or thiacarbocyanine and merocyanine. According to some such embodiments, the fluorophore is a coumarin derivative. According to some such embodiments, the fluorophore is a oxadiazole derivative. According to some such embodiments, the oxadiazole derivative is pyridyloxazole, nitrobenzoxadiazole, and benzoxadiazole. According to some such embodiments, the fluorophore is a pyrene derivative. According to some such embodiments, the pyrene derivative is Cascade Blue®. According to some such embodiments, the fluorophore is a boron-dipyrromethenene (BODIPY) or derivative thereof. According to some such embodiments, the fluorophore is an oxazine derivative. According to some such embodiments, the oxazine derivative is Nile red, Nile blue, cresyl violet, or oxazine 170. According to some such embodiments, the fluorophore is a acridine derivative. According to some such embodiments, the acridine derivative is proflavin, acridine orange or acridine yellow. According to some such embodiments, the fluorophore is a arylmethine derivative. According to some such embodiments, the arylmethine derivative is auramine, crystal violet, or Malachite Green®. According to some such embodiments, the fluorophore is an Alexa Fluor®. According to some such embodiments, the fluorophore is a tetrapyrrole derivative. According to some such embodiments, the tetrapyrrole derivative is porphin, phtalocyanine and bilirubin.

According to some such embodiments, the fluorescently-labeled antibody is an antibody against the cell surface marker CD3 (TCR) complex. According to some such embodiments, the antibody is mouse anti-human CD3 mAb S4.1 conjugated with a fluorophore. According to some such embodiments, the fluorophore is FITC, R-PE, TRI-COLOR®, Pacific Blue®, Alexa Fluor® 488, PE-TR, PE-Alexa Fluor® 610, PerCP, PE-Cy5.5, PE-Alexa Fluor® 700, PE-Cy7, APC, APC-Cy5.5 or APC-Alexa Fluor® 750 (Invitrogen, Carlsbad, Calif.). According to some such embodiments, the antibody is mouse anti-human mAb UCHT1 conjugated with a fluorophore. According to some such embodiments, the fluorophore is Alexa Fluor® 405, Pacific Orange™, FITC, R-PE, PE-Alexa Fluor® 700, APC or Alexa Fluor® 700 (Invitrogen, Carlsbad, Calif.).

According to some such embodiments, the fluorescently labeled antibody is an antibody against the cell surface marker CD16. According to some such embodiments, the antibody is mouse anti-human CD16 mAb 3G8 conjugated to a fluorophore. According to some such embodiments, the fluorophore is Pacific Blue™, Pacific Orange™, FITC, R-PE, PE-TR, TC, PerCP, PE-Alexa Fluor® 700, APC or Alexa Fluor® 700 (Invitrogen, Carlsbad, Calif.).

According to some such embodiments, the fluorescently labeled antibody is an antibody against the cell surface marker CD19. According to some such embodiments, the antibody is mouse anti-human CD19 mAb SJ25-C1 conjugated to a fluorophore. According to some such embodiments, the fluorophore is Alexa Fluor® 488, FITC, PE-TR, PE-Alexa Fluor® 610, PerCP, PE-Cy™ 5.5, PE-Alexa Fluor® 700, PE-Cy™ 7, APC, APC-Alexa Fluor™ 750, Pacific Blue™, Alexa Fluor® 647 or Alexa Fluor® 700 (Invitrogen, Carlsbad, Calif.).

According to some such embodiments, the fluorescently labeled antibody is an antibody against the cell surface marker CD56 (NCAM). According to some such embodiments, the antibody is mouse anti-human CD56 mAb B157, or mouse anti-human CD56 mAb MEM-188 conjugated to a fluorophore. According to some such embodiments, the fluorophore is FITC, Alexa Fluor® 488, R-PE, PE-TR, TC, PE-Cy™ 5.5 (Invitrogen, Carlsbad, Calif.).

According to some such embodiments, the fluorescently labeled antibody is an antibody against cell surface marker CD66b (CGM1). According to some such embodiments, the antibody is CD66b, mouse anti-human (FITC) antibody or CD66b antibody conjugated with a fluorophore. According to some such embodiments, the fluorophore is detectable with a laser wavelength of 407 nm.

According to some such embodiments, the fluorescently labeled antibody is an antibody against cell surface marker HLA-DR. According to some such embodiments, that antibody is HLA-DR (Class II), mouse anti-human mAb TU36 conjugated to a fluorophore. According to some such embodiments, the fluorophore is Pacific Blue™, Pacific Orange™, FITC, R-PE, PE-TR, TC, PerCP, PE-Cy™ 5.5, or APC.

According to some such embodiments, the fluorescently labeled antibody is an antibody against cell surface marker CD20. According to some such embodiments, the antibody is mouse anti-human mAb CD20 2H7 conjugated to a fluorophore. According to some such embodiments, the fluorophore is FITC (GenWay Biotech, San Diego, Calif.).

According to some such embodiments, the fluorescently labeled antibody is an antibody against cell surface marker CD123. According to some such embodiments, the antibody is PE-Cy™ 5 labeled mouse anti-human CD123 mAb 9F5; PE-labeled mouse anti-human CD123 mAb 7G3; or mouse anti-human CD123 mAb 6H6 labeled with a fluorophore such as, but not limited to, FITC, PE/Cy™ 5, PE/Cy™ 7, PerCP/Cy™ 5.5, and PE (Biolegend, San Diego, Calif.; eBioscience, San Diego, Calif.).

According to some such embodiments, the fluorescently labeled antibody is an antibody against cell surface marker CD11b. According to some such embodiments, the antibody is Alexa Fluor® 488 labeled mouse anti-human CD11b mAb P1H4; FITC labeled mouse anti-human CD11b mAb 44; FITC labeled mouse anti-human CD11b mAb ICRF44; FITC labeled mouse anti-human CD11b mAb MEM-174; FITC labeled mouse anti-human CD11b mAb 44; or PE labeled mouse anti-human CD11b mAb VIM12 (Abcam Inc., Cambridge, Mass.).

According to some such embodiments, the fluorescently labeled antibody is an antibody against cell surface marker CD63. According to some such embodiments, the antibody is mouse anti-human CD63 mAb CLB-gran/12 conjugated with a fluorophore. According to some such embodiments, the fluorophore is FITC or R-PE.

According to some such embodiments, the fluorescently labeled antibody is an antibody against cell surface marker CD203c. According to some such embodiments, the antibody is PE-anti-human CD203c; PE-labeled mAb 97A6 (Immunotech, Marsielle, France); R-PE-labeled mouse anti-human ENPP3 mAb 97A6; or PE-labeled mouse anti-human CD203c mAb NP4D6.

According to some embodiments, the fluorescently labeled antibody is an antibody against cell surface marker CD294. According to some such embodiments, the antibody is Alexa Fluor® 647-labeled rat anti-CD294 mAb BM16; or PE-labeled rat anti-human CRTH2 mAb BM16.23.

According to some such embodiments, the fluorescently labeled antibody is an antibody against cell surface marker CD4. According to some such embodiments, the antibody is mouse anti-human CD4 mAb S3.5 conjugated to a fluorophore. According to some such embodiments, the fluorophore is Pacific Orange™, Alexa Fluor® 488, FITC, PE-TR, PE-Alexa Fluor® 610, TC, PerCP, PE-Cy™ 5.5, PE-Alexa Fluor® 700, PE-Cy™ 7, APC, APC-Cy™ 5.5, Alexa Fluor® 700, R-PE, or APC-Alexa Fluor® 750.

According to some such embodiments, the fluorescently labeled antibody is an antibody against cell surface marker CD14. According to some such embodiments, the antibody is mouse anti-human CD14 mAb TuK4 conjugated to a fluorophore. According to some such embodiments, the fluorophore is Pacific Blue™, Pacific Orange™, FITC, R-PE, PE-TR, TC, PerCP, PE-Cy™ 5.5, PE-Alexa Fluor® 700, APC, APC-Alexa Fluor® 750, or Alexa Fluor® 700.

According to another embodiment, the means for fractionating component (c) is a flow cytometer. According to some such embodiments, the flow cytometer is set to identify basophils. According to some embodiments in which the flow cytometer is set to identify basophils using a gating strategy, the gating strategy comprises the steps: 1) excluding doublets based on forward scatter area versus height; 2) selecting leukocytes based on forward and side scatter; 3) excluding dead cells using a fixable dead cell stain (LIVE/DEAD® Near InfraRed); and 4) selecting the basophil population as a CD3−CD16−/CD20−/CD56−/CD66b−/HLA-DR− and CD294+ population. According to some such embodiments, the basophil population is as a CD3−CD16−/CD20−/CD56−/CD66b−IHLA-DR−, CD294+ and/or CD123+ population.

According to another embodiment, the flow cytometer is set to identify basophils using a gating strategy. The gating strategy comprises steps: 1) gating basophils based on scatter properties; 2) gating natural killer (NK) cells based on the level of expression of cell surface marker CD56; 3) gating B and T cells based on the level of expression of cell surface markers CD19 and CD4; 4) gating monocytes based on the level of expression of cell surface marker CD11b; and 5) gating basophils based on the level of expression of cell surface markers CD203c and CD294. According to some such embodiments, the gated basophils are sorted and stained with Giemsa solution. According to some embodiments, the gating of basophils is based on the level of expression of cell surface markers CD203c, CD294 and/or CD123.

According to another embodiment, the flow cytometer is set to identify basophils using a gating strategy based on expression of cell surface markers CD203c and CD63. According to some such embodiments, the level of expression of cell surface marker CD63 is correlated to the level of expression of cell surface marker CD203c. According to some such embodiments, the level of expression of cell surface marker CD203c measured is at least about 5-fold higher than the level of expression of cell surface marker CD63. According to some such embodiments, the level of expression of cell surface marker CD203c measured is at least about 8-fold higher than the level of expression of cell surface marker CD63.

According to another embodiment, the activation marker is cell surface marker CD3. According to another embodiment, the activation marker is cell surface marker CD16. According to another embodiment, the activation marker is cell surface marker CD19. According to another embodiment, the activation marker is cell surface marker CD56. According to another embodiment, the activation marker is cell surface marker CD66b. According to another embodiment, the activation marker is cell surface marker HLA-DR. According to another embodiment, the activation marker is cell surface marker CD11b. According to another embodiment, the activation marker is cell surface marker CD63. According to another embodiment, the activation marker is cell surface marker CD123. According to another embodiment, the activation marker is cell surface marker CD203c. According to another embodiment, the activation marker is cell surface marker CD294.

According to another embodiment, the intracellular marker of component (c) is a cytokine, wherein the level of expression of the cytokine is correlated to the level of expression of cell surface marker CD203c. According to another embodiment, the intracellular marker of component (c) is a transcription factor, wherein the level of expression of the transcription factor is correlated to the level of expression of cell surface marker CD203c. According to another embodiment, the intracellular marker of component (c) is a phosphoprotein, wherein the level of expression of the phosphoprotein is correlated to the level of expression of cell surface marker CD203c. According to another embodiment, the intracellular marker of component (c) is histamine, wherein the level of expression of histamine is correlated to the level of expression of cell surface marker CD203c. According to another embodiment, the intracellular marker of component (c) is a leukotriene, wherein the level of expression of leukotriene is correlated to the level of expression of cell surface marker CD203c. According to another embodiment, the intracellular marker of component (c) is an intracellular phosphatase, wherein the level of expression of the intracellular phosphatase is correlated to the level of expression of cell surface marker CD203c. Intracellular phosphatases include, but are not limited to, for example, phosphatase and tensin homolog (PTEN) which is believed to participate in IgE-mediated signaling for histamine release.

According to another embodiment, the intracellular marker of component (c) is a cytokine, wherein the level of expression of the cytokine is correlated to the level of expression of cell surface marker CD63. According to another embodiment, the intracellular marker of component (c) is a transcription factor, wherein the level of expression of the transcription factor is correlated to the level of expression of cell surface marker CD63. According to another embodiment, the intracellular marker of component (c) is a phosphoprotein, wherein the level of expression of the phosphoprotein is correlated to the level of expression of cell surface marker CD63. According to another embodiment, the intracellular marker of component (c) is histamine, wherein the level of expression of histamine is correlated to the level of expression of cell surface marker CD63. According to another embodiment, the intracellular marker of component (c) is a leukotriene, wherein the level of expression of leukotriene is correlated to the level of expression of cell surface marker CD63. According to another embodiment, the intracellular marker of component (c) is an intracellular phosphatase, wherein the level of expression of the intracellular phosphatase is correlated to the level of expression of cell surface marker CD63.

V. Method for Using a System for Detection or Quantification of White Blood Cells According to another aspect, the described invention further provides a method of using an in vitro system for reliable detection or quantification of an activated basophil fraction and activated eosinophil fraction in a whole blood sample, the system comprising the following components:

(a) a whole blood sample provided by a subject; wherein the whole blood sample comprises white blood cells, wherein the white blood cells comprise at least one cell population selected from the group (i) a basophil population comprising at least one activatable basophil and (ii) an eosinophil population comprising at least one eosinophil wherein the basophil cell population expresses at least one cell surface marker characteristic of the at least one activatable basophil, and wherein the eosinophil cell population expresses at least on cell surface marker characteristic of the at least one eosinophil;

wherein the whole blood sample is contacted with at least one allergen, and optionally with at least one 1 second agent;

(b) at least one differential label to identify a specific population of cells, (c) a means for fractionating the whole blood sample of component (a) to detect and quantify the at least one basophil population and the at least one eosinophil population; wherein the at least one activatable basophil and the at least one activatable eosinophil comprise (i) at least one activation marker and (ii) at least one intracellular marker; and (d) a means for correlating information from component (c) with a disease state.

According to one embodiment, component (d) is a computer.

According to another embodiment, the at least one cell surface marker is cell surface marker CD203c. According to another embodiment, the at least one cell surface marker is cell surface marker CD63.

According to another embodiment, the subject has an allergic disease. According to some such embodiments, the allergic disease is allergic rhinitis According to some such embodiments, the allergic disease is asthma. According to some such embodiments, the allergic disease is atopic dermatitis. According to some such embodiments, the allergic disease manifests as anaphylatic shock. According to some embodiments, the disease state is eosinophilic espohagitis, mastocytosis, anaphylaxis, an angioedema, an autoimmune disorder or a monoclonal gammopathy.

According to another embodiment, the subject has an allergy, wherein the allergy correlates to the level of expression of the least one activation marker. According to another embodiment, the subject has an allergy, wherein the allergy correlates to the level of expression of cell surface marker CD203c. According to some embodiments, the subject has an allergy, wherein the allergy correlates to the level of expression of cell surface marker CD63. According to some such embodiments, the allergy is a food allergy, wherein the food allergy correlates to the level of expression of cell surface marker CD203c. According to some embodiments, the human patient has an allergy, wherein the allergy correlates to the level of expression of cell surface marker CD63. According to some such embodiments, the food allergy is a nut allergy. According to some such embodiments, the nut allergy is a peanut allergy. According to some such embodiments, the nut allergy is a cashew allergy. According to some such embodiments, the food allergy is an apple allergy. According to some such embodiments, the food allergy is a milk allergy.

According to some such embodiments, the allergy is an environmental allergy, wherein the environmental allergy correlates to the level of expression of cell surface marker CD203c. According to some such embodiments, the allergy is an environmental allergy, wherein the environmental allergy correlates to the level of expression of cell surface marker CD63. According to some such embodiments, the environmental allergy is a cockroach allergen allergy.

According to some such embodiments, the allergy is a drug allergy, wherein the drug allergy correlates to the level of expression of cell surface marker CD203c. According to some embodiments, the allergy correlates to the level of expression of cell surface marker CD63.

According to some embodiments, the subject is at risk of having an allergy, wherein the allergy correlates to the level of expression of cell surface marker CD203c. According to some embodiments, the allergy correlates to the level of expression of cell surface marker CD63. According to some such embodiments, the allergy is a food allergy, wherein the food allergy correlates to the level of expression of cell surface marker CD203c. According to some such embodiments, the allergy is a food allergy, wherein the food allergy correlates to the level of expression of cell surface marker CD63. According to some such embodiments, the food allergy is a nut allergy. According to some such embodiments, the nut allergy is a peanut allergy. According to some such embodiments, the nut allergy is a cashew allergy. According to some such embodiments, the food allergy is an apple allergy. According to some such embodiments, the food allergy is a milk allergy.

According to some such embodiments, the allergy is an environmental allergy, wherein the environmental allergy correlates to the level of expression of cell surface marker CD203c. According to some such embodiments, the allergy is an environmental allergy, wherein the environmental allergy correlates to the level of expression of cell surface marker CD63. According to some such embodiments, the environmental allergy is a cockroach allergen allergy.

According to some such embodiments, the allergy is a drug allergy, wherein the allergy correlates to the level of expression of cell surface marker CD203c. According to some such embodiments, the allergy is a drug allergy, wherein the allergy correlates to the level of expression of cell surface marker CD63.

According to some embodiments, the subject is at risk of having an allergic disease. According to some such embodiments, the allergic disease is allergic rhinitis According to some such embodiments, the allergic disease is asthma. According to some such embodiments, the allergic disease is atopic dermatitis. According to some such embodiments, the allergic disease manifests as anaphyclatic shock. According to some embodiments, the subject is at risk for eosinophilic espohagitis, mastocytosis, anaphylaxis, an angioedema, an autoimmune disorder or a monoclonal gammopathy According to some embodiments, the subject is under treatment with a therapeutic agent for an allergy or allergic disease, wherein the allergy or allergic disease correlates to the level of expression of cell surface marker CD203c. According to some embodiments, human patient is under treatment with a therapeutic agent for an allergy or allergic disease, wherein the allergy or allergic disease correlates to the level of expression of cell surface marker CD63.

According to another embodiment, the therapeutic agent is an antibody. According to some such embodiments, the antibody is a monoclonal antibody. According to some such embodiments, the monoclonal antibody is a humanized antibody. According to some embodiments, the monoclonal antibody is a fully human antibody. According to some embodiments, the monoclonal antibody is IgG1 monoclonal anti-IgE Fc. According to some such embodiments, the therapeutic agent is omalizumab.

According to another embodiment, the at least one allergen is a nut allergen. According to some embodiments, the at least one allergen is a peanut allergen. According to some embodiments, the at least one allergen is a tree nut allergen. According to some embodiments, the at least one allergen is a cashew allergen. According to some embodiments, the allergen is a food allergen. According to some such embodiments, the food allergen is an apple allergen. According to some such embodiments, the food allergen is a milk allergen. According to another embodiment, the allergen is an environmental allergen. According to some such embodiments, the environmental allergen is a cockroach allergen. According to some embodiments, the allergen is a tree pollen allergen. According to some embodiments, the allergen is a grass allergen. According to some such embodiments, the allergen is a mold allergen. According to some such embodiments, the allergen is a hay allergen.

According to another embodiment, the at least one optional second agent is a histamine IgE antagonist. According to another embodiment, the at least one optional second agent is a peptide antagonist. According to another embodiment, the at least one optional second agent is a peptiomimetic. According to another embodiment, the at least one optional second agent is an antibody. According to another embodiment, the at least one optional second agent is a cytokine inhibitor. According to another embodiment, the at least one optional second agent is a leukotriene inhibitor.

According to one embodiment, the whole blood sample is collected by venipuncture. According to another embodiment, the venipuncture is by an evacuated tube system. According to another embodiment, the venipuncture is by needle and syringe. According to another embodiment, the venipuncture is by a pin-prick puncture. According to some embodiments, the venipuncture is by a neonatal heel prick.

According to another embodiment, the whole blood sample is of a volume of about 1 drop to about 20 drops. According to another embodiment, the whole blood sample volume is of about 5 µl. According to another embodiment, the whole blood sample volume is of a volume of about 25 µl. According to another embodiment, the whole blood sample is of a volume of about 50 µl. According to another embodiment, the whole blood sample is of a volume of about 100 µl. According to another embodiment, the whole blood sample is of a volume of about 200 µl. According to another embodiment, the whole blood sample is of a volume of about 300 µl. According to another embodiment, the whole blood sample is of a volume of about 400 µl. According to another embodiment, the whole blood sample is of about 500 µl. According to another embodiment, the whole blood sample is of a volume of about 1 ml. According to another embodiment, the whole blood sample is of a volume of about 5 ml.

According to some embodiments, the at least one differential label is a differential stain. According to some such embodiments, the differential stain is a chemical stain. According to some such embodiments, the chemical stain is eosin, methylene blue, Wright's stain, Jenner's stain, Leishman stain, or Giemsa stain.

It generally is believed that use of multicolor assays, where additional reagents are added, allows for better precision and better specificity.

According to another embodiment, the at least one differential label comprises a fluorophore.

According to some such embodiments, the at least one differential label is a fluorescent label. According to some such embodiments, the fluorescent label is a fluorescent dye or a fluorescent stain. According to some such embodiments, the fluorescent label is a Fixable Dead Cell stain (LIVE/DEAD®).

According to another embodiment, the at least one differential label is a Live-Dead® (Invitrogen, Carlsbad, Calif.) cell viability stain.

According to some such embodiments, the at least one differential label is an antibody. According to some such embodiments, the antibody is a fluorescently-labeled antibody. According to some such embodiments, the antibody is a monoclonal antibody. According to some such embodiments, the antibody is at least one antibody of a polyclonal antibody mixture.

According to some such embodiments, the fluorophore is a xanthene derivative. According to some such embodiments, the xanthene derivatives is fluorescein (FITC), rhodamine, Oregon Green®, eosin, or Texas Red® (TR). According to some such embodiments, the fluorophore is a cyanine derivative. According to some such embodiments, the cyanine derivative is cyanine, indocarbocyanine, oxacarbocyanine, or thiacarbocyanine and merocyanine. According to some such embodiments, the fluorophore is a coumarin derivative. According to some such embodiments, the fluorophore is a oxadiazole derivative. According to some such embodiments, the oxadiazole derivative is pyridyloxazole, nitrobenzoxadiazole, and benzoxadiazole. According to some such embodiments, the fluorophore is a pyrene derivative. According to some such embodiments, the pyrene derivative is Cascade Blue®. According to some such embodiments, the fluorophore is a boron-dipyrromethenene (BODIPY) or derivative thereof. According to some such embodiments, the fluorophore is an oxazine derivative. According to some such embodiments, the oxazine derivative is Nile red, Nile blue, cresyl violet, or oxazine 170. According to some such embodiments, the fluorophore is a acridine derivative. According to some such embodiments, the acridine derivative is proflavin, acridine orange or acridine yellow. According to some such embodiments, the fluorophore is a arylmethine derivative. According to some such embodiments, the arylmethine derivative is auramine, crystal violet, or Malachite Green®. According to some such embodiments, the fluorophore is an Alexa Fluor®. According to some such embodiments, the fluorophore is a tetrapyrrole derivative. According to some such embodiments, the tetrapyrrole derivative is porphin, phtalocyanine and bilirubin.

According to some such embodiments, the fluorescently-labeled antibody is an antibody against the cell surface marker CD3 (TCR) complex. According to some such embodiments, the antibody is mouse anti-human CD3 mAb S4.1 conjugated with a fluorophore. According to some such embodiments, the fluorophore is FITC, R-PE, TRI-COLOR®, Pacific Blue®, Alexa Fluor® 488, PE-TR, PE-Alexa Fluor® 610, PerCP, PE-Cy5.5, PE-Alexa Fluor® 700, PE-Cy7, APC, APC-Cy5.5 or APC-Alexa Fluor® 750 (Invitrogen, Carlsbad, Calif.). According to some such embodiments, the antibody is mouse anti-human mAb UCHT1 conjugated with a fluorophore. According to some such embodiments, the fluorophore is Alexa Fluor® 405, Pacific Orange™, FITC, R-PE, PE-Alexa Fluor® 700, APC or Alexa Fluor® 700 (Invitrogen, Carlsbad, Calif.).

According to some such embodiments, the fluorescently labeled antibody is an antibody against the cell surface marker CD16. According to some such embodiments, the antibody is mouse anti-human CD16 mAb 3G8 conjugated to a fluorophore. According to some such embodiments, the fluorophore is Pacific Blue™, Pacific Orange™, FITC, R-PE, PE-TR, TC, PerCP, PE-Alexa Fluor® 700, APC or Alexa Fluor® 700 (Invitrogen, Carlsbad, Calif.).

According to some such embodiments, the fluorescently labeled antibody is an antibody against the cell surface marker CD19. According to some such embodiments, the antibody is mouse anti-human CD19 mAb SJ25-C1 conjugated to a fluorophore. According to some such embodiments, the fluorophore is Alexa Fluor® 488, FITC, PE-TR, PE-Alexa Fluor® 610, PerCP, PE-Cy™ 5.5, PE-Alexa Fluor® 700, PE-Cy™ 7, APC, APC-Alexa Fluor™ 750, Pacific Blue™, Alexa Fluor® 647 or Alexa Fluor® 700 (Invitrogen, Carlsbad, Calif.).

According to some such embodiments, the fluorescently labeled antibody is an antibody against the cell surface marker CD56 (NCAM). According to some such embodiments, the antibody is mouse anti-human CD56 mAb B157, or mouse anti-human CD56 mAb MEM-188 conjugated to a fluorophore. According to some such embodiments, the fluorophore is FITC, Alexa Fluor® 488, R-PE, PE-TR, TC, PE-Cy™ 5.5 (Invitrogen, Carlsbad, Calif.).

According to some such embodiments, the fluorescently labeled antibody is an antibody against cell surface marker CD66b (CGM1). According to some such embodiments, the antibody is CD66b, mouse anti-human (FITC) antibody or CD66b antibody conjugated with a fluorophore. According to some such embodiments, the fluorophore is detectable with a laser wavelength of 407 nm.

According to some such embodiments, the fluorescently labeled antibody is an antibody against cell surface marker HLA-DR. According to some such embodiments, that antibody is HLA-DR (Class II), mouse anti-human mAb TU36 conjugated to a fluorophore. According to some such embodiments, the fluorophore is Pacific Blue™, Pacific Orange™, FITC, R-PE, PE-TR, TC, PerCP, PE-Cy™ 5.5, or APC.

According to some such embodiments, the fluorescently labeled antibody is an antibody against cell surface marker CD20. According to some such embodiments, the antibody is mouse anti-human mAb CD20 2H7 conjugated to a fluorophore. According to some such embodiments, the fluorophore is FITC (GenWay Biotech, San Diego, Calif.).

According to some such embodiments, the fluorescently labeled antibody is an antibody against cell surface marker CD123. According to some such embodiments, the antibody is PE-Cy™ 5 labeled mouse anti-human CD123 mAb 9F5; PE-labeled mouse anti-human CD123 mAb 7G3; or mouse anti-human CD123 mAb 6H6 labeled with a fluorophore such as, but not limited to, FITC, PE/Cy™ 5, PE/Cy™ 7, PerCP/Cy™ 5.5, and PE (Biolegend, San Diego, Calif.; eBioscience, San Diego, Calif.).

According to some such embodiments, the fluorescently labeled antibody is an antibody against cell surface marker CD11b. According to some such embodiments, the antibody is Alexa Fluor® 488 labeled mouse anti-human CD11b mAb P1H4; FITC labeled mouse anti-human CD11b mAb 44; FITC labeled mouse anti-human CD11b mAb ICRF44; FITC labeled mouse anti-human CD11b mAb MEM-174; FITC labeled mouse anti-human CD11b mAb 44; or PE labeled mouse anti-human CD11b mAb VIM12 (Abcam Inc., Cambridge, Mass.).

According to some such embodiments, the fluorescently labeled antibody is an antibody against cell surface marker CD63. According to some such embodiments, the antibody is mouse anti-human CD63 mAb CLB-gran/12 conjugated with a fluorophore. According to some such embodiments, the fluorophore is FITC or R-PE.

According to some such embodiments, the fluorescently labeled antibody is an antibody against cell surface marker CD203c. According to some such embodiments, the antibody is PE-anti-human CD203c; PE-labeled mAb 97A6 (Immunotech, Marsielle, France); R-PE-labeled mouse anti-human ENPP3 mAb 97A6; or PE-labeled mouse anti-human CD203c mAb NP4D6.

According to some embodiments, the fluorescently labeled antibody is an antibody against cell surface marker CD294. According to some such embodiments, the antibody is Alexa Fluor® 647-labeled rat anti-CD294 mAb BM16; or PE-labeled rat anti-human CRTH2 mAb BM16.23.

According to some embodiments, the fluorescently labeled antibody is an antibody against cell surface marker CD4. According to some such embodiments, the antibody is mouse anti-human CD4 mAb S3.5 conjugated to a fluorophore. According to some such embodiments, the fluorophore is Pacific Orange™, Alexa Fluor® 488, FITC, PE-TR, PE-Alexa Fluor® 610, TC, PerCP, PE-Cy™ 5.5, PE-Alexa Fluor® 700, PE-Cy™ 7, APC, APC-Cy™ 5.5, Alexa Fluor® 700, R-PE, or APC-Alexa Fluor® 750.

According to some embodiments, the fluorescently labeled antibody is an antibody against cell surface marker CD14. According to some such embodiments, the antibody is mouse anti-human CD14 mAb TuK4 conjugated to a fluorophore. According to some such embodiments, the fluorophore is Pacific Blue™, Pacific Orange™, FITC, R-PE, PE-TR, TC, PerCP, PE-Cy™ 5.5, PE-Alexa Fluor® 700, APC, APC-Alexa Fluor® 750, or Alexa Fluor® 700.

According to another embodiment, the means for fractionating component (c) is a flow cytometer. According to some such embodiments, the flow cytometer is set to identify basophils. According to some embodiments using a gating strategy, the gating strategy comprises the steps: 1) excluding doublets based on forward scatter area versus height; 2) selecting leukocytes based on forward and side scatter; 3) excluding dead cells using a fixable dead cell stain (LIVE/DEAD® Near InfraRed); and 4) selecting the basophil population as a CD3−CD16−/CD20−/CD56−/CD66b−

IHLA-DR− and CD294+ population. According to some embodiments, the selected basophil population is as a CD3−CD16−/CD20−/CD56−/CD66b−IHLA-DR−, CD294+, and or CD 123+ population.

According to another embodiment, the flow cytometer is set to identify basophils using a gating strategy. According to one such embodiment, the gating strategy comprises steps: 1) gating basophils based on scatter properties; 2) gating natural killer (NK) cells based on the level of expression of cell surface marker CD56; 3) gating B and T cells based on the level of expression of cell surface markers CD19 and CD4; 4) gating monocytes based on the level of expression of cell surface marker CD11b; and 5) gating basophils based on the level of expression of cell surface markers CD203c and CD294. According to some such embodiments, the gated basophils are sorted and stained with Giemsa solution. According to some embodiments, the gating of basophils is based on the level of expression of cell surface markers CD123+ and CD203c and/or CD294. According to another embodiment, the flow cytometer is set to identify basophils using a gating strategy based on the level of expression of cell surface markers CD203c and CD63. According to some such embodiments, the level of expression of cell surface marker CD63 is correlated to the level of expression of cell surface marker CD203c. According to some such embodiments, the level of expression of cell surface marker CD203c measured is at least about 5-fold higher than the level of expression of cell surface marker CD63. According to some such embodiments, the level of expression of cell surface marker CD203c measured is at least about 8-fold higher than the level of expression of cell surface marker CD63.

According to another embodiment, the activation marker is cell surface marker CD3. According to another embodiment, the activation marker is cell surface marker CD16. According to another embodiment, the activation marker is cell surface marker CD19. According to another embodiment, the activation marker is cell surface marker CD56. According to another embodiment, the activation marker is cell surface marker CD66b. According to another embodiment, the activation marker is cell surface marker HLA-DR. According to another embodiment, the activation marker is cell surface marker CD11b. According to another embodiment, the activation marker is cell surface marker CD63. According to another embodiment, the activation marker is cell surface marker CD123. According to another embodiment, the activation marker is cell surface marker CD203c. According to another embodiment, the activation marker is cell surface marker CD294.

According to another embodiment, the intracellular marker of component (c) is a cytokine, wherein the level of expression of the cytokine is correlated to the level of expression of cell surface marker CD203c. According to another embodiment, the intracellular marker of component (c) is a transcription factor, wherein the level of expression of the transcription factor is correlated to the level of expression of cell surface marker CD203c. According to another embodiment, the intracellular marker of component (c) is a phosphoprotein, wherein the level of expression of the phosphoprotein is correlated to the level of expression of cell surface marker CD203c. According to another embodiment, the intracellular marker of component (c) is histamine, wherein the level of expression of histamine is correlated to the level of expression of cell surface marker CD203c. According to another embodiment, the intracellular marker of component (c) is a leukotriene, wherein the level of expression of leukotriene is correlated to the level of expression of cell surface marker CD203c. According to another embodiment, the intracellular marker of component (c) is an intracellular phosphatase, wherein the level of expression of the intracellular phosphatase is correlated to the level of expression of cell surface marker CD203c. Intracellular phosphatases include, but are not limited to, for example, phosphatase and tensin homolog (PTEN) which is believed to participate in IgE-mediated signaling for histamine release.

According to another embodiment, the intracellular marker of component (c) is a cytokine, wherein the level of expression of the cytokine is correlated to the level of expression of cell surface marker CD63. According to another embodiment, the intracellular marker of component (c) is a transcription factor, wherein the level of expression of the transcription factor is correlated to the level of expression of cell surface marker CD63. According to another embodiment, the intracellular marker of component (c) is a phosphoprotein, wherein the level of expression of the phosphoprotein is correlated to the level of expression of cell surface marker CD63. According to another embodiment, the intracellular marker of component (c) is histamine, wherein the level of expression of histamine is correlated to the level of expression of cell surface marker CD63. According to another embodiment, the intracellular marker of component (c) is a leukotriene, wherein the level of expression of leukotriene is correlated to the level of expression of cell surface marker CD63. According to another embodiment, the intracellular marker of component (c) is an intracellular phosphatase, wherein the level of expression of the intracellular phosphatase is correlated to the level of expression of cell surface marker CD63.

Cell culture methods useful in the present invention are described generally in the current edition of Culture of Animal Cells: A Manual of Basic Technique (R. I. Freshney ed., Wiley & Sons); General Techniques of Cell Culture (M. A. Harrison & I. F. Rae, Cambridge Univ. Press), and Embryonic Stem Cells: Methods and Protocols (K. Turksen ed., Humana Press). Other relevant texts are Creating a High Performance Culture (Aroselli, Hu. Res. Dev. Pr. 1996) and Limits to Growth (D. H. Meadows et al., Universe Publ. 1974). Tissue culture supplies and reagents are available from commercial vendors such as Gibco/BRL, Nalgene-Nunc International, Sigma Chemical Co., and ICN Biomedicals.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and" and "the" include the plural references unless the context clearly dictates otherwise. All technical and scientific terms used herein have the same meaning.

Publications discussed herein are provided solely for their disclosure prior to the filing date of the present application. Nothing herein is to be construed as an admission that the present invention is not entitled to antedate such publication by virtue of prior invention. Further, dates of publication provided may be different from the actual publication dates which may need to be independently confirmed.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure the accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1. Rapid Basophil-CD203c Assay Identifying Offending Allergens Used to Monitor Treatment Responses in Allergy Patients

Example 1.1. Human Subjects

Clinical peanut allergy was determined by clinical history of food allergy reaction, peanut-specific IgE≥kU$_A$/L (ImmunoCAP, Phadia, Uppsala, Sweden) and/or positive skin prick test to peanut allergen. Severity was graded based on published scores of anaphylaxis symptoms (see, for example, Nowak-Wegrzyn et al., Work Group report: oral food challenge testing. J. Allergy Clin. Immunol. 2009; 123(6 Suppl): 5365-383). Five patients with peanut allergy were enrolled in a Phase I open-label study of omalizumab. Omalizumab ((Xolair®, Genentech, South San Francisco, Calif.) was dosed as per product insert guidelines based on total IgE levels and the subject's body weight.

Example 1.2. Blood Sample Collection and Processing

Blood was collected in tubes whose interior wall is coated with EDTA (commercially available from, for example, Becton, Dickson and Company (San Diego, Calif.)) by venipuncture, centrifuged (400×g for 10 minutes at 4° C.), and the leukocyte pellet retained while the plasma was centrifuged (3000×g for 10 minutes at 4° C.) to remove platelets. The blood sample then was reconstituted to its original volume by adding the platelet-free plasma to the pelleted leukocytes.

Example 1.3. Basophil Stimulation Assay

Each sample of processed blood (200 μl) was warmed for 30 seconds at 37° C., then 3 μl of phosphate buffer (PBS) or of an allergen extract (peanut, cashew, cockroach, apple) used clinically for skin testing (Greer, Lenoir, N.C., US) was added. The mixture was incubated at 37° C. for either 2 minutes, 10 minutes or 30 minutes, stopped by adding ice-cold PBS-EDTA, and the cells pelleted by centrifugation (490×g for 5 minutes at 4° C.). The supernatant was removed and stored at −80° C. until measurement of histamine was performed by a commercial vendor (for example, Mayo Clinical Laboratories, Rochester, Minn.).

Results

Figure 3A:
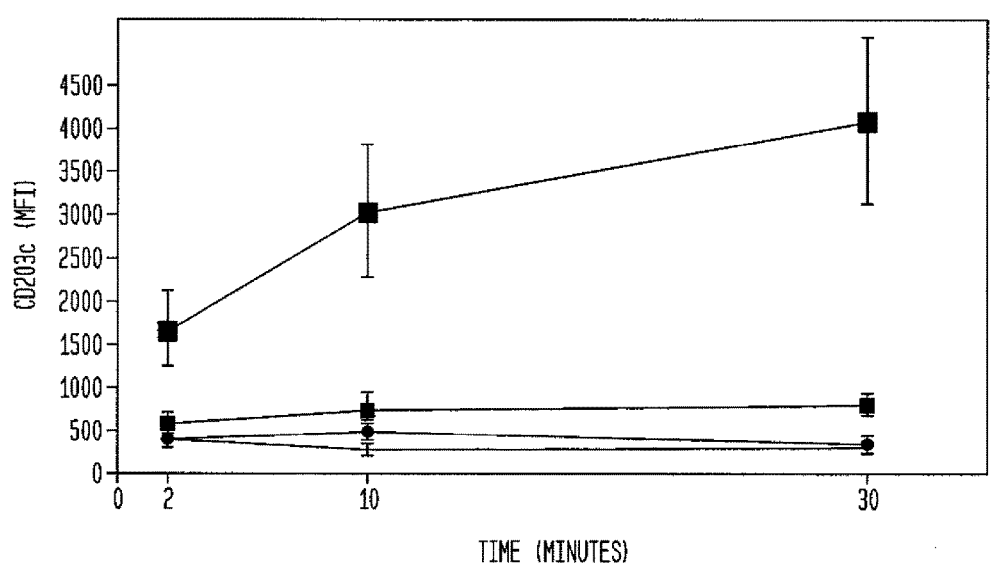
FIG. 3A shows basophils from peanut allergic patients (n=13) stimulated with peanut or cockroach were compared to those from healthy controls (n=8) stimulated with peanut or cockroach at 2 minutes, 10 minutes and 30 minutes.
Figure 3B:
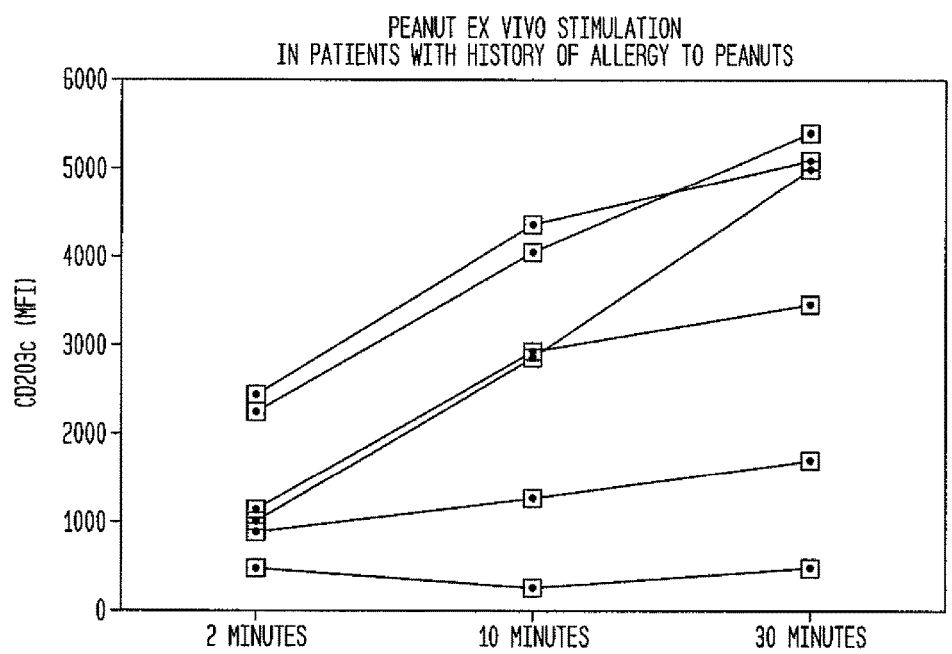
FIG. 3B and FIG. 3C represent median fluorescence intensity of CD203c in basophils from peanut allergic patients following peanut (FIG. 3B) or cockroach (FIG. 3C) ex vivo stimulation.
Figure 3C:
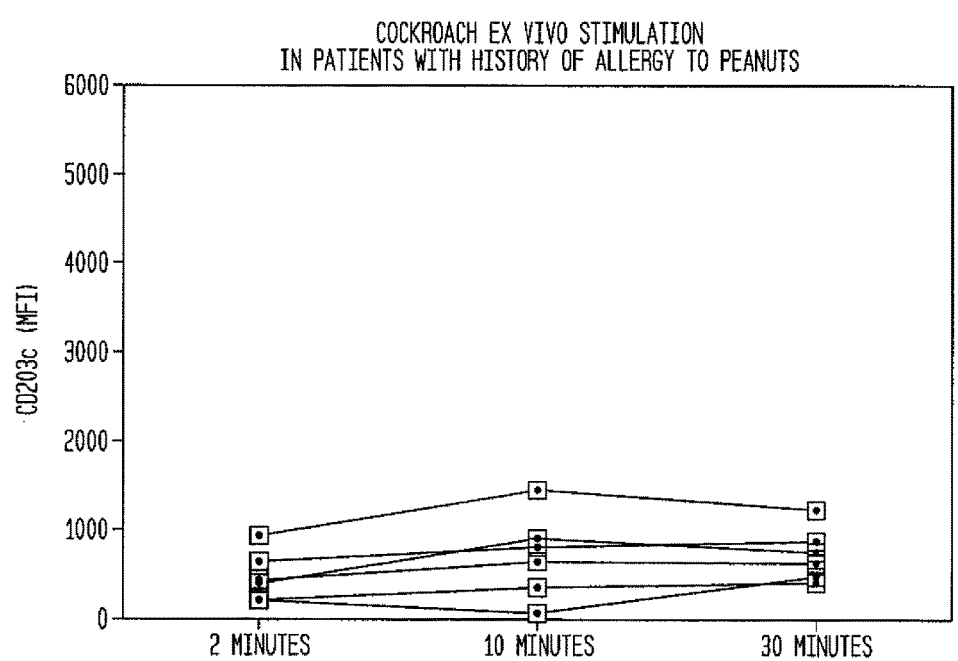

A marked upregulation of blood basophil CD203c expression was observed when blood samples from peanut allergic patients were challenged with peanut allergen ex vivo. While most basophils in an unstimulated blood sample were included in the CD203$^{neg}$ or CD203c$^{lo}$ population, most of the basophils in the stimulated sample showed increased CD203c expression and were found in the CD203c$^{hi}$ peak (bidmodal distribution) (see FIG. 2). Quantitatively, this shift was well reflected by increases in median CD203c mean fluorescence intensity (MFI) (see FIG. 3) which was >8 fold higher than the response mounted to peanut allergen by cells from healthy controls (p<0.003, Wilcoxon test). The MFI rate is a numerical relationship reflecting the severity of decreased antigen expression obtained by dividing the MFI cells exposed to allergen by the MFI of the respective cells obtained from a normal sample. Similarly, basophils from patients allergic to peanut allergen exhibited significantly higher responses to this allergen than to an allergen to which they had no relevant clinical allergic history (n=6; peanut vs. cockroach allergen challenge: 5.6, 23 and 16 fold increases, respectively, in CD203c expression after 2 minute, 10 minute or 30 minute stimulations with each of these allergens; P<0.005, P<0.006 or P<0.008, matched pairs test).

The increase in basophil CD203c expression also was observed in responses to specific allergens other than peanut, i.e., when samples from patients known to be clinically allergic to cashew, apple or cockroach were stimulated with the known offending allergens; by contrast no increase in CD203c was detected after stimulation with a non-offending allergen (see FIG. 2).

Example 1.4. High-Dimensional Flow Cytometry (Hi-D FACS)

Briefly, blood was collected in ethylene diamine tetracetic acid (EDTA) tubes by ventipuncture, centrifuged (400×g for 10 minutes at 4° C.) and the leukocyte pellet retained while the plasma was further centrifuged (3000×g for 10 minutes at 4° C.) to remove platelets. The blood sample then was reconstituted to its original volume by adding the platelet-free plasma to the pelleted leukocytes. The platelets were removed from the plasma to avoid unwanted aggregation and clotting in the course of the 30 minute assay at 37° C.

The pelleted cells prepared for the basophil stimulation assay described in Example 1.3 were resuspended in 200 μl PBS, divided equally into two tubes, and different cocktails of fluorochrome-coupled monoclonal staining reagents (80 μl/tube) were added. Each cocktail contained a fixable dead cell stain probe (LIVE/DEAD®), Invitrogen, Carlsbad, Calif.), anti-CD203c (anti-CD203c+PECy7 streptavidine) and 8 other reagents. After 20 minutes, stained cells were centrifuged, washed with excess PBS-EDT A, fixed and resuspended for analysis. Cells were acquired on a 4-laser LSRII digital flow cytometer (BD Biosciences, San Jose, Calif.). Hi-D F ACS data were compensated and analyzed with FlowJo (Treestar, Portland, Oreg.). Median fluorescence values were calculated and transferred to the JMP statistics package (SAS Institute, Cary, N.C., US) for statistical analysis.

Continuous data were tested for normality using the Shapiro-Wilk test. Between-group and within-group comparisons used the nonparametric Wicoxon rank sum and signed-rank tests, respectively. Pairwise correlations used the Pearson test. Predictive values of tests (eg, blood basophil CD203c) for subject identification (subjects with nut allergy vs healthy controls) were calculated by means of nominal logistic regression, yielding P values for negative log-likelihood $\chi^2$ tests. Predictive abilities were expressed as the area under the receiver operating characteristics ROC curve, which plots the frequency of true positive (sensitivity) against the frequency of false positive (1-specificity) results. Area values were considered excellent at more than 0.9 (1.0 is the maximal). Differences or correlations were considered significant at a P value of less than 0.05.

Figure 1B:
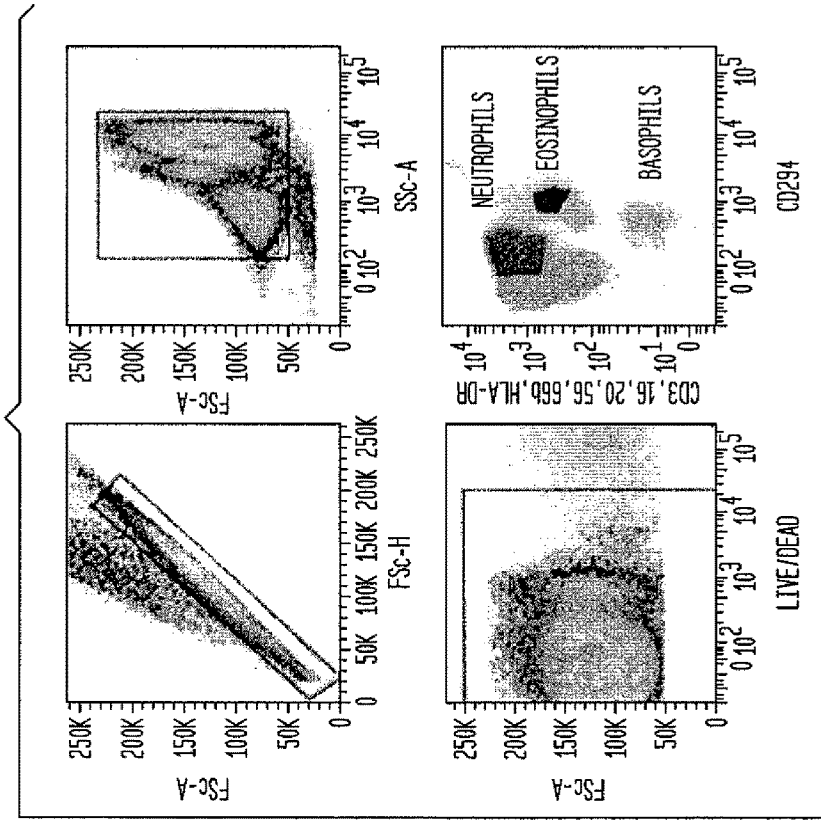
FIG. 1B shows confirmation of basophil subsets as gated found as intermediate for forward scatter (upper left panel), high for CD123 (upper right panel) and CD203chi (when stimulated with a clinical relevant allergen as shown) (upper middle panel), intermediate for CD294 and FcaR1 (lower left panel), and negative for CD16 (lower middle panel) and CD66b (lower right panel).
Figure 2A:
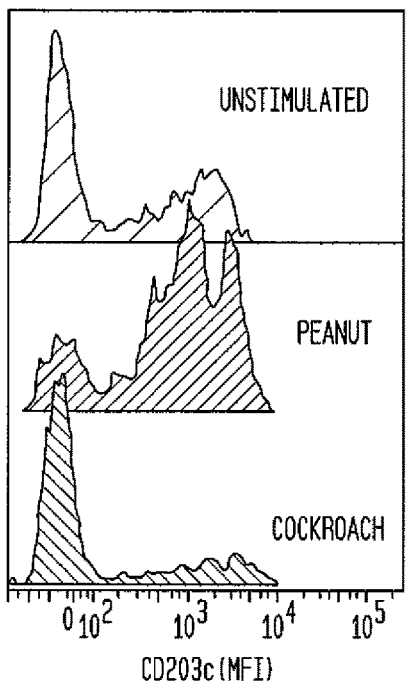
FIG. 2A shows the subject is allergic to peanuts.
Figure 2B:
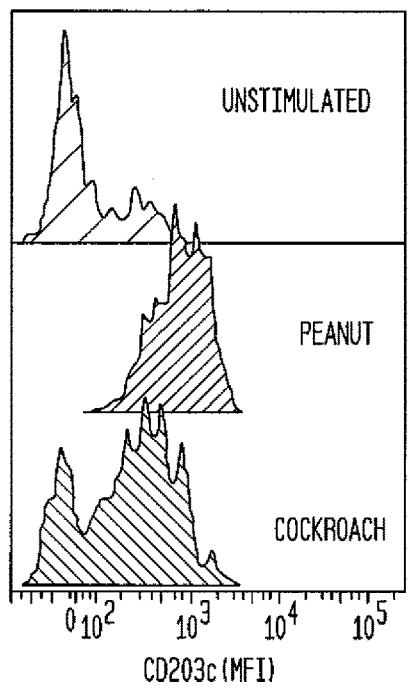
FIG. 2B shows the subject is allergic to peanuts and cockroach.
Figure 2C:
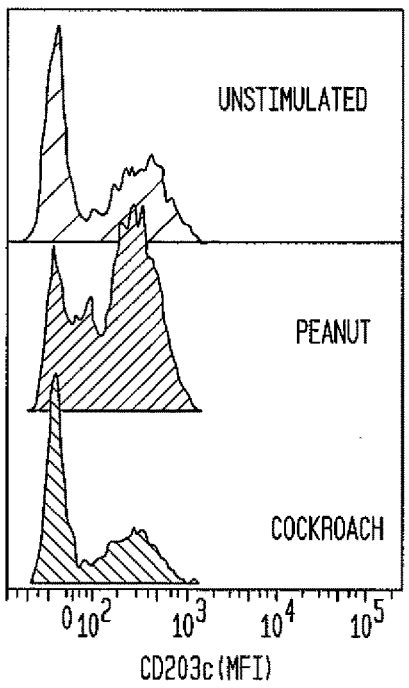
FIG. 2C shows subject presented an oral food syndrome to apple.
Figure 2D:
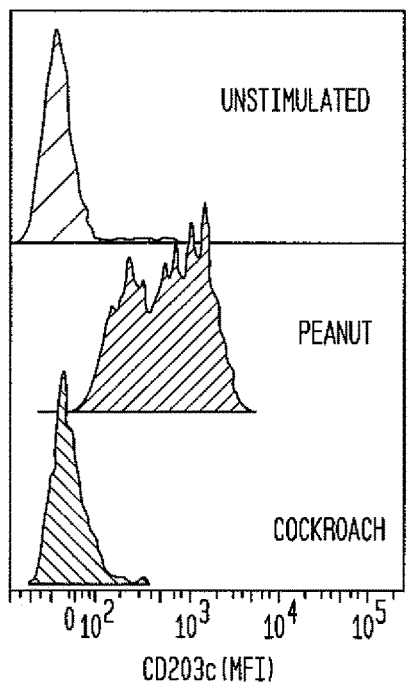
FIG. 2D shows the subject has a severe allergy to cashew. (Offending allergens are shown in bold).

High-dimensional flow cytometry and sequential gating methods were used to resolve basophils from erythrocytes (glycophorin A+) and other leukocytes in peripheral blood samples. The sequential gating method included: 1) an initial size gate to focus on single leukocytes; 2) gating out dead cells and all cells expressing at least one of the following markers not expressed on basophils: CD3 (T cells), CD16 (neutrophils, natural killer cells), CD20 (B cells), CD56 (natural killer cells), CD66b (neutrophils, eosinophils) and HLA-DR (antigen presenting cells including dendritic cells, monocytes and B cells) (see FIG. 1). The remaining population contained 0.9% of the total leukocyte population in the sample, of which basophils represent slightly above half (0.5% of the leukocyte population in peripheral blood). Basophils expressed CD123 and CD294 (see FIG. 1). In addition, unstimulated basophils expressed CD63 and CD203c at low (baseline) levels.

The reported studies were conducted with Hi-D FACS methods in which cells were stained with at least 6 fluorochromes per sample and samples were analyzed on a 4-laser DiVa flow instrument. However, the assay described is suitable for implementation on much simpler flow cytometry equipment, for example, a single laser instrument that has only two light scatter detectors and four fluorescence channels. In this case, the four available channels would be dedicated to: (i) negative markers all in one channel; (ii) a fixable dead cell stain (LIVE/DEAD®) for viability; (iii) CD123 for positive gating of basophils; and (iv) CD203c for assessing allergen-induced activation.

Figure 4:
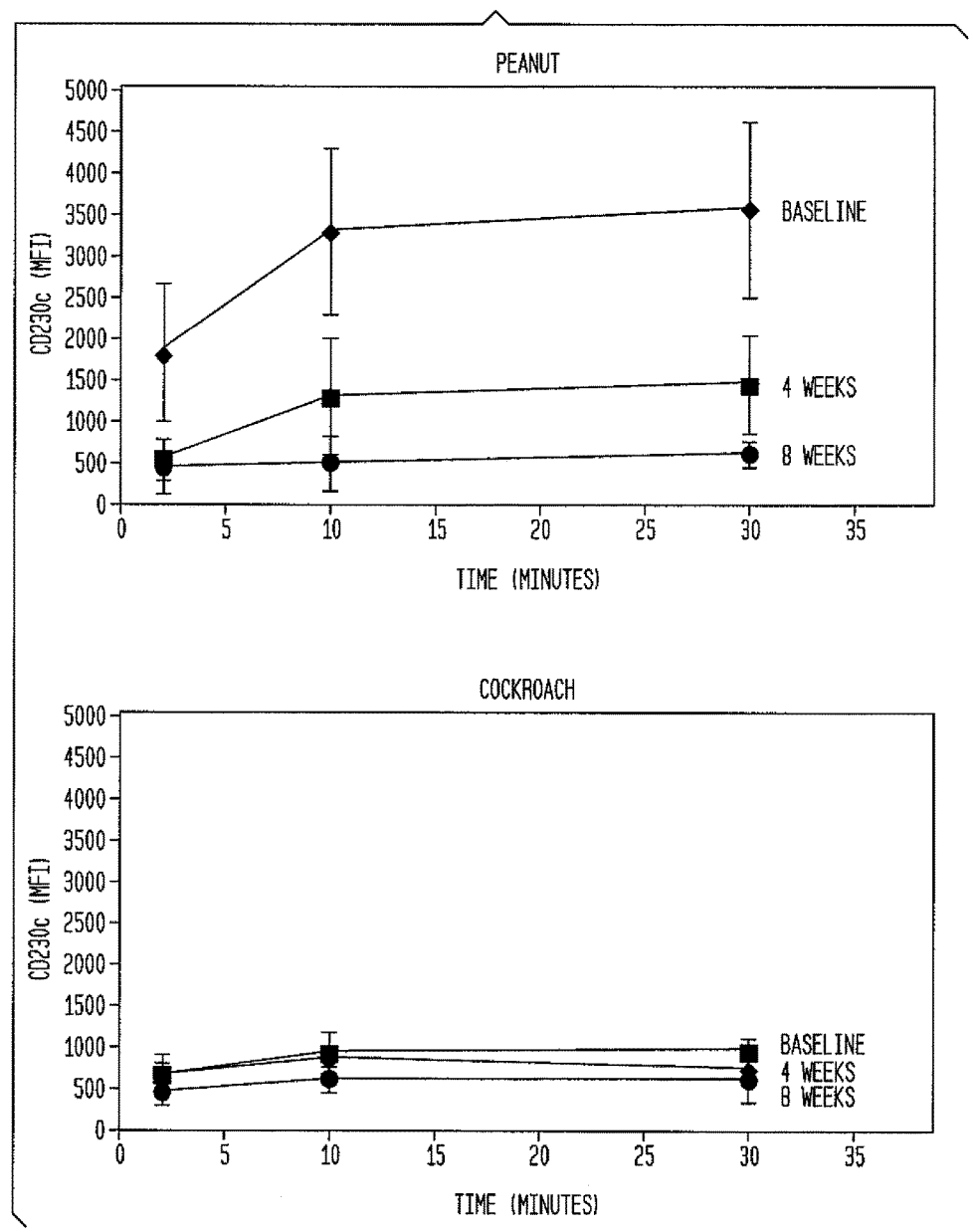
FIG. 4 shows blood basophil responses to offending allergens are decreased in allergic patients treated with humanized IgG1 monoclonal anti-IgE Fc (omalizumab). (A) data from peanut allergic patients under omalizumab treatment (P<0.034 at all time points for comparison between values at baseline and at either 4 weeks or 8 weeks on omalizumab, n=5); (B) data from the same cohort of peanut allergic patients following cockroach stimulation after 4 weeks or 8 weeks of treatment with omalizumab.

Example 1.5. Blood Basophil CD203c Responses in Human Patients Treated with Humanized IgG1 Monoclonal Anti-IgE Fc CD203c expression on blood basophils stimulated with peanut allergen ex vivo in samples drawn from peanut allergy patients at baseline and at one and two months after initiation of treatment with omalizumab (Xolair®, a humanized IgG1 monoclonal anti-IgE Fc) was measured. Results show that basophil CD203c responses to peanut allergen exposure in the treated patients decreased progressively during the treatment (difference between baseline and one or two months of therapy: P<0.034 (at either 4 weeks or 8 weeks of treatment, n=4) (see FIG. 4).

Example 1.6. Ex Vivo Basophil Activation

Histamine was detected in supernatants of peanut allergen-stimulated samples (n=5) concurrent with increases in CD203c. Furthermore, histamine levels were almost not detectable (values around 0.41 units of histamine in ng/ml of plasma represents the limit of detection) in supernatants of samples from the same subjects stimulated with the clinically irrelevant allergen (n=5) (as shown in Table X)

TABLE X

| Time Point | Peanut (mean ± SD) | Cockroach (mean ± SD) |
|---|---|---|
| 2 minutes | 72.6 ± 12.97 | 0.422 ± 0.0075 |
| 10 minutes | 94.4 ± 86.57* | 0.438 ± 0.032 |
| 30 minutes | 94 ± 8.18 | 0.41 ± 0.040 |

*= P < 0.05

Example 2. Detection of Basophils in Whole Blood Through a Two-Step Analysis

A two-step analysis process was used for the detection of basophils in human whole blood. First, erythrocytes, dead cells and the predominant leukocyte cell types were excluded according to their expression of a series of surface markers that were all tagged with the same fluorescence "color" (as "dump channel"). Next, the basophils were identified among the remaining cells by their joint expression of the markers CD123 and CD203c, each tagged with a unique fluorescence color. The identified basophils were counted and/or stored for further experiments.

Figure 5:
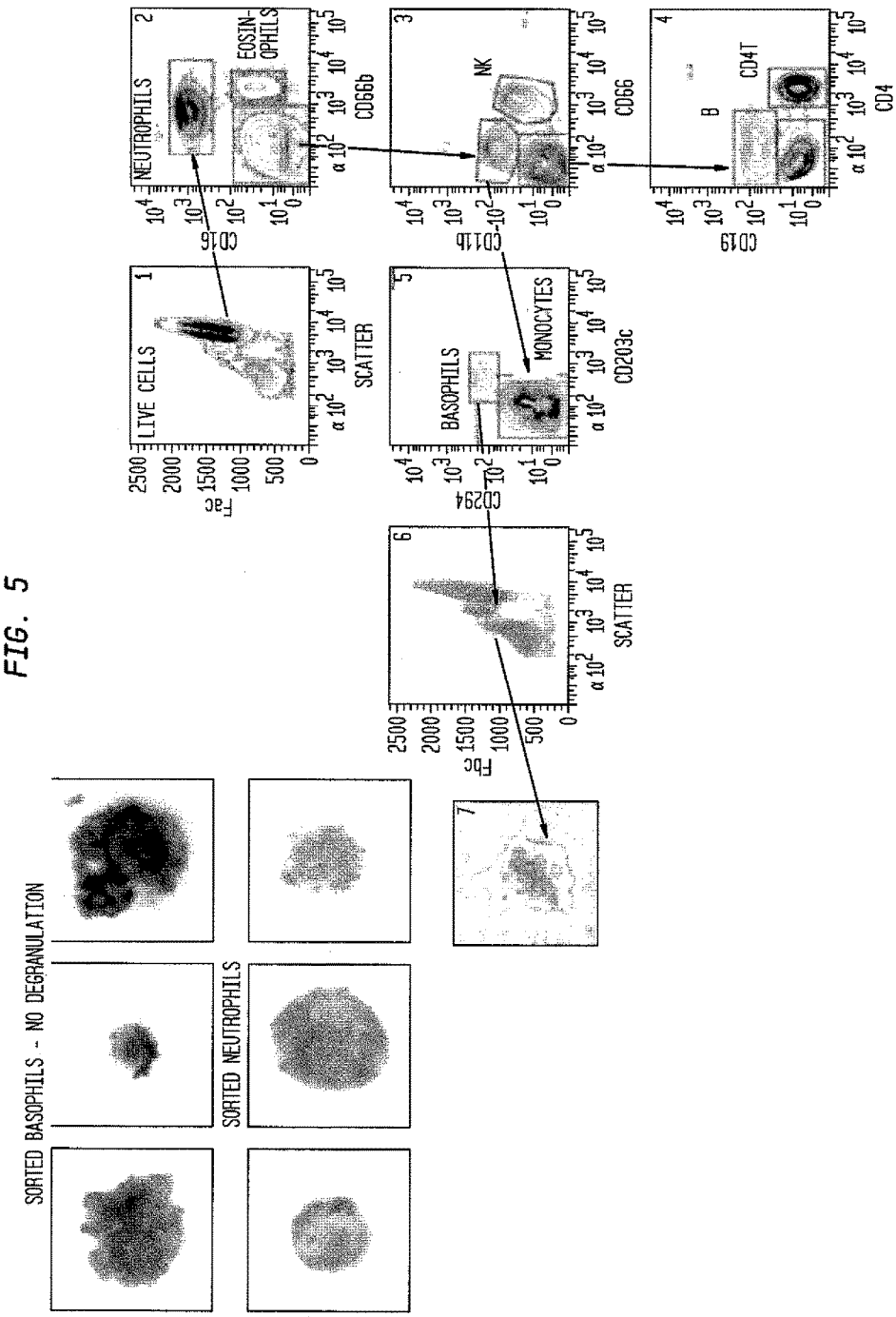
FIG. 5 shows high-definition FACS surface staining of basophils in human blood with whole blood staining to minimize procedure-related activation.

FIG. 5 shows the isolation of basophils from whole blood of a human asthmatic patient without a purification or stimulation step. The basophil gating strategy comprised the following steps: 1) basophils were gated on scatter properties; 2) neutrophils and eosinophils were gated based on CD66b and CD16; 3) NK were gated based on CD56; 4) B and T cells were gated based on CD19 and CD4; 5) monocytes were gated based on CD11b; and 6) basophils were gated based on CD203c and CD294. Basophils were sorted and stained with Giemsa solution. These cells contained large cytoplasmic granules which obscured the cell nucleus during microscopic observation. Neutrophils were sorted as a control population with the same gating strategy.

Figure 6:
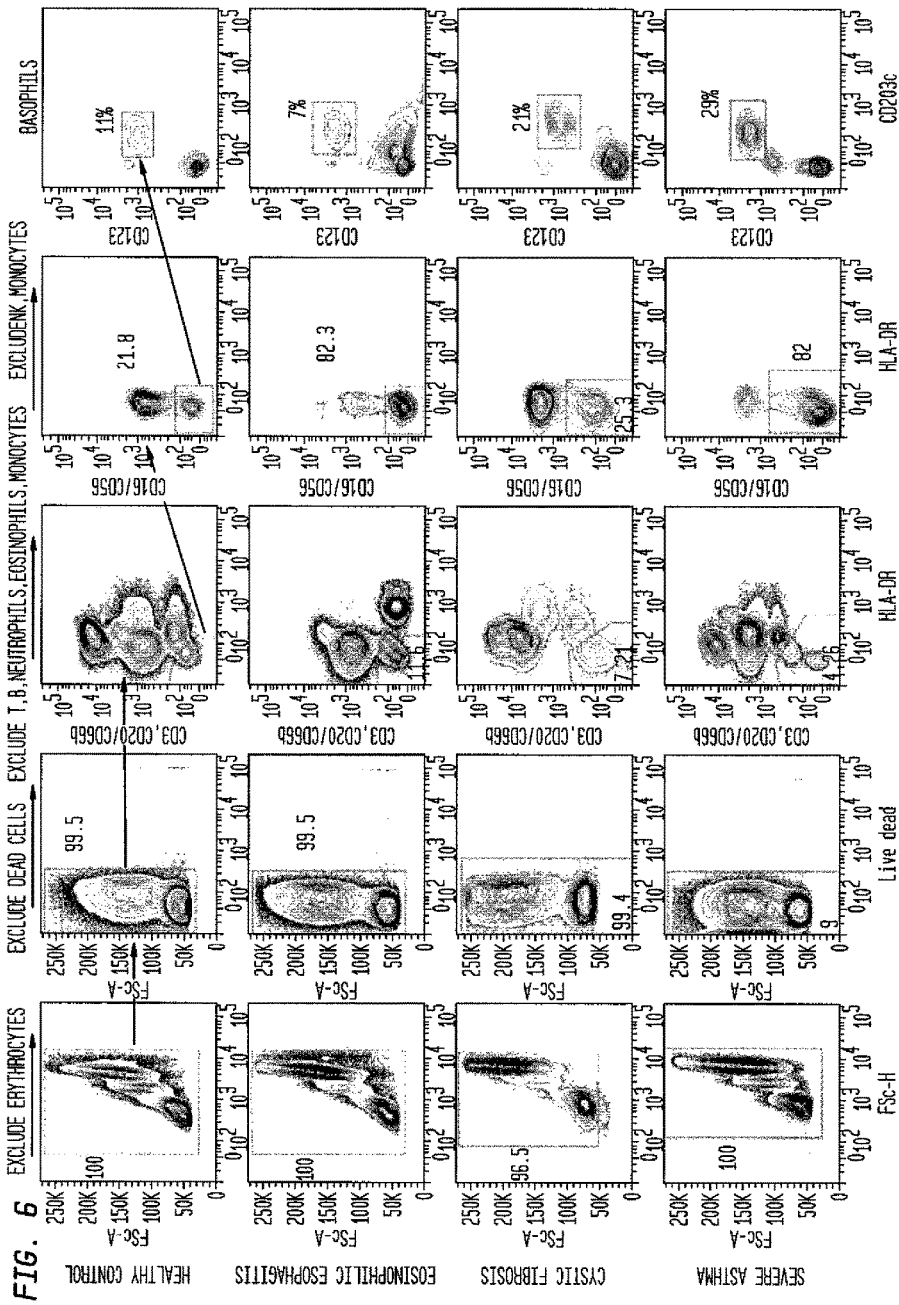
FIG. 6 shows the detection of basophils in blood of subjects with eosinophilic esophagitis, cystic fibrosis, and severe asthma in comparison to a healthy subject.

Example 3. Detection of Basophils in Minute Amounts of Whole Blood in Asthmatic Patients Basophils were detected from minute amounts of whole blood from asthmatic patients. FIG. 6 shows the isolation strategy. First, red blood cells were excluded based on the forward scatter and side scatter profile. Second, the dead cells were excluded using a fixable dead cell stain (LIVE/DEAD®, Invitrogen). Third, T and B cells, neutrophils (PNP) and eosinophils (PNE) were excluded based on CD3, CD19, HIA-DR, and CD66b. Fourth, NK cells were excluded based on CD16/CD56.5. Basophils were gated based on CD123 and CD203c.

Example 4. Basophil Intracellular Signalization

Figure 7:
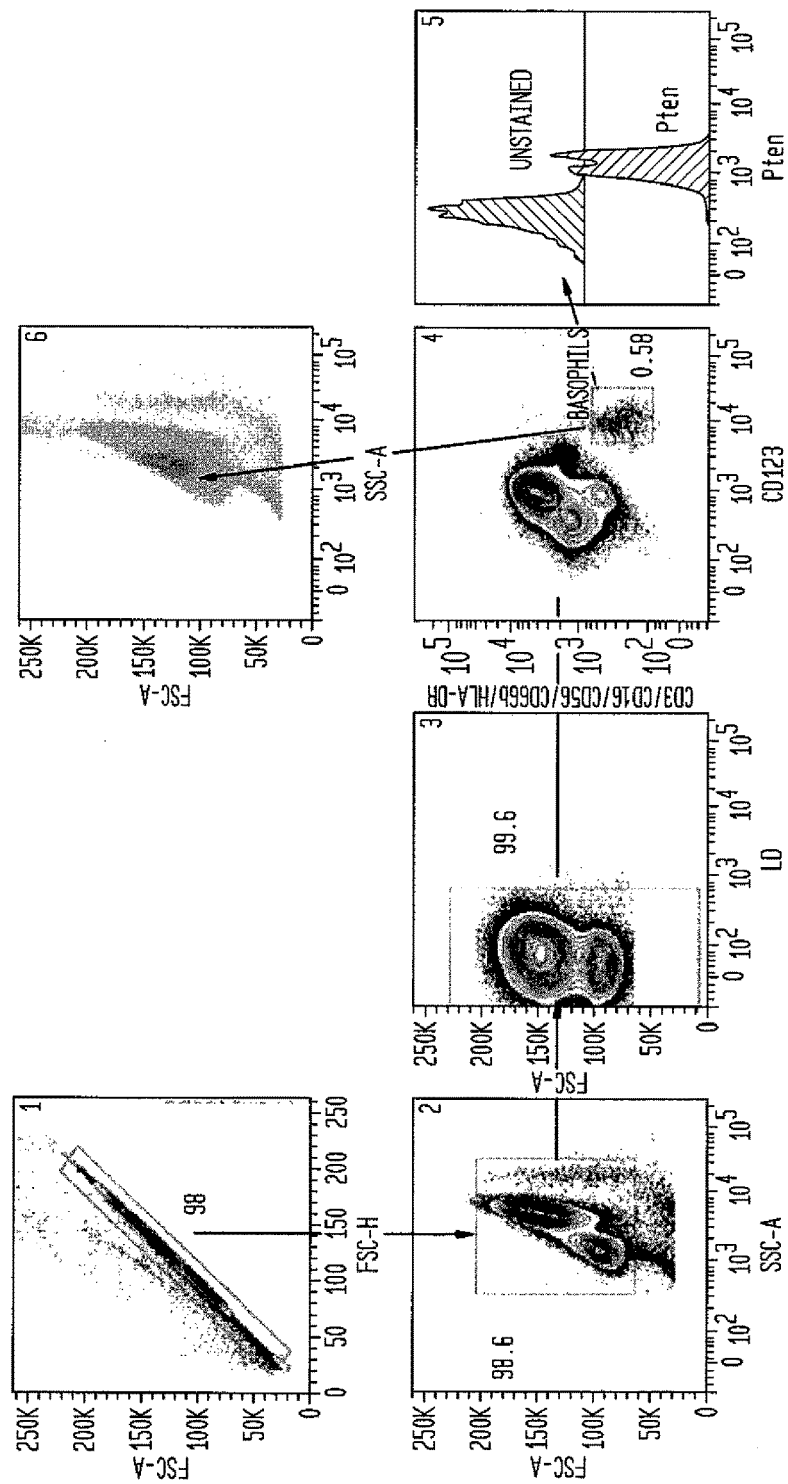
FIG. 7 shows high-definition FACS intracellular signaling of basophils in human blood with whole blood staining to minimize procedure-related activation.

FIG. 7 shows histograms from the following gating strategy which illustrated basophil intracellular signalization. First, single cells were gated based on the forward scatter and side scatter. Second, leukocytes were selected based on forward scatter and area and height scatter. Third, the compromised cells were excluded using a fixable dead cell stain (LIVE/DEAD®). Fourth, B, T, NK cells, and neutrophils, monocytes, eosinophils were excluded. Basophils were selected based on CD123+, dump−. Fifth, a PTEN (phosphatase and tensin homolog (intracellular phosphatase)) signal was observed.

Example 5. Eosinophil Intracellular Signalization

Figure 8:
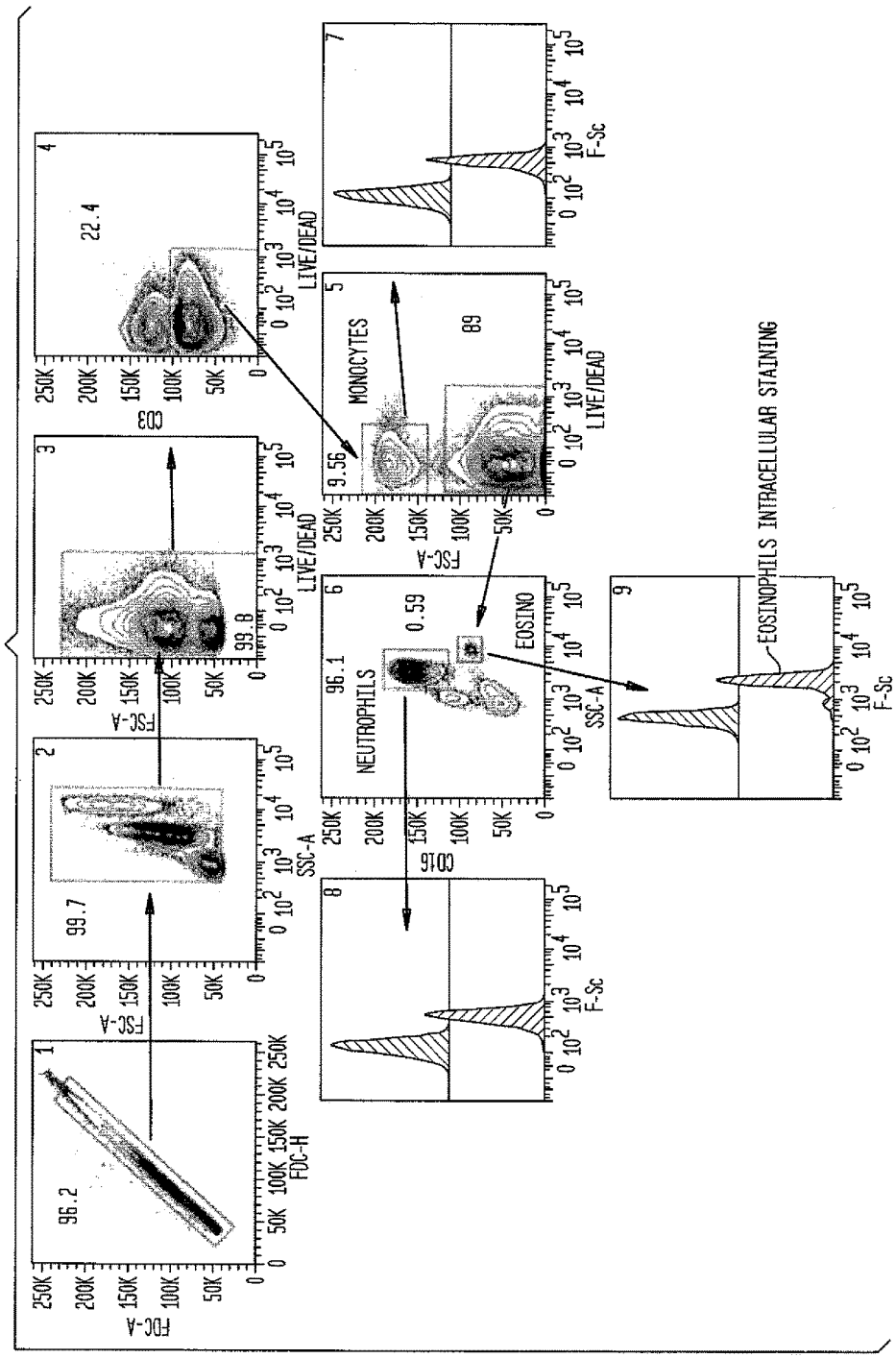
FIG. 8 shows high-definition FACS surface and intracellular staining of eosinophils from 1 drop of whole blood.

FIG. 8 shows histograms illustrative of eosinophil intracellular signalization. First, the singlets were gated based on the forward scatter and the side scatter. Second, the granulocytes and lymphocytes were gated based on forward scatter and side scatter. Third, the dead cells were excluding by using a fixable dead cell stain (LIVE/DEAD®). Fourth, T cells were excluded. Fifth, monocytes were selected based on CD14, and the expression of the intracellular phosphorylated Src phophoepitope measured. Sixth, the neutrophils and eosinophils, based on CD16 and side scatter, were isolated and the expression of intracellular phosphorylated Src measured.

Example 6. Distribution of CD203c at Baseline (Major CD203c$^{lo}$ Peak) and Following Ex Vivo Stimulation with an Offending Allergen Whole blood from one allergic patient was collected and analyzed. The sample was stained for all markers except CD203c (CD203cFMO (fluorescence minor one); FMO controls reveal the maximum fluorescence expected in a given subset in a given channel when the reagent used in that channel is omitted from the stain set) and compared to whole blood stained for all markers with CD203c (CD203cAb=antibody).

Figure 9:
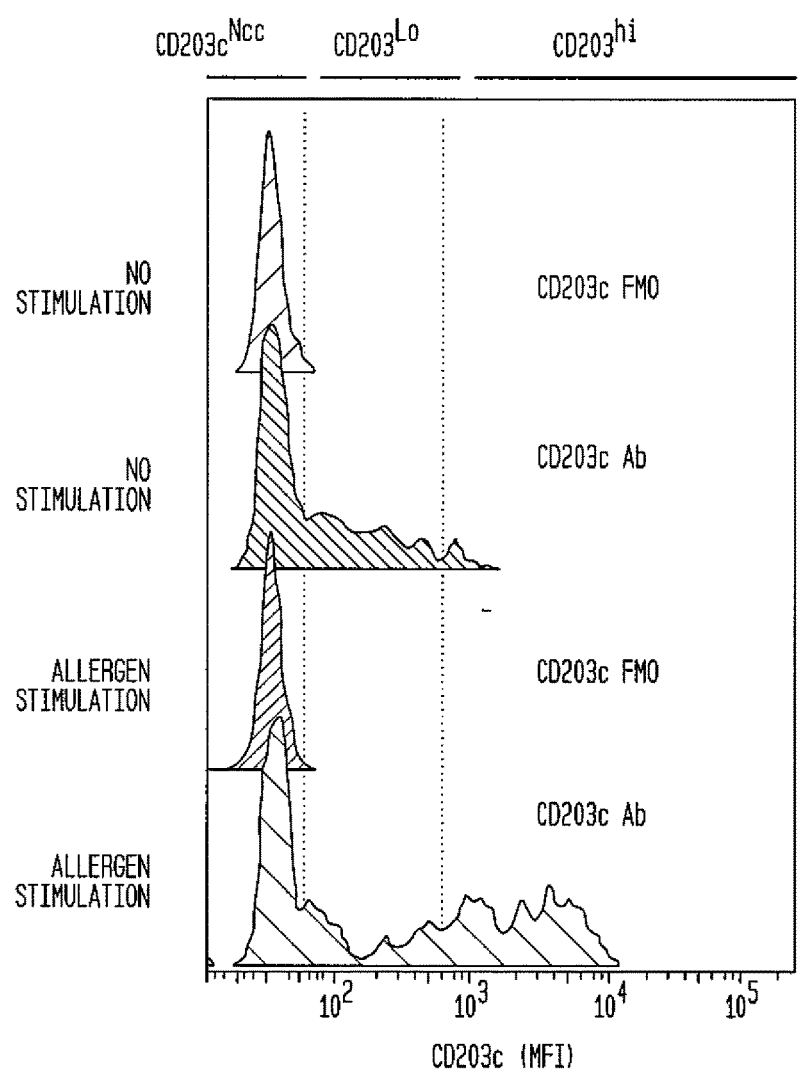
FIG. 9 shows graphs representing the distribution of CD203c at baseline and following ex vivo stimulation with an offending allergen.

FIG. 9 shows the distribution of CD203c at baseline and following ex vivo stimulation with an offending allergen. This allowed for gating, and defined basophils as CD203c$^{neg}$, CD203$^{lo}$ and CD203c$^{hi}$ populations.

Example 7. Changes in Basophil CD63 Surface Expression

Basophils from peanut allergic patients stimulated with peanut or cockroach allergen were compared to basophils from healthy patients stimulated with peanut or cockroach allergen at 2 minutes, 10 minutes and 30 minutes.

Figure 10A:
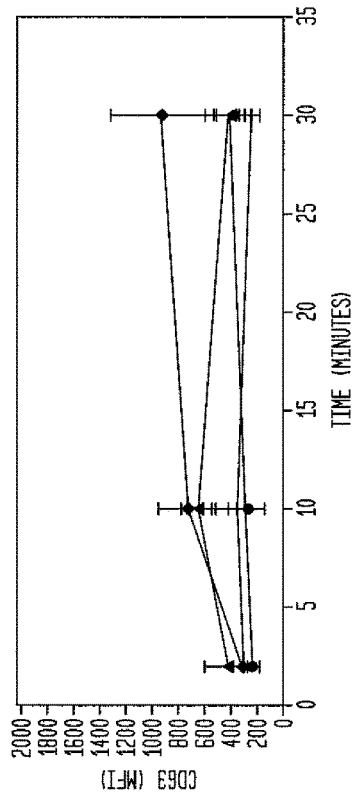
FIG. 10A shows peanut and cockroach ex vivo stimulation in healthy patients.
Figure 10C:
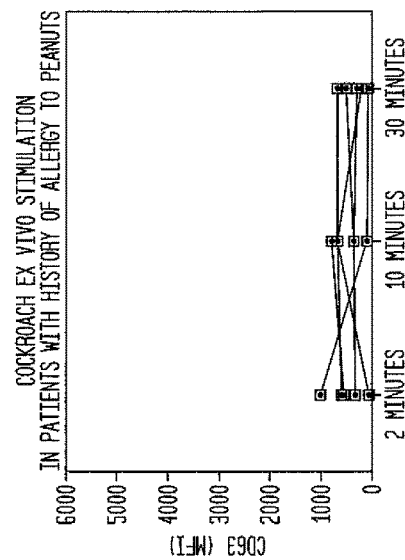
FIG. 10C shows cockroach ex vivo stimulation in patients with a history of allergy to peanuts.
Figure 10B:
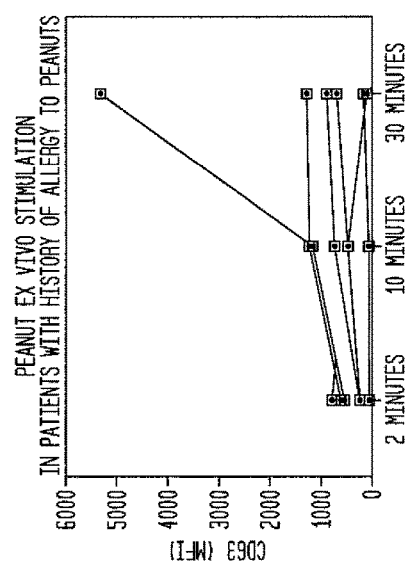
FIG. 10B shows peanut ex vivo stimulation in patients with a history of allergy to peanuts.

FIG. 10 shows graphs of the CD63 (MFI) versus time. No significant difference was observed between values measured when peanut allergic subjects (FIG. 10B) were stimulated with peanut versus a clinically irrelevant allergen (cockroach) (FIG. 10C) (n=6). CD63 was not increased on basophils in blood samples from the healthy patients after stimulation with these same allergens (n=6) (FIG. 10A).

These results indicate that cell surface marker CD63 alone is not as specific as CD203c alone to serve as a diagnostic marker for the diagnosis of IgE mediated allergy.

Example 8. Changes in Basophil CD11b, CD63 and CD123 Surface Expression

Levels of CD11b, CD63 and CD123 on basophils, neutrophils and eosinophils from a peanut allergic patient were measured following ex vivo peanut allergen exposure.

Figure 11:
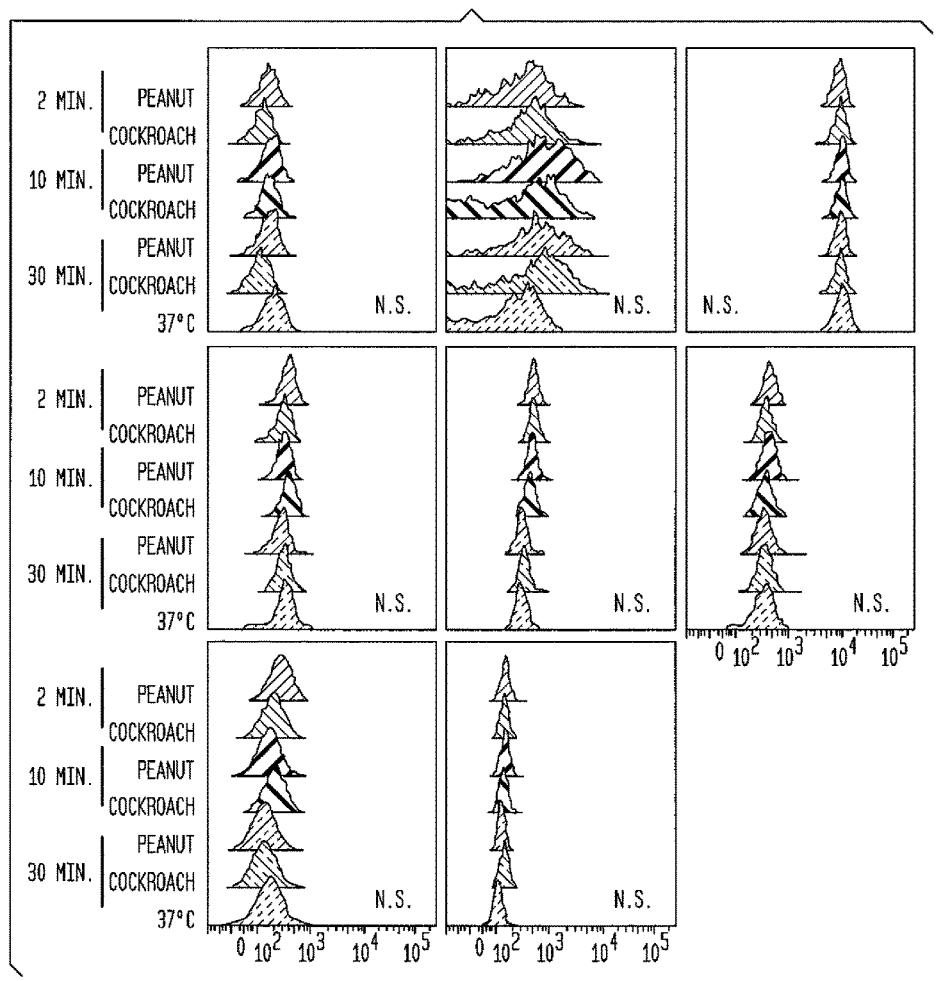
FIG. 11 shows illustrative graphs from one peanut allergic patient of the surface expression of CD11b, CD63 and CD123 on basophils, neutrophil and eosinophils.

FIG. 11 shows illustrative graphs from one peanut allergic patient of the surface expression of CD11b (top row), CD63 (middle row) and CD123 (bottom row) on basophils, neutrophil and eosinophils. The levels of CD11b, CD63 and CD123 expressed on the surface of these cells does not change significantly following ex vivo allergen exposure.

While the present invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the present invention. All such modifications are intended to be within the scope of the claims appended hereto.

What is claimed is:

1. A method for determining a subject's susceptibility to an allergic reaction, the method comprising:
    (a) stimulating a whole blood sample from the subject with an allergen, wherein the whole blood sample comprises a basophil cell population;
    (b) labeling the whole blood sample with anti-CD203c and a differential label for phosphatase and tensin homolog (PTEN); and
    (c) measuring a level of expression of CD203c and PTEN using flow cytometry and comparing the level of expression to a control sample, wherein a higher level of expression of CD203c and PTEN in the basophil cell population compared to the control sample is indicative of increased susceptibility to an allergic reaction to the allergen in the subject.

2. The method according to claim 1, wherein the whole blood sample is stimulated with the allergen ex vivo.

3. The method according to claim 1, wherein the anti-CD203c is a fluorescently-labeled antibody.

4. The method according to claim 1, wherein the whole blood sample is of a volume of about 5 µl to about 500 µl.

5. The method according to claim 1, wherein the allergen is selected from the group consisting of a food allergen, a peanut allergen, a cashew allergen, an apple allergen, a milk allergen, an environmental allergen, a cockroach allergen, a tree pollen allergen, a grass allergen, a mold allergen, a hay allergen, a drug allergen, and a combination thereof.

6. The method according to claim 1, further comprising labeling the whole blood sample with one or a plurality of antibodies to CD123 or CD294.

7. The method according to claim 6, further comprising measuring the level of expression of one or a plurality of CD123 or CD294 using flow cytometry.

8. The method according to claim 7, wherein the flow cytometry identifies the basophil cell population using a gating strategy comprising:
    1) excluding doublets based on forward scatter area versus height;
    2) selecting leukocytes based on forward and side scatter;
    3) excluding dead cells using a fixable dead cell stain; and
    4) selecting the basophil cell population as expressing detectable levels of CD294 and CD123.

9. The method according to claim 1, wherein comparing the level of expression of CD203c and PTEN to a control sample is performed by computer.

10. The method according to claim 1, wherein the subject has no known allergy to the allergen.

11. The method according to claim 5, wherein the drug allergen is penicillin.

12. The method according to claim 1, wherein the differential label for PTEN is a chemical stain or a fluorescently-labeled antibody.

* * * * *

UNITED STATES PATENT AND TRADEMARK OFFICE
CERTIFICATE OF CORRECTION

PATENT NO. : 10,114,012 B2
APPLICATION NO. : 12/610940
DATED : October 30, 2018
INVENTOR(S) : Yael Gernez et al.

It is certified that error appears in the above-identified patent and that said Letters Patent is hereby corrected as shown below:

In the Specification

In Column 1, Lines 12-19, delete the subtitle and paragraph reproduced below:
"STATEMENT OF GOVERNMENT FUNDING
This invention was made with government support under Grant Dean Fellowship Morgridge and Gallo Fellowship, AAAAI fellowship awarded by the Stanford and AAAAI foundation. The government has certain rights in the invention."

Signed and Sealed this
Twelfth Day of November, 2019

Andrei Iancu
*Director of the United States Patent and Trademark Office*